(12) United States Patent
Wu et al.

(10) Patent No.: US 9,174,969 B2
(45) Date of Patent: Nov. 3, 2015

(54) INDOLINE SCAFFOLD SHP-2 INHIBITORS AND CANCER TREATMENT METHOD

(75) Inventors: Jie Wu, Tampa, FL (US); Nicholas J. Lawrence, Tampa, FL (US); Said M. Sebti, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 289 days.

(21) Appl. No.: 13/055,113

(22) PCT Filed: Jul. 21, 2009

(86) PCT No.: PCT/US2009/051276
§ 371 (c)(1),
(2), (4) Date: Apr. 15, 2011

(87) PCT Pub. No.: WO2010/011666
PCT Pub. Date: Jan. 28, 2010

(65) Prior Publication Data
US 2011/0190315 A1 Aug. 4, 2011

Related U.S. Application Data

(60) Provisional application No. 61/082,382, filed on Jul. 21, 2008, provisional application No. 61/170,354, filed on Apr. 17, 2009.

(51) Int. Cl.
A61K 31/496 (2006.01)
C07D 209/08 (2006.01)
C07D 215/36 (2006.01)
C07D 405/06 (2006.01)

(52) U.S. Cl.
CPC .......... *C07D 405/06* (2013.01); *C07D 209/08* (2013.01); *C07D 215/36* (2013.01)

(58) Field of Classification Search
None
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,992,478 A | 2/1991 | Geria | |
| 5,167,649 A | 12/1992 | Zook | |
| 6,960,648 B2 | 11/2005 | Bonny | |
| 2002/0035243 A1 | 3/2002 | Imfeld et al. | |
| 2002/0120100 A1 | 8/2002 | Bonny | |
| 2003/0032594 A1 | 2/2003 | Bonny | |
| 2006/0205736 A1 | 9/2006 | Noble et al. | |
| 2009/0105240 A1* | 4/2009 | Mustelin et al. | 514/231.5 |

(Continued)

FOREIGN PATENT DOCUMENTS

| | | |
|---|---|---|
| EP | 0 470 702 A1 | 2/1992 |
| WO | WO 2004/062664 A1 | 7/2004 |
| WO | WO 2006/128909 A1 | 12/2006 |

OTHER PUBLICATIONS

CA Registry No. 893150-58-8, entered into the Registry File on Jul. 16, 2006, supplied by Aurora Fine Chemicals.*

(Continued)

*Primary Examiner* — Emily Bernhardt
(74) *Attorney, Agent, or Firm* — Saliwanchik, Lloyd & Eisenschenk

(57) ABSTRACT

The subject invention concerns methods and compounds for inhibiting Shp2. In one embodiment, a compound of the invention has a chemical structure as shown in formula I or II:

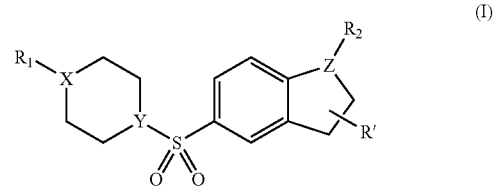

(I)

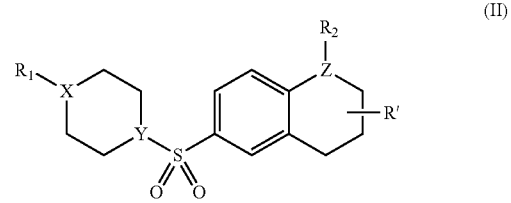

(II)

wherein

X, Y, and Z are independently N or S;

$R_1$ is cycloalkyl, heterocycloalkyl, aryl, or heteroaryl, any of which can be optionally substituted with one or more of halogen; alkyl; heteroalkyl; —COOH; —C($R_3$)$_3$, wherein $R_3$ can independently be any of —H or halogen; or —O$R_4$, wherein $R_4$ can be any of H, alkyl, or heteroalkyl;

$R_2$ is alkyl, alkylcarbonyl, heteroalkylcarbonyl, aryl, arylcarbonyl, heterocycloalkylcarbonyl, cycloalkylcarbonyl, or —C(O)N$R_6$$R_7$, any of which can be optionally substituted with one or more of halogen; alkyl; heteroalkyl; carbonyl; —O$R_4$, wherein $R_4$ can be —H, alkyl, or heteroalkyl; —OH; —C($R_3$)$_3$, wherein $R_3$ can independently be any of —H or halogen; aryl, which can be substituted with one or more of halogen or —O$R_4$; heterocycloalkyl; or —C(O) O$R_5$, wherein $R_5$ can be —H or alkyl;

$R_6$ and $R_7$ are independently —H, alkyl, heteroalkyl, aryl, or heteroaryl; and R' is H or alkyl;

or a pharmaceutically acceptable salt or hydrate thereof.

12 Claims, 1 Drawing Sheet

(56) References Cited

U.S. PATENT DOCUMENTS

2009/0163545 A1* 6/2009 Goldfarb ............... 514/312
2012/0034186 A1* 2/2012 Wu et al. ............... 424/85.5

OTHER PUBLICATIONS

CA Registry No. 901243-41-2, entered into the Registry File on Aug. 14, 2006, supplied by Aurora Fine Chemicals.*
CA Registry No. 901008-92-2, entered into the Registry File on Aug. 13, 2006, supplied by Aurora Fine Chemicals.*
CA Registry Nos. 904437-81-6 and 904447-06-9, entered into the Registry File on Aug. 25, 2006, supplied by Aurora Fine Chemicals.*
CA Registry No. 948658-23-9, entered into the Registry File on Sep. 28, 2007, supplied by Aurora Fine Chemicals.*
CA Registry No. 901042-34-0, entered into the Registry File on Aug. 14, 2006, supplied by Aurora Fine Chemicals.*
CA Registry No. 899717-87-4, entered into the Registry File on Aug. 8, 2006, supplied by Aurora Fine Chemicals.*
Goldfarb, Chemical Abstracts, vol. 151, No. 92840, abstract for US 2009/0163545 (2009).*
CA Registry No. 901034-15-9, entered into the Registry File on Aug. 14, 2006, supplied by Aurora Fine Chemicals.*
CA Registry No. 901033-63-4, entered into the Registry File on Aug. 14, 2006, supplied by Aurora Fine Chemicals.*
CA Registry No. 901032-71-1, entered into the Registry File on Aug. 14, 2006, supplied by Aurora Fine Chemicals.*
CA Registry No. 892754-83-5, entered into the Registry File on Jul. 14, 2006, supplied by Aurora Fine Chemicals.*
CA Registry No. 892751-58-5, entered into the Registry File on Jul. 14, 2006, supplied by Aurora Fine Chemicals.*
CA Registry No. 892750-66-2, entered into the Registry File on Jul. 14, 2006, supplied by Aurora Fine Chemicals.*
Alonso A, Sasin J, Bottini N, Friedberg I, Friedberg I, Osterman A, Godzik A, Hunter T, Dixon J, and Mustelin T (2004) Protein tyrosine phosphatases in the human genome. *Cell* 117:699-711.
Andersen JN, Mortensen OH, Peters GH, Drake PG, Iversen LF, Olsen OH, Jansen PG, Andersen HS, Tonks NK, and Moller NP (2001) Structural and evolutionary relationships among protein tyrosine phosphatase domains. *Mol Cell Biol* 21:7117-7136.
Bennett AM, Hausdorff SF, O'Reilly AM, Freeman RM, and Neel BG (1996) Multiple requirements for SHPTP2 in epidermal growth factor-mediated cell cycle progression. *Mol Cell Biol* 16:1189-1202.
Bentires-Alj M, Paez JG, David FS, Keilhack H, Halmos B, Naoki K, Maris JM, Richardson A, Bardelli A, Sugarbaker DJ, et al. (2004) Activating mutations of the Noonan syndrome-associated SHP2/PTPN11 gene in human solid tumors and adult acute myelogenous leukemia. *Cancer Res* 64:8816-8820.
Bentires-Alj M.; Kontaridis, M. I.; Neel, B. G., Stops along the RAS pathway in human genetic disease. *Nat. Med.* 2006, 12, 283-285.
Bialy L and Waldmann H (2005) Inhibitors of protein tyrosine phosphatases: nextgeneration drugs? *Angew Chem Int Ed Engl* 44:3814-3839.
Bramson, HN. et al., Oxindole-based inhibitors of cyclin-dependent kinase 2 (CDK2): Design, synthesis, enzymatic activities, and X-ray crystallographic analysis. *J. Med. Chem.* 2001, 44, 4339-4358.
Bridges A. J., Chemical inhibitors of protein kinases. *Chem. Rev.* 2001, 101, 2541-2571.
Carroll MP and May WS (1994) Protein kinase C-mediated serine phosphorylation directly activates Raf-1 in murine hematopoietic cells. *J Biol Chem* 269:1249-1256.
Chan, G.; Kalaitzidis, D.; Neel, B. G. The tyrosine phosphatase Shp2 (PTPN11) in cancer. *Cancer Metast. Rev.* 2008, 27, 179-192.
Chan RJ, Leedy MB, Munugalavadla V, Voorhorst CS, Li Y, Yu M, and Kapur R (2005) Human somatic PTPN11 mutations induce hematopoietic-cell hypersensitivity to granulocyte-macrophage colony-stimulating factor. *Blood* 105:3737-3742.
Chen, L. W.; Sung, S. S.; Yip, M. L. R.; Lawrence, H. R.; Ren, Y.; Guida, W. C.; Sebti, S. M.; Lawrence, N. J.; Wu, J., Discovery of a novel Shp2 protein tyrosine phosphatase inhibitor. *Mol. Pharmacol.* 2006, 70, 562-570.
Chu, W.; Zhang, J.; Zeng, C.; Rothfuss, J.; Tu, Z.; Chu, Y.; Reichert, E., D.; Welch, J. M.; Mach, H. R., N-Benzylisatin sulfonamide analogues as potent caspase—3 inhibitors: synthesis, in vitro activity and molecular modeling studies. *J. Med. Chem.*, 2005, 48, 7637-7647.
Cunnick JM, Dorsey JF, Mei L, and Wu J (1998) Reversible regulation of SHP-1 tyrosine phosphatase activity by oxidation. *Biochem Mol Biol Int* 45:887-894.
Cunnick, J. M.; Dorsey, J. F.; Munoz-Antonia, T.; Mei, L.; Wu, J., Requirement of SHP2 binding to Grb2-associated binder-1 for mitogen-activated protein kinase activation in response to lysophosphatidic acid and epidermal growth factor. *J. Biol. Chem.* 2000, 275, 13842-8.
Cunnick JM, Mei L, Doupnik CA, and Wu J (2001) Phosphotyrosines 627 and 659 of Gab1 constitute a bisphosphoryl tyrosine-based activation motif (BTAM) conferring binding and activation of SHP2. *J Biol Chem* 276:24380-24387.
Cunnick JM, Meng S, Ren Y, Desponts C, Wang HG, Djeu JY, and Wu J (2002) Regulation of the mitogen-activated protein kinase signaling pathway by SHP2. *J Biol Chem* 277:9498-9504.
Dance, M.; Montagner, A.; Salles, J.-P.; Yart, A.; Raynal, P. The molecular functions of Shp2 in the Ras/Mitogen-activated protein kinase (ERK1/2) pathway. *Cell. Signalling* 2008, 20, 453-459.
Deb TB, Wong L, Salomon DS, Zhou G, Dixon Je, Gutkind JS, Thompson SA, and Johnson GR (1998) A common requirement for the catalytic activity and both SH2 domains of SHP-2 in mitogen-activated protein (MAP) kinase activation by the ErbB family of receptors. A specific role for SHP-2 in map, but not c-Jun aminoterminal kinase activation. *J Biol Chem* 273:16643-16646.
Fong, T. A. T.; Shawver, L. K.; Sun, L.; Tang, C.; App, H.; Powell, T. J.; Kim, Y. H.; Schreck, R.; Wang, X.; Risau, W.; Ullrich, A.; Hirth, K. P.; McMahon, G., SU5416 is a potent and selective inhibitor of the vascular endothelial growth factor receptor (Flk-1/KDR) that inhibits tyrosine kinase catalysis, tumor vascularization, and growth of multiple tumor types. *Cancer Res.* 1999, 59, 99-106.
Fragale A, Tartaglia M, Wu J, and Gelb BD (2004) Noonan syndrome-associated SHP2/PTPN11 mutants cause EGF-dependent prolonged GAB1 binding and sustained ERK2/MAPK1 activation. *Hum Mutat* 23:267-277.
Friesner RA, Banks JL, Murphy RB, Halgren TA, Klicic JJ, Mainz DT, Repasky MP, Knoll EH, Shelley M, Perry JK, et al. (2004) Glide: a new approach for rapid, accurate docking and scoring. 1. Method and assessment of docking accuracy. *J Med Chem* 47:1739-1749.
Furge, K. A.; Zhang, Y. W.; Vande Woude, G. F., Met receptor tyrosine kinase: enhanced signaling through adapter proteins. *Oncogene* 2000, 19, 5582-9.
Gu H and Neel BG (2003) The "Gab" in signal transduction. *Trends Cell Biol* 13:122-130.
Halgren TA, Murphy RB, Friesner RA, Beard HS, Frye LL, Pollard WT, and Banks JL (2004) Glide: a new approach for rapid, accurate docking and scoring. 2. Enrichment factors in database screening. *J Med Chem* 47:1750-1759.
Higashi, H.; Tsutsumi, R.; Muto, S.; Sugiyama, T.; Azuma, T.; Asaka, M.; Hatakeyama, M., SHP-2 tyrosine phosphatase as an intracellular target of *Helicobacter pylori* CagA protein. *Science* 2002, 295, 683-6.
Hof P, Pluskey S, Dhe-Paganon S, Eck MJ, and Shoelson SE (1998) Crystal structure of the tyrosine phosphatase SHP-2. *Cell* 92:441-450.
Huang P, Ramphal J, Wei J, Liang C, Jallal B, McMahon G, and Tang C (2003) Structure-based design and discovery of novel inhibitors of protein tyrosine phosphatases. *Bioorg Med Chem* 11:1835-1849.
Keilhack H, David FS, McGregor M, Cantley LC, and Neel BG (2005) Diverse biochemical properties of Shp2 mutants. Implications for disease phenotypes. *J Biol Chem* 280:30984-30993.
Kolch W, Heidecker G, Kochs G, Hummel R, Vahidi H, Mischak H, Finkenzeller G, Marme D, and Rapp UR (1993) Protein kinase C alpha activates RAF-1 by direct phosphorylation. *Nature (Lond)* 364:249-252.
Kratz CP, Niemeyer CM, Castleberry RP, Cetin M, Bergstrasser E, Emanuel PD, Hasle H, Kardos G, Klein C, Kojima S, et al. (2005) The mutational spectrum of PTPN11 in juvenile myelomonocytic leukemia and Noonan syndrome/myeloproliferative disease. *Blood* 106:2183-2185.

(56) References Cited

OTHER PUBLICATIONS

Lazo JS, Nemoto K, Pestell KE, Cooley K, Southwick EC, Mitchell DA, Furey W, Gussio R, Zaharevitz DW, Joo B, et al. (2002) Identification of a potent and selective pharmacophore for Cdc25 dual specificity phosphatase inhibitors. *Mol Pharmacol* 61:720-728.

Lee, D.; Long, S. A.; Murray, J. H.; Adams, J. L.; Nuttall, M. E.; Nadeau, D. P.; Kikly, K.; Winkler, J. D.; Sung, C. M.; Ryan, M. D.; Levy, M. A.; Keller, P. M.; DeWolf, W. E., Potent and selective nonpeptide inhibitors of Caspases 3 and 7. *J. Med. Chem.* 2001, 44, 2015-2026.

Maroun CR, Naujokas MA, Holgado-Madruga M, Wong AJ, and Park M (2000) The tyrosine phosphatase SHP-2 is required for sustained activation of extracellular signal-regulated kinase and epithelial morphogenesis downstream from the met receptor tyrosine kinase. *Mol Cell Biol* 20:8513-8525.

McCain DF, Wu L, Nickel P, Kassack MU, Kreimeyer A, Gagliardi A, Collins DC, and Zhang ZY (2004) Suramin derivatives as inhibitors and activators of proteintyrosine phosphatases. *J Biol Chem* 279:14713-14725.

Meyer-Ter-Venn, T.; Covacci, A.; Kist, M.; Pahl, H. L., *Helicobacter pylori* activates mitogenactivated protein kinase cascades and induces expression of the proto-oncogenes c-fos and c-jun. *J. Biol. Chem.* 2000, 275, 16064-72.

Mohi MG, Williams IR, Dearolf CR, Chan G, Kutok JL, Cohen S, Morgan K, Boulton C, Shigematsu H, Keilhack H, et al. (2005) Prognostic, therapeutic, and mechanistic implications of a mouse model of leukemia evoked by Shp2 (PTPN11) mutations. *Cancer Cell* 7:179-191.

Neel, B. G.; Tonks, N. K., Protein tyrosine phosphatases in signal transduction. *Curr. Opin. Cell Biol.* 1997, 9, 193-204.

Neel BG, Gu H, and Pao L (2003) The 'Shp'ing news: SH2 domain-containing tyrosine phosphatases in cell signaling. *Trends Biochem Sci* 28:284-293.

Nishida K and Hirano T (2003) The role of Gab family scaffolding adapter proteins in the signal transduction of cytokine and growth factor receptors. *Cancer Sci* 94:1029-1033.

Noren-Muller, A.; Reis-Correa, I.; Prinz, H.; Rosenbaum, C.; Saxena, K.; Schwalbe, H. J.; Vestweber, D.; Cagna, G.; Schunk, S.; Schwarz, O.; Schiewe, H.; Waldmann, H., Discovery of protein phosphatase inhibitor classes by biology-oriented synthesis. *Proc. Nat. Acad. Sci. USA* 2006, 103, 10606-10611.

Oka T, Ouchida M, Koyama M, Ogama Y, Takada S, Nakatani Y, Tanaka T, Yoshino T, Hayashi K, Ohara N, et al. (2002) Gene silencing of the tyrosine phosphatase SHP1 gene by aberrant methylation in leukemias/lymphomas. *Cancer Res* 62: 6390-6394.

O'Reilly AM and Neel BG (1998) Structural determinants of SHP-2 function and specificity in *Xenopus* mesoderm induction. *Mol Cell Biol* 18:161-177.

Parrick, J.; Yahya, A.; Ijaz, A. S.; Yizun, J. Convenient preparation of 3,3-dibromo-1,3-dihydroindol-2-ones and indole-2,3-diones (isatins) from indoles. *J. Chem. Soc., Perkin Trans. 1* 1989, 2009-2015.

Poole, A. W.; Jones, M. L., A SHPing tale: Perspectives on the regulation of SHP-1 and SHP-2 tyrosine phosphatases by the C-terminal tail. *Cell. Signalling* 2005, 17, 1323-1332.

Ren Y, Meng S, Mei L, Zhao ZJ, Jove R, and Wu J (2004) Roles of Gab1 and SHP2 in paxillin tyrosine dephosphorylation and Src activation in response to epidermal growth factor. *J Biol Chem* 279:8497-8505.

Schubbert S, Lieuw K, Rowe SL, Lee CM, Li X, Loh ML, Clapp DW, and Shannon KM (2005) Functional analysis of leukemia-associated PTPN11 mutations in primary hematopoietic cells. *Blood* 106:311-317.

Shen K, Keng YF, Wu L, Guo Xl, Lawrence DS, and Zhang ZY (2001) Acquisition of a specific and potent PTP1B inhibitor from a novel combinatorial library and screening procedure. *J Biol Chem* 276:47311-47319.

Somasekhara, S.; Dighe, V. S.; Suthar, G. K.; Mukherjee, S. L. Chlorosulfonation of isatins. *Curr. Sci.* 1965, 34, 508.

Stein CA (1993) Suramin: a novel antineoplastic agent with multiple potential mechanisms of action. *Cancer Res* 53 (10 Suppl):2239-2248.

Sun, L.; Tran, N.; Liang, C.; Tang, F.; Rice, A.; Schreck, R.; Waltz, K.; Shawver, L. K.; McMahon, G.; Tang, C., Design, synthesis, and evaluations of substituted 3-[(3-or 4-carboxyethylpyrrol-2-yl)methylidenyl]indolin-2-ones as inhibitors of VEGF, FGF, and PDGF receptor tyrosine kinases. *J. Med. Chem.* 1999, 42, 5120-5130.

Tartaglia M and Gelb BD (2005) Germ-line and somatic PTPN11 mutations in human disease. *Eur J Med Genet* 48:81-96.

Tartaglia M, Niemeyer CM, Fragale A, Song X, Buechner J, Jung A, Hahlen K, Hasle H, Licht JD, and Gelb BD (2003) Somatic mutations in PTPN11 in juvenile myelomonocytic leukemia, myelodysplastic syndromes and acute myeloid leukemia. *Nat Genet* 34:148-150.

Tenev, T.; Keilhack, H.; Tomic, S.; Stoyanov, B.; Stein-Gerlach, M.; Lammers, R.; Krivtsov, A. V.; Ullrich, A.; Bohmer, F. D., Both SH2 domains are involved in interaction of SHP-1 with the epidermal growth factor receptor but cannot confer receptor-directed activity to SHP-1/SHP-2 chimera. *J. Biol. Chem.* 1997, 272, 5966-73.

Yamauchi K, Milarski KL, Saltiel AR, and Pessin JE (1995) Protein-tyrosinephosphatase SHPTP2 is a required positive effector for insulin downstream signaling. *Proc Natl Acad Sci USA* 92:664-668.

Yang J, Liang X, Niu T, Meng W, Zhao Z, and Zhou GW (1998) Crystal structure of the catalytic domain of protein-tyrosine phosphatase SHP-1. *J Biol Chem* 273: 28199-28207.

Yang J, Liu L, He D, Song X, Liang X, Zhao ZJ, and Zhou GW (2003) Crystal structure of human protein-tyrosine phosphatase SHP-1. *J Biol Chem* 278:6516-6520.

Yang, J.; Cheng, Z.; Niu, T.; Liang, X.; Zhao, Z. J.; Zhou, G. W., Structural basis for substrate specificity of protein-tyrosine phosphatase SHP-1. *J. Biol. Chem.* 2000, 275, 4066-4071.

Zhang ZY (2002) Protein tyrosine phosphatases: structure and function, substrate specificity, and inhibitor development. *Annu Rev Pharmacol Toxicol* 42:209-234.

Hatakeyama M (2004) Oncogenic mechanisms of the *Helicobacter pylori* CagA protein. *Nat Rev Cancer* 4:688-694.

* cited by examiner

CDL 4340-0580
IC$_{50}$ (Shp2) : 2.2 μM

NAT6-297775
IC$_{50}$ (Shp2) : 2.5 μM

XW2-011B: IC$_{50}$ 47.8 μM

INDOLINE SCAFFOLD SHP-2 INHIBITORS AND CANCER TREATMENT METHOD

CROSS-REFERENCE TO RELATED APPLICATIONS

The present application is the National Stage of International Application Number PCT/US2009/051276, filed Jul. 21, 2009, which claims the benefit of U.S. Provisional Application Ser. Nos. 61/082,382, filed Jul. 21, 2008 and 61/170,354, filed Apr. 17, 2009, each of which is hereby incorporated by reference herein in its entirety, including any figures, tables, nucleic acid sequences, amino acid sequences, and drawings.

GOVERNMENT SUPPORT

This invention was made with government support under grant numbers CA118210 and CA077467 awarded by the National Institutes of Health. The government has certain rights in the invention.

BACKGROUND OF THE INVENTION

Tyrosyl phosphorylation is a mechanism involving in regulation of human cellular processes from cell differentiation and growth to apoptosis. The process of tyrosyl phosphorylation is regulated by protein-tyrosine phosphatases (PTP) and protein-tyrosine kinases (PTK). When this regulation is disrupted, diseases such as cancer can arise (Mohi and Neel, 2007). Although there is more research on PTKs since the first PTK was discovered about 10 years earlier than the first PTP, recent studies have found that PTPs have a prominent role in regulation of tyrosyl phosphorylation in the cells (Alonso et al., 2004).

Shp2, encoded by the PTPN11 gene, is found to be mutated in several types of leukemias (Mohi and Neel, 2007). Furthermore, the wildtype Shp2 mediates cell signaling of many protein tyrosine kinase oncogenes such as ErbB and Met. Shp2 is necessary for embryonic development and for growth factor, cytokine, and extra-cellular matrix signaling (Salmond and Alexander, 2006) and is involved in regulation of cell proliferation, differentiation, and migration. Shp2 mutations are linked to Noonan syndrome, juvenile myelomonocytic leukemia, acute myelogenous leukemia, and LEOPARD (lentigines, electrocardiogram abnormalities, ocular hypertelorism, pulmonic valvular stenosis, abnormalities of genitalia, retardation of growth, and deafness) syndrome.

Within these diseases, Shp2 is activated and interacts with the Gab family of docking proteins. This interaction activates a pathway leading to cell proliferation and tumorigenesis. The identification of Shp2's role in these diseases is very important for developing cancer therapy. Targeting and inhibiting Shp2 with small molecule inhibitors has become a major goal in developing a new cancer therapy.

Currently, there are a few known inhibitors of Shp2. Two of these compounds are CDL 4340-0580 (Hellmuth et al., 2008) and NAT6-297775, seen in FIGS. 1A and 1B (Noren-Muller et al., 2006). Although these compounds have the ability to inhibit Shp2, they also inhibit tumor suppressor Shp1, which is not the cause of these malignancies. Ultimately, a Shp2 inhibitor should only affect Shp2 and not other important cellular processes.

BRIEF SUMMARY OF THE INVENTION

The subject invention concerns methods and compounds for inhibiting Shp2. In one embodiment, a compound of the invention has a chemical structure as shown in formula I or II:

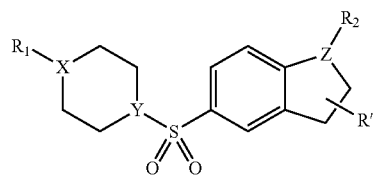

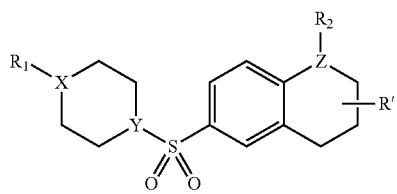

wherein
X, Y, and Z are independently N or S;
$R_1$ is cycloalkyl, heterocycloalkyl, aryl, or heteroaryl, any of which can be optionally substituted with one or more of halogen; alkyl; heteroalkyl; —COOH; —C($R_3$)$_3$, wherein $R_3$ can independently be any of —H or halogen; or —O$R_4$, wherein $R_4$ can be any of H, alkyl, or heteroalkyl;
$R_2$ is alkyl, alkylcarbonyl, heteroalkylcarbonyl, aryl, arylcarbonyl, heterocycloalkylcarbonyl, cycloalkylcarbonyl, or —C(O)NR$_6$R$_7$, any of which can be optionally substituted with one or more of halogen; alkyl; heteroalkyl; carbonyl; —O$R_4$, wherein $R_4$ can be —H, alkyl, or heteroalkyl; —OH; —C($R_3$)$_3$, wherein $R_3$ can independently be any of —H or halogen; aryl, which can be substituted with one or more of halogen or —O$R_4$; heterocycloalkyl; or —C(O)O$R_5$, wherein $R_5$ can be —H or alkyl;
$R_6$ and $R_7$ are independently —H, alkyl, heteroalkyl, aryl, or heteroaryl; and
R' is H or alkyl;
or a pharmaceutically acceptable salt or hydrate thereof.

The subject invention also concerns methods for treating oncological disorders in a patient. In one embodiment, an effective amount of one or more compounds or compositions of the present invention is administered to a patient having an oncological disorder and who is in need of treatment thereof.

DETAILED DESCRIPTION OF THE INVENTION

Figure 1A:
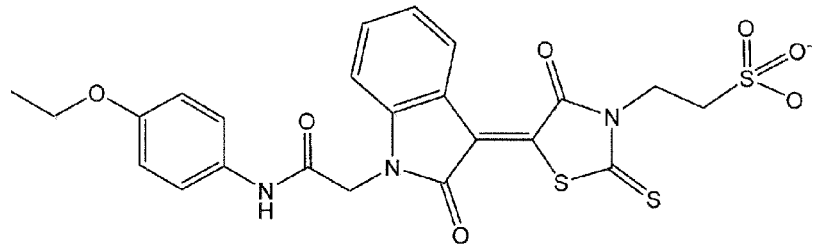
FIGS. 1A and 1B are chemical diagrams of non-selective inhibitors of Shp2.
Figure 1B:
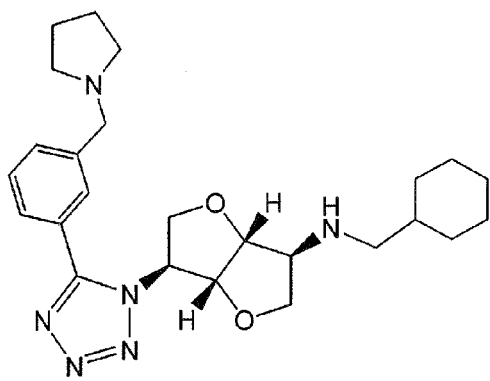

The subject invention concerns methods and compounds for inhibiting Shp2. In one embodiment, a compound of the invention has a chemical structure as shown in formula I or II:

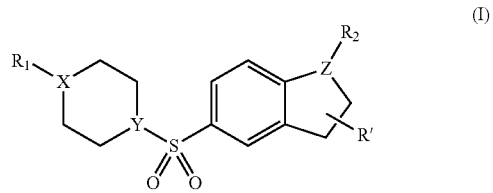

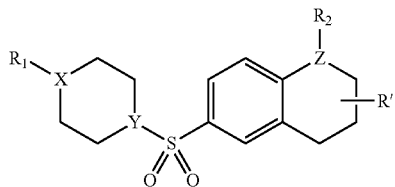

(II)

wherein

X, Y, and Z are independently N or S;

R₁ is cycloalkyl, heterocycloalkyl, aryl, or heteroaryl, any of which can be optionally substituted with one or more of halogen; alkyl; heteroalkyl; —COOH; —C(R₃)₃, wherein R₃ can independently be any of —H or halogen; or —OR₄, wherein R₄ can be any of H, alkyl, or heteroalkyl;

R₂ is alkyl, alkylcarbonyl, heteroalkylcarbonyl, aryl, arylcarbonyl, heterocycloalkylcarbonyl, cycloalkylcarbonyl, or —C(O)NR₆R₇, any of which can be optionally substituted with one or more of halogen; alkyl; heteroalkyl; carbonyl; —OR₄, wherein R₄ can be —H, alkyl, or heteroalkyl; —OH; —C(R₃)₃, wherein R₃ can independently be any of —H or halogen; aryl, which can be substituted with one or more of halogen or —OR₄; heterocycloalkyl; or —C(O)OR₅, wherein R₅ can be —H or alkyl;

R₆ and R₇ are independently —H, alkyl, heteroalkyl, aryl, or heteroaryl; and

R' is H or alkyl;

or a pharmaceutically acceptable salt or hydrate thereof.

In one embodiment, a compound of formula I has the structure:

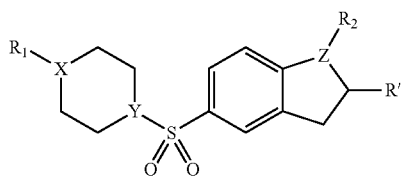

In an exemplified embodiment, X, Y, and Z are all N.

In one embodiment, R₁ is aryl optionally substituted with one or more of —Cl, —F, —COOH, —CH₃, CF₃, or —OCH₃.

In a further embodiment, R₁ is phenyl optionally substituted with one or more of —Cl, —F, —COOH, —CH₃, CF₃, or —OCH₃.

In one embodiment, —OR₄ is —OCH₃ or —OCH₂CH₃.

In a specific embodiment, R₁ has a structure selected from:

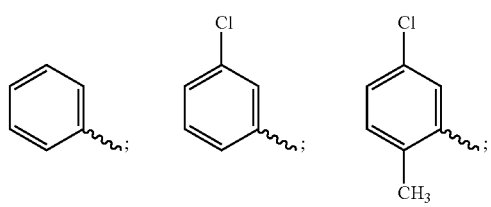

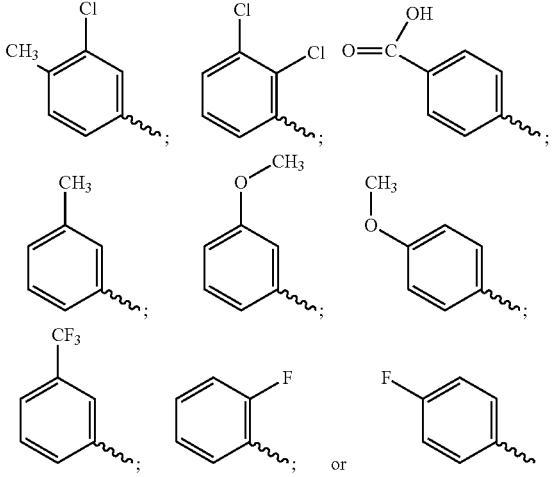

wherein indicates the point of attachment.

In one embodiment, R₂ is alkylcarbonyl optionally substituted with one or more of —OH, —COOH, aryl, or —OR, wherein R is —H or alkyl.

In one embodiment, R₂ is —C(O)NHR₆, wherein R₆ can be alkyl or aryl, any of which can be optionally substituted with one or more of halogen; carbonyl; —OR₄, wherein R₄ can be —H or alkyl; —OH; —C(R₃)₃, wherein R₃ can independently be any of —H or halogen; aryl, which can be substituted with one or more of halogen or —OR₄; or —C(O)OR₅, wherein R₅ can be —H or alkyl;

In a specific embodiment, R₂ has a structure selected from:

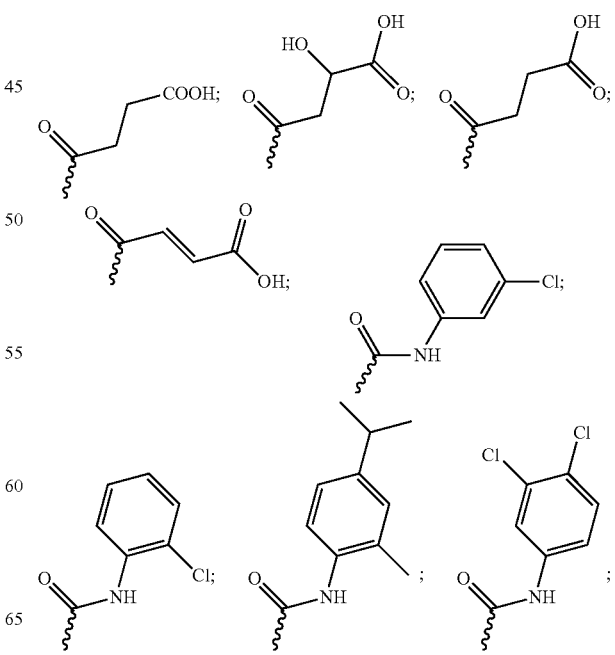

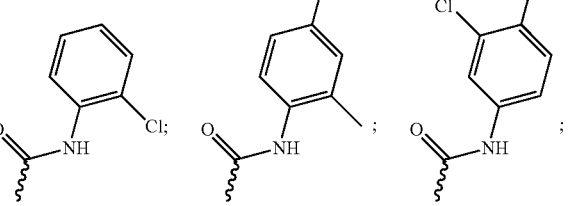

-continued
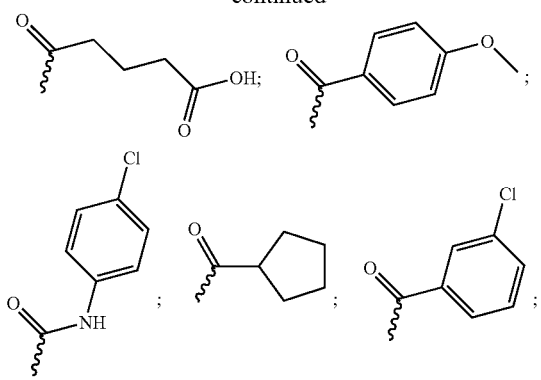
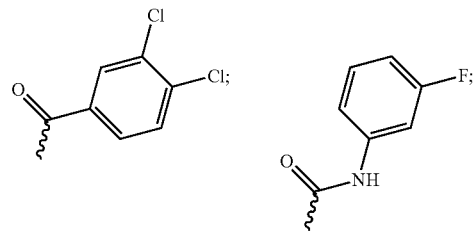
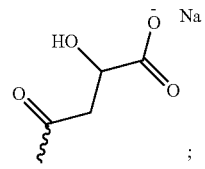
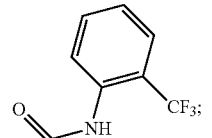
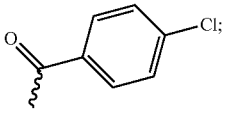
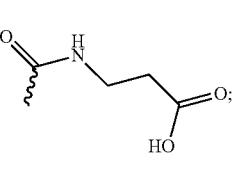
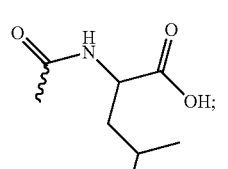
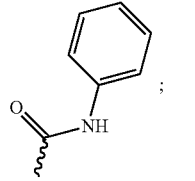
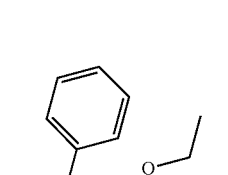
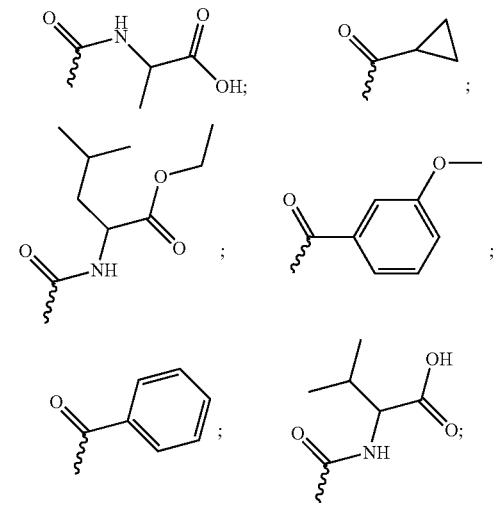

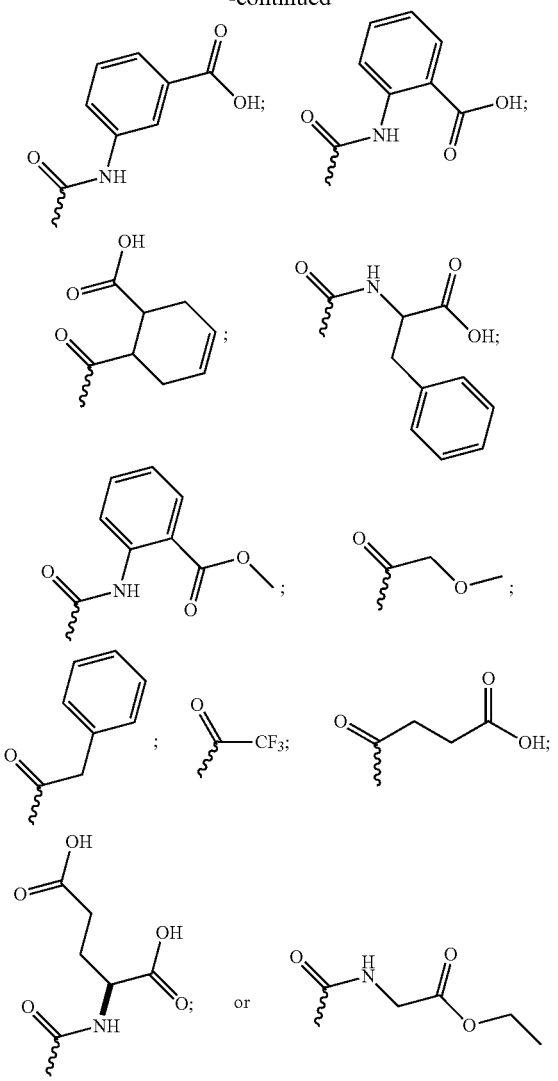

wherein $\xi$ indicates the point of attachment.

Exemplified embodiments of compounds of the invention are shown in Table 3.

As used herein, alkyl means straight or branched chain, saturated or mono- or polyunsaturated hydrocarbon groups having from 1 to 20 carbon atoms and $C_{1-X}$ alkyl means straight or branched chain alkyl groups containing from one up to X carbon atoms. For example, $C_{1-6}$ alkyl means straight or branched chain alkyl groups containing from one up to 6 carbon atoms. Alkoxy means an alkyl-O— group in which the alkyl group is as previously described. Cycloalkyl includes a nonaromatic monocyclic or multicyclic ring system, including fused and spiro rings, of from about three to about 10 carbon atoms. A cyclic alkyl may optionally be partially unsaturated. Cycloalkoxy means a cycloalkyl-O— group in which cycloalkyl is as defined herein. Aryl means an aromatic monocyclic or multicyclic carbocyclic ring system, including fused and spiro rings, containing from about six to about 14 carbon atoms. Aryloxy means an aryl-O— group in which the aryl group is as described herein. Alkylcarbonyl means a RC(O)— group where R is an alkyl group as previously described. Alkoxycarbonyl means an ROC(O)— group where R is an alkyl group as previously described. Cycloalkylcarbonyl means an RC(O)— group where R is a cycloalkyl group as previously described. Cycloalkoxycarbonyl means an ROC(O)— group where R is a cycloalkyl group as previously described.

Heteroalkyl means a straight or branched-chain having from one to 20 carbon atoms and one or more heteroatoms selected from nitrogen, oxygen, or sulphur, wherein the nitrogen and sulphur atoms may optionally be oxidized, i.e., in the form of an N-oxide or an S-oxide. Heteroalkylcarbonyl means an RC(O)— group where R is a heteroalkyl group as previously described. Heterocycloalkyl means a monocyclic or multicyclic ring system (which may be saturated or partially unsaturated), including fused and spiro rings, of about five to about 10 elements wherein one or more of the elements in the ring system is an element other than carbon and is selected from nitrogen, oxygen, silicon, or sulphur atoms. Heteroaryl means a five to about a 14-membered aromatic monocyclic or multicyclic hydrocarbon ring system, including fused and spiro rings, in which one or more of the elements in the ring system is an element other than carbon and is selected from nitrogen, oxygen, silicon, or sulphur and wherein an N atom may be in the form of an N-oxide. Arylcarbonyl means an aryl-C(O)— group in which the aryl group is as described herein. Heteroarylcarbonyl means a heteroaryl-C(O)— group in which the heteroaryl group is as described herein and heterocycloalkylcarbonyl means a heterocycloalkyl-C(O)— group in which the heterocycloalkyl group is as described herein. Aryloxycarbonyl means an ROC(O)— group where R is an aryl group as previously described. Heteroaryloxycarbonyl means an ROC(O)— group where R is a heteroaryl group as previously described. Heteroaryloxy means a heteroaryl-O— group in which the heteroaryl group is as previously described. Heterocycloalkoxy means a heterocycloalkyl-O— group in which the heterocycloalkyl group is as previously described. Heterocycloalkoxycarbonyl means an ROC(O)— group where R is a heterocycloalkyl group as previously described.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propynyl, 2-isopentenyl, 2-butadienyl, ethynyl, 1-propynyl, 3-propynyl, and 3-butynyl. Cycloalkyl groups include, for example, cyclopropyl, cyclobutyl, cyclopentyl, cyclohexyl, 1-cyclohexenyl, 3-cyclohexenyl, and cycloheptyl. Heterocycloalkyl groups include, for example, 1-piperidinyl, 2-piperidinyl, 3-piperidinyl, 3-morpholinyl, 4-morpholinyl, tetrahydrofuran-2-yl, tetrahydrofuran-3-yl, tetrahydrothien-2-yl, tetrahydrothien-3-yl, 1-piperazinyl, 2-piperazinyl, and 1,4-diazabicyclooctane. Aryl groups include, for example, phenyl, indenyl, biphenyl, 1-naphthyl, 2-naphthyl, anthracenyl, and phenanthracenyl. Heteroaryl groups include, for example, 1-pyrrolyl, 2-pyrrolyl, 3-pyrrolyl, furyl, thienyl, imidazolyl, oxazolyl, thiazolyl, pyrazolyl, pyridyl, indolyl, quinolinyl, isoquinolinyl, benzoquinolinyl, carbazolyl, and diazaphenanthrenyl.

As used herein, halogen means the elements fluorine (F), chlorine (Cl), Bromine (Br), and iodine (I).

Compounds of the subject invention also include physiologically-acceptable salts and hydrates of the subject compounds. Physiologically-acceptable salts include salts of the compounds of the invention which are prepared with acids or bases, depending on the particular substituents found on the subject complexes described herein. Examples of physiologically-acceptable base addition salts include sodium, potassium, calcium, ammonium, or magnesium salt. Examples of physiologically-acceptable acid addition salts include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Physiologically-acceptable salts of compounds of the invention can be prepared using conventional techniques.

It will be appreciated by those skilled in the art that certain of the compounds of the invention may contain one or more asymmetrically substituted carbon atoms which can give rise to stereoisomers. It is understood that the invention extends to all such stereoisomers, including enantiomers, and diastereoisomers and mixtures, including racemic mixtures thereof.

In vivo application of the subject compounds, and compositions containing them, can be accomplished by any suitable method and technique presently or prospectively known to those skilled in the art. The subject compounds can be formulated in a physiologically- or pharmaceutically-acceptable form and administered by any suitable route known in the art including, for example, oral, nasal, rectal, and parenteral routes of administration. As used herein, the teen parenteral includes subcutaneous, intradermal, intravenous, intramuscular, intraperitoneal, and intrasternal administration, such as by injection. Administration of the subject compounds of the invention can be a single administration, or at continuous or distinct intervals as can be readily determined by a person skilled in the art.

The compounds of the subject invention, and compositions comprising them, can also be administered utilizing liposome technology, slow release capsules, implantable pumps, and biodegradable containers. These delivery methods can, advantageously, provide a uniform dosage over an extended period of time. The compounds of the invention can also be administered in their salt derivative forms or crystalline forms.

Compounds of the subject invention can be formulated according to known methods for preparing physiologically acceptable compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the compound is combined with a suitable carrier in order to facilitate effective administration of the composition. The compositions used in the present methods can also be in a variety of for ins. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional physiologically-acceptable carriers and diluents which are known to those skilled in the art. Examples of carriers or diluents for use with the subject compounds include ethanol, dimethyl sulfoxide, glycerol, alumina, starch, saline, and equivalent carriers and diluents. To provide for the administration of such dosages for the desired therapeutic treatment, compositions of the invention will advantageously comprise between about 0.1% and 99%, and especially, 1 and 15% by weight of the total of one or more of the subject compounds based on the weight of the total composition including carrier or diluent.

The subject invention also concerns methods for treating a person or animal having a disorder or condition associated with aberrant or excessive Shp2 activity, or a mutation in Shp2, in a cell, wherein a therapeutically effective amount of one or more compounds or compositions of the invention is administered to the person or animal. In one embodiment, the disorder or condition is an oncological disorder or condition. In another embodiment, the disorder or condition is Noonan syndrome or LEOPARD syndrome. In one embodiment, the compound is a compound shown in Table 3. In a specific embodiment, the compound is the compound designated herein as JHE-02-032A or JHE-02-032B. In another embodiment, the compound is the compound designated herein as XW2-011B. In a further embodiment, the compound is the compound designated herein as JHE-02-035A.

The subject invention also concerns methods for inhibiting Shp2 enzymatic activity in a cell. In one embodiment, a cell is contacted with an effective amount of one or more inhibitor compounds or compositions of this invention. In one embodiment, the compound is a compound shown in Table 3. In a specific embodiment, the compound is the compound designated herein as JHE-02-032A or JHE-02-032B. In another embodiment, the compound is the compound designated herein as XW2-011B. In a further embodiment, the compound is the compound designated herein as JHE-02-035A. Cells can be any mammalian cell, such as a human cell, canine cell, feline cell, or equine cell. In one embodiment the cell is a tumor cell, a cancer cell or a transformed cell.

The subject invention also concerns a packaged dosage formulation comprising in one or more containers at least one inhibitor compound or composition of the invention. In one embodiment, the compound is a compound shown in Table 3. In one embodiment, a packaged dosage formulation comprises a compound designated herein as JHE-02-032A or JHE-02-032B. In another embodiment, the compound is the compound designated herein as XW2-011B. In a further embodiment, the compound is the compound designated herein as JHE-02-035A. A packaged dosage formulation can optionally comprise in one or more containers a pharmaceutically acceptable carrier or diluent.

Compounds of the invention, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions of the invention to a cell comprises attaching the compounds to a protein or nucleic acid that is targeted for delivery to the target cell. U.S. Pat. No. 6,960,648 and Published U.S. Patent Application Nos. 20030032594 and 20020120100 disclose amino acid sequences that can be coupled to another composition and that allows the composition to be translocated across biological membranes. Published U.S. Patent Application No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

The subject invention also concerns methods for treating oncological disorders in a patient. In one embodiment, an effective amount of one or more compounds or compositions of the present invention is administered to a patient having an oncological disorder and who is in need of treatment thereof. Methods of the invention can optionally include identifying a patient who is or may be in need of treatment of an oncological disorder. The patient can be a human or other mammal, such as a primate (monkey, chimpanzee, ape, etc.), dog, cat, cow, pig, or horse, or other animals having an oncological disorder. Means for administering and formulating compounds for administration to a patient are known in the art, examples of which are described herein. Oncological disorders within the scope of the invention include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment with the present invention include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, myelomonocytic, and other), and lymphoma (Hodgkin's and non-Hodgkin's), and multiple myeloma.

Examples of cancers that can be treated according to the present invention are listed in Table 1.

TABLE 1

Examples of Cancer Types

| | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult (Primary) |
| Acute Myeloid Leukemia, Adult | |
| Acute Myeloid Leukemia, Childhood | Hepatocellular (Liver) Cancer, Childhood (Primary) |
| Adrenocortical Carcinoma | |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |
| Astrocytoma, Childhood Cerebellar | Hypothalamic and Visual Pathway Glioma, Childhood |
| Astrocytoma, Childhood Cerebral | |
| Basal Cell Carcinoma | Intraocular Melanoma |
| Bile Duct Cancer, Extrahepatic | Islet Cell Carcinoma (Endocrine Pancreas) |
| Bladder Cancer | Kaposi's Sarcoma |
| Bladder Cancer, Childhood | Kidney (Renal Cell) Cancer |
| Bone Cancer, Osteosarcoma/Malignant Fibrous Histiocytoma | Kidney Cancer, Childhood |
| | Laryngeal Cancer |
| Brain Stem Glioma, Childhood | Laryngeal Cancer, Childhood |
| Brain Tumor, Adult | Leukemia, Acute Lymphoblastic, Adult |
| Brain Tumor, Brain Stem Glioma, Childhood | Leukemia, Acute Lymphoblastic, Childhood |
| | Leukemia, Acute Myeloid, Adult |
| Brain Tumor, Cerebellar Astrocytoma, Childhood | Leukemia, Acute Myeloid, Childhood |
| | Leukemia, Chronic Lymphocytic |
| Brain Tumor, Cerebral Astrocytoma/Malignant Glioma, Childhood | Leukemia, Chronic Myelogenous |
| | Leukemia, Hairy Cell |
| | Lip and Oral Cavity Cancer |
| Brain Tumor, Ependymoma, Childhood | Liver Cancer, Adult (Primary) |
| Brain Tumor, Medulloblastoma, Childhood | Liver Cancer, Childhood (Primary) |
| | Lung Cancer, Non-Small Cell |
| Brain Tumor, Supratentorial Primitive Neuroectodermal Tumors, Childhood | Lung Cancer, Small Cell |
| | Lymphoma, AIDS-Related |
| Brain Tumor, Visual Pathway and Hypothalamic Glioma, Childhood | Lymphoma, Burkitt's |
| | Lymphoma, Cutaneous T-Cell, see Mycosis Fungoides and Sézary Syndrome |
| Brain Tumor, Childhood | Lymphoma, Hodgkin's, Adult |
| Breast Cancer | Lymphoma, Hodgkin's, Childhood |
| Breast Cancer, Childhood | Lymphoma, Hodgkin's During Pregnancy |
| Breast Cancer, Male | Lymphoma, Non-Hodgkin's, Adult |
| Bronchial Adenomas/Carcinoids, Childhood | Lymphoma, Non-Hodgkin's, Childhood |
| | Lymphoma, Non-Hodgkin's During Pregnancy |
| Burkitt's Lymphoma | |
| Carcinoid Tumor, Childhood | |
| Carcinoid Tumor, Gastrointestinal | Lymphoma, Primary Central Nervous System |
| Carcinoma of Unknown Primary | Macroglobulinemia, Waldenström's |
| Central Nervous System Lymphoma, Primary | Malignant Fibrous Histiocytoma of Bone/Osteosarcoma |
| Cerebellar Astrocytoma, Childhood | Medulloblastoma, Childhood |
| Cerebral Astrocytoma/Malignant Glioma, Childhood | Melanoma |
| | Melanoma, Intraocular (Eye) |
| Cervical Cancer | Merkel Cell Carcinoma |
| Childhood Cancers | Mesothelioma, Adult Malignant |
| Chronic Lymphocytic Leukemia | Mesothelioma, Childhood |
| Chronic Myelogenous Leukemia | Metastatic Squamous Neck Cancer with Occult Primary |
| Chronic Myeloproliferative Disorders | |
| Colon Cancer | Multiple Endocrine Neoplasia Syndrome, Childhood |
| Colorectal Cancer, Childhood | |
| Cutaneous T-Cell Lymphoma, see Mycosis Fungoides and Sézary Syndrome | Multiple Myeloma/Plasma Cell Neoplasm |
| | Mycosis Fungoides |
| | Myelodysplastic Syndromes |
| Endometrial Cancer | Myelodysplastic/Myeloproliferative Diseases |

TABLE 1-continued

Examples of Cancer Types

| | |
|---|---|
| Ependymoma, Childhood | Myelogenous Leukemia, Chronic |
| Esophageal Cancer | Myeloid Leukemia, Adult Acute |
| Esophageal Cancer, Childhood | Myeloid Leukemia, Childhood Acute |
| Ewing's Family of Tumors | Myeloma, Multiple |
| Extracranial Germ Cell Tumor, Childhood | Myeloproliferative Disorders, Chronic |
| | Nasal Cavity and Paranasal Sinus Cancer |
| Extragonadal Germ Cell Tumor | Nasopharyngeal Cancer |
| Extrahepatic Bile Duct Cancer | Nasopharyngeal Cancer, Childhood |
| Eye Cancer, Intraocular Melanoma | Neuroblastoma |
| Eye Cancer, Retinoblastoma | Non-Hodgkin's Lymphoma, Adult |
| Gallbladder Cancer | Non-Hodgkin's Lymphoma, Childhood |
| Gastric (Stomach) Cancer | Non-Hodgkin's Lymphoma During Pregnancy |
| Gastric (Stomach) Cancer, Childhood | Non-Small Cell Lung Cancer |
| Gastrointestinal Carcinoid Tumor | Oral Cancer, Childhood |
| Germ Cell Tumor, Extracranial, Childhood | Oral Cavity Cancer, Lip and Oropharyngeal Cancer |
| Germ Cell Tumor, Extragonadal | Osteosarcoma/Malignant Fibrous Histiocytoma of Bone |
| Germ Cell Tumor, Ovarian | |
| Gestational Trophoblastic Tumor | Ovarian Cancer, Childhood |
| Glioma, Adult | Ovarian Epithelial Cancer |
| Glioma, Childhood Brain Stem | Ovarian Germ Cell Tumor |
| Glioma, Childhood Cerebral Astrocytoma | Ovarian Low Malignant Potential Tumor |
| | Pancreatic Cancer |
| Glioma, Childhood Visual Pathway and Hypothalamic | Pancreatic Cancer, Childhood |
| | Pancreatic Cancer, Islet Cell |
| Skin Cancer (Melanoma) | Paranasal Sinus and Nasal Cavity Cancer |
| Skin Carcinoma, Merkel Cell | Parathyroid Cancer |
| Small Cell Lung Cancer | Penile Cancer |
| Small Intestine Cancer | Pheochromocytoma |
| Soft Tissue Sarcoma, Adult | Pineoblastoma and Supratentorial Primitive Neuroectodermal Tumors, Childhood |
| Soft Tissue Sarcoma, Childhood | |
| Squamous Cell Carcinoma, see Skin Cancer (non-Melanoma) | Pituitary Tumor |
| | Plasma Cell Neoplasm/Multiple Myeloma |
| Squamous Neck Cancer with Occult Primary, Metastatic | Pleuropulmonary Blastoma |
| | Pregnancy and Breast Cancer |
| Stomach (Gastric) Cancer | Pregnancy and Hodgkin's Lymphoma |
| Stomach (Gastric) Cancer, Childhood | Pregnancy and Non-Hodgkin's Lymphoma |
| Supratentorial Primitive Neuroectodermal Tumors, Childhood | Primary Central Nervous System Lymphoma |
| | Prostate Cancer |
| T-Cell Lymphoma, Cutaneous, see Mycosis Fungoides and Sézary Syndrome | Rectal Cancer |
| | Renal Cell (Kidney) Cancer |
| | Renal Cell (Kidney) Cancer, Childhood |
| Testicular Cancer | Renal Pelvis and Ureter, Transitional Cell Cancer |
| Thymoma, Childhood | |
| Thymoma and Thymic Carcinoma | Retinoblastoma |
| Thyroid Cancer | Rhabdomyosarcoma, Childhood |
| Thyroid Cancer, Childhood | Salivary Gland Cancer |
| Transitional Cell Cancer of the Renal Pelvis and Ureter | Salivary Gland Cancer, Childhood |
| | Sarcoma, Ewing's Family of Tumors |
| Trophoblastic Tumor, Gestational | Sarcoma, Kaposi's |
| Unknown Primary Site, Carcinoma of, Adult | Sarcoma, Soft Tissue, Adult |
| | Sarcoma, Soft Tissue, Childhood |
| Unknown Primary Site, Cancer of, Childhood | Sarcoma, Uterine |
| | Sezary Syndrome |
| Unusual Cancers of Childhood | Skin Cancer (non-Melanoma) |
| Ureter and Renal Pelvis, Transitional Cell Cancer | Skin Cancer, Childhood |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

In a specific embodiment, the oncological disorder is a leukemia.

For the treatment of oncological disorders, the compounds of this invention can be administered to a patient in need of treatment in combination with other antitumor or anticancer substances and/or with radiation and/or photodynamic therapy and/or with surgical treatment to remove a tumor. These other substances or treatments may be given at the same as or at different times from the compounds or compositions of this invention. For example, the compounds or compositions of the present invention can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs, antibodies, or interferons, such as, for example, GLEEVEC (Novartis Pharmaceuticals Corporation), HERCEPTIN (Genentech, Inc.), and INTRON A (Schering-Plough), respectively. In one embodiment, compounds and compositions of the invention can be used in combination with other Shp2 inhibitors, including, but not limited to, CDL 4340-0580 and NAT6-297775.

Many tumors and cancers have viral genome present in the tumor or cancer cells. For example, Epstein-Barr Virus (EBV) is associated with a number of mammalian malignancies. The compounds of the subject invention can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds of the subject invention can also be used in combination with viral based treatments of oncologic disease. For example, compounds of the invention can be used with mutant herpes simplex virus in the treatment of non-small cell lung cancer (Toyoizumi et al., 1999).

While inhibitor compounds of the invention can be administered as isolated compounds, these compounds can also be administered as part of a pharmaceutical composition. The subject invention thus further provides compositions comprising one or more compounds in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The inhibitor compounds of the invention can be formulated according to known methods for preparing pharmaceutically useful compositions. Formulations suitable for administration include, for example, aqueous sterile injection solutions, which may contain antioxidants, buffers, bacteriostats, and solutes that render the formulation isotonic with the blood or other physiological fluids of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

The compounds of the present invention include all hydrates and salts that can be prepared by those of skill in the art. Under conditions where the compounds of the present invention are sufficiently basic or acidic to form stable non-toxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be for toed, including hydrochloride, sulfate, nitrate, bicarbonate, and carbonate salts.

Pharmaceutically acceptable salts of a compound may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Therapeutic application of compounds and compositions containing them can be accomplished by any suitable therapeutic method and technique presently or prospectively known to those skilled in the art. Further, compounds of the invention have use as starting materials or intermediates for the preparation of other useful compounds and compositions.

Compounds of the invention, and compositions thereof, may be locally administered at one or more anatomical sites, such as sites of unwanted cell growth (such as a tumor site or benign skin growth, e.g., injected or topically applied to the tumor or skin growth) or sites of fungal infection, optionally in combination with a pharmaceutically acceptable carrier such as an inert diluent. Compounds of the invention, and compositions thereof, may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Compounds and compositions of the invention, including pharmaceutically acceptable salts or analogs thereof, can be administered intravenously, intramuscularly, or intraperitoneally by infusion or injection. Solutions of the active compound can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound or composition of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and compositions of the invention may be applied in as a liquid or solid. However, it will generally be desirable to administer them topically to the skin as compositions, in combination with a dermatologically acceptable carrier, which may be a solid or a liquid. Compounds and compositions of the subject invention can be applied topically to a subject's skin to reduce the size (and may include complete removal) of malignant or benign growths, or to treat an infection site. Compounds and compositions of the invention can be applied directly to the growth or infection site. Preferably, the compounds and compositions are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. No. 4,608,392; U.S. Pat. No. 4,992,478; U.S. Pat. No. 4,559,157; and U.S. Pat. No. 4,820,508.

Useful dosages of the compounds and pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The present invention also concerns pharmaceutical compositions comprising a compound of the invention in combination with a pharmaceutically acceptable carrier. Pharmaceutical compositions adapted for oral, topical or parenteral administration, comprising an amount of a compound constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and compositions contemplated by the present invention can be administered to a patient in need of treatment prior to, subsequent to, or in combination with other antitumor or anti-cancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and compositions of the present invention can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments may be given at the same as or at different times from the compounds of this invention. Examples of other chemotherapeutic agents contemplated within the scope of the invention include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of immunotherapeutic agents contemplated within the scope of the invention include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$ $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.). The subject invention also concerns methods for treating an oncological disorder comprising administering an effective amount of a compound or composition of the invention prior to, subsequent to, and/or in combination with administration of a chemotherapeutic agent, an immunotherapeutic agent, a radiotherapeutic agent, or radiotherapy.

Examples of some chemotherapeutic agents that can be used according to the present invention are listed in Table 2.

TABLE 2

Examples of Chemotherapeutic Agents

13-cis-Retinoic Acid
2-Amino-6-Mercaptopurine
2-CdA
2-Chlorodeoxyadenosine
5-fluorouracil
5-FU
6-TG
6-Thioguanine
6-Mercaptopurine
6-MP
Accutane
Actinomycin-D
Adriamycin
Adrucil
Agrylin
Ala-Cort
Aldesleukin
Alemtuzumab
Alitretinoin
Alkaban-AQ
Alkeran
All-transretinoic acid
Alpha interferon
Altretamine
Amethopterin
Amifostine
Aminoglutethimide
Anagrelide
Anandron
Anastrozole
Arabinosylcytosine
Ara-C
Aranesp
Aredia
Arimidex
Aromasin
Arsenic trioxide
Asparaginase
ATRA
Avastin
BCG
BCNU
Bevacizumab
Bexarotene
Bicalutamide
BiCNU
Blenoxane
Bleomycin
Bortezomib
Busulfan
Busulfex
C225
Calcium Leucovorin
Campath
Camptosar
Camptothecin-11
Capecitabine
Carac
Carboplatin
Carmustine
Carmustine wafer
Casodex
CCNU
CDDP
CeeNU
Cerubidine
cetuximab
Chlorambucil
Cisplatin
Citrovorum Factor
Cladribine
Cortisone
Cosmegen
Mylocel
Letrozole
Neosar
Neulasta
Neumega
Neupogen
Nilandron
Nilutamide
Nitrogen Mustard
Novaldex
Novantrone
Octreotide
Octreotide acetate
Oncospar
Oncovin
Ontak
Onxal
Oprevelkin
Orapred
Orasone
Oxaliplatin
Paclitaxel
Pamidronate
Panretin
Paraplatin
Pediapred
PEG Interferon
Pegaspargase
Pegfilgrastim
PEG-INTRON
PEG-L-asparaginase
Phenylalanine Mustard
Platinol
Platinol-AQ
Prednisolone
Prednisone
Prelone
Procarbazine
PROCRIT
Proleukin
Prolifeprospan 20 with Carmustine implant
Purinethol
Raloxifene
Rheumatrex
Rituxan
Rituximab
Roveron-A (interferon alfa-2a)
Rubex
Rubidomycin hydrochloride
Sandostatin
Sandostatin LAR
Sargramostim
Solu-Cortef
Solu-Medrol
STI-571
Streptozocin
Tamoxifen
Targretin
Taxol
Taxotere
Temodar
Temozolomide
Teniposide
TESPA
Thalidomide
Thalomid
TheraCys
Thioguanine
Thioguanine Tabloid
Thiophosphoamide
Thioplex
Thiotepa
TICE
Toposar

TABLE 2-continued

Examples of Chemotherapeutic Agents

CPT-11
Cyclophosphamide
Cytadren
Cytarabine
Cytarabine liposomal
Cytosar-U
Cytoxan
Dacarbazine
Dactinomycin
Darbepoetin alfa
Daunomycin
Daunorubicin
Daunorubicin hydrochloride
Daunorubicin liposomal
DaunoXome
Decadron
Delta-Cortef
Deltasone
Denileukin diftitox
DepoCyt
Dexamethasone
Dexamethasone acetate
dexamethasone sodium phosphate
Dexasone
Dexrazoxane
DHAD
DIC
Diodex
Docetaxel
Doxil
Doxorubicin
Doxorubicin liposomal
Droxia
DTIC
DTIC-Dome
Duralone
Efudex
Eligard
Ellence
Eloxatin
Elspar
Emcyt
Epirubicin
Epoctin alfa
Erbitux
Erwinia L-asparaginase
Estramustine
Ethyol
Etopophos
Etoposide
Etoposide phosphate
Eulexin
Evista
Exemestane
Fareston
Faslodex
Femara
Filgrastim
Floxuridine
Fludara
Fludarabine
Fluoroplex
Fluorouracil
Fluorouracil (cream)
Fluoxymesterone
Flutamide
Folinic Acid
FUDR
Fulvestrant
G-CSF
Gefitinib
Gemcitabine
Gemtuzumab ozogamicin
Gemzar
Gleevec
Lupron
Topotecan
Toremifene
Trastuzumab
Tretinoin
Trexall
Trisenox
TSPA
VCR
Velban
Velcade
VePesid
Vesanoid
Viadur
Vinblastine
Vinblastine Sulfate
Vincasar Pfs
Vincristine
Vinorelbine
Vinorelbine tartrate
VLB
VP-16
Vumon
Xeloda
Zanosar
Zevalin
Zinecard
Zoladex
Zoledronic acid
Zometa
Gliadel wafer
Glivec
GM-CSF
Goserelin
granulocyte - colony stimulating factor
Granulocyte macrophage colony stimulating factor
Halotestin
Herceptin
Hexadrol
Hexalen
Hexamethylmelamine
HMM
Hycamtin
Hydrea
Hydrocort Acetate
Hydrocortisone
Hydrocortisone sodium phosphate
Hydrocortisone sodium succinate
Hydrocortone phosphate
Hydroxyurea
Ibritumomab
Ibritumomab Tiuxetan
Idamycin
Idarubicin
Ifex
IFN-alpha
Ifosfamide
IL-2
IL-11
Imatinib mesylate
Imidazole Carboxamide
Interferon alfa
Interferon Alfa-2b (PEG conjugate)
Interleukin-2
Interleukin-11
Intron A (interferon alfa-2b)
Leucovorin
Leukeran
Leukine
Leuprolide
Leurocristine
Leustatin
Liposomal Ara-C
Liquid Pred
Lomustine
L-PAM
L-Sarcolysin
Meticorten TABLE 2-continued Examples of Chemotherapeutic Agents

| | |
|---|---|
| Lupron Depot | Mitomycin |
| Matulane | Mitomycin-C |
| Maxidex | Mitoxantrone |
| Mechlorethamine | M-Prednisol |
| Mechlorethamine | MTC |
| Hydrochlorine | MTX |
| Medralone | Mustargen |
| Medrol | Mustine |
| Megace | Mutamycin |
| Megestrol | Myleran |
| Megestrol Acetate | Iressa |
| Melphalan | Irinotecan |
| Mercaptopurine | Isotretinoin |
| Mesna | Kidrolase |
| Mesnex | Lanacort |
| Methotrexate | L-asparaginase |
| Methotrexate Sodium | LCR |
| Methylprednisolone | |

The subject invention also concerns methods for inhibiting Shp2 function in a cell by contacting the cell with an effective amount of a compound or composition of the invention. In one embodiment, the cell is a human or mammalian cell, and can be a cancer or tumor cell or other cell that exhibits abnormal proliferation, survival, migration or differentiation. In one embodiment, the cell constitutively expresses or expresses elevated or abnormal levels of a Shp2 or a mutated Shp2.

The subject invention also concerns methods for treating a person or animal having a disorder associated with constitutive, abnormal, or elevated expression of Shp2 in a cell, or a mutation in Shp2, wherein a therapeutically effective amount of a compound or composition of the invention is administered to the person or animal. The disorder can be one characterized, for example, by abnormal cell proliferation, cell survival, cell migration, and/or cell differentiation. In one embodiment, the disorder is Noonan syndrome or LEOPARD syndrome.

Depending upon the disorder or disease condition to be treated, a suitable dose(s) may be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound or composition can be continuous or at distinct intervals, as can be determined by a person of ordinary skill in the art.

To provide for the administration of such dosages for the desired therapeutic treatment, in some embodiments, pharmaceutical compositions of the invention can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The subject invention also concerns kits comprising an inhibitor compound and/or composition of the invention in one or more containers. Kits of the invention can optionally include pharmaceutically acceptable carriers and/or diluents. In one embodiment, a kit of the invention includes one or more other components, adjuncts, or adjuvants as described herein. In another embodiment, a kit includes one or more anti-cancer agents, such as those agents described herein. In one embodiment, a kit of the invention includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or composition of the invention is provided in the kit as a solid, such as a tablet, pill, or powder form. In another embodiment, a compound and/or composition of the invention is provided in the kit as a liquid or solution. In one embodiment, the kit comprises an ampoule or syringe containing a compound and/or agent of the invention in liquid or solution form.

Mammalian species which benefit from the methods of the present invention include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient" and "subject" are used interchangeably and are intended to include such human and non-human species. Likewise, in vitro methods of the present invention can be carried out on cells of such human and non-human species.

TABLE 3

IC$_{50}$ values for indoline Shp2 inhibitors of the present invention, as determined by in vitro phosphotyrosine phosphatase activity (DiFMUP) assay. Numerous batches were tested, as indicated by the batch number in column 1.

| Name, Structure, Molecular Weight | IC$_{50}$ (μM) |
|---|---|
| XW2-038H 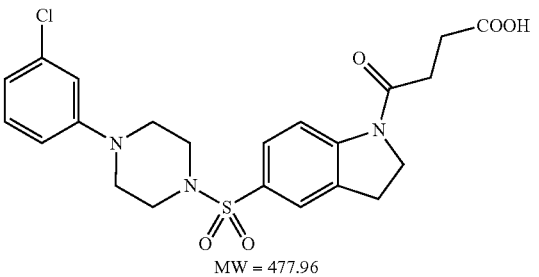 MW = 477.96 | 0.7 ± 0.3 n = 44 |

TABLE 3-continued
IC$_{50}$ values for indoline Shp2 inhibitors of the present invention, as determined by in vitro phosphotyrosine phosphatase activity (DiFMUP) assay. Numerous batches were tested, as indicated by the batch number in column 1.
| Name, Structure, Molecular Weight | IC$_{50}$ (µM) |
|---|---|
| XW2-125B 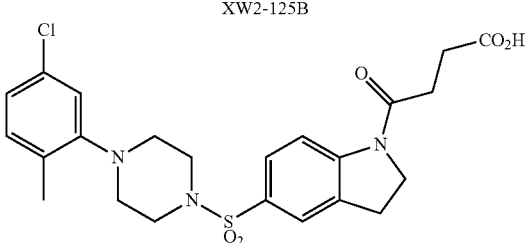 MW = 491.99 | 1.5 ± 0<br>n = 4 |
| JHE-02-001 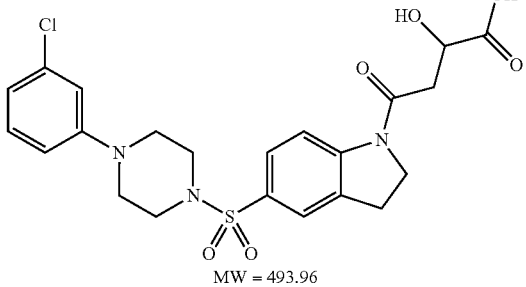 MW = 493.96 | 1.1 ± 0.3<br>n = 8 |
| JHE-02-119 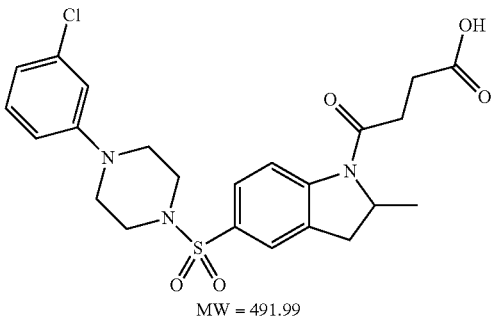 MW = 491.99 | 2.5 ± 0.5<br>n = 4 |
| JHE-02-067 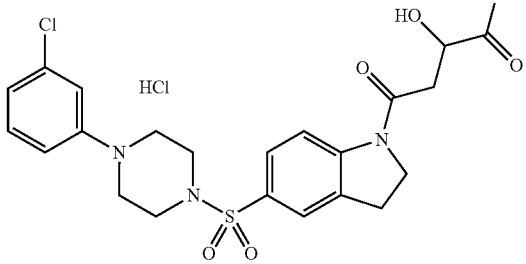 MW = 530.42<br>1.07 mg submitted on Jun. 30, 2008 | 1.3 ± 0.5<br>n = 3 |

TABLE 3-continued
IC$_{50}$ values for indoline Shp2 inhibitors of the present invention, as determined by in vitro phosphotyrosine phosphatase activity (DiFMUP) assay. Numerous batches were tested, as indicated by the batch number in column 1.
| Name, Structure, Molecular Weight | IC$_{50}$ (μM) |
|---|---|
| JHE-01-129A 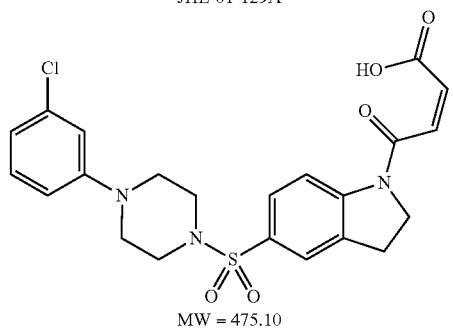 MW = 475.10 | 2.8 ± 0.7 n = 3 |
| JHE-02-032A 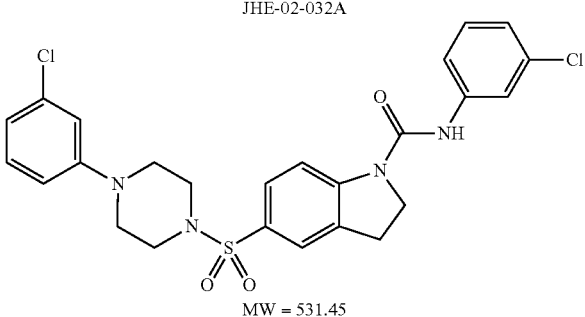 MW = 531.45 | 8.3 ± 3.4 n = 4 |
| JHE-02-065B 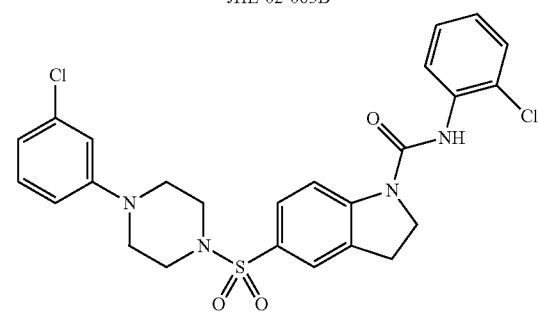 MW = 531.45 | 3.2 ± 0.5 n = 4 |
| JHE-02-068B 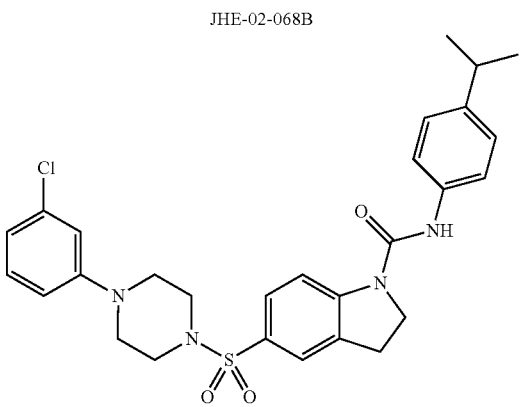 MW = 539.09 | 4.1 ± 1.0 n = 4 |

TABLE 3-continued

IC$_{50}$ values for indoline Shp2 inhibitors of the present invention, as determined by in vitro phosphotyrosine phosphatase activity (DiFMUP) assay. Numerous batches were tested, as indicated by the batch number in column 1.

| Name, Structure, Molecular Weight | IC$_{50}$ (μM) |
|---|---|
| XW3-002<br>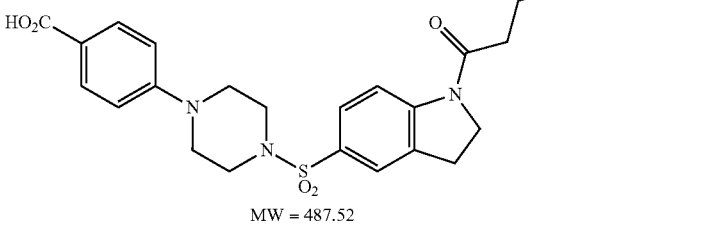<br>MW = 487.52 | 6.1 ± 1.8<br>n = 4 |
| JHE-02-068A<br>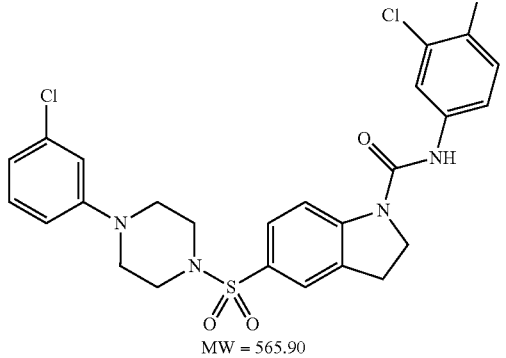<br>MW = 565.90 | 5.7 ± 2.5<br>n = 4 |
| JHE-01-129B<br>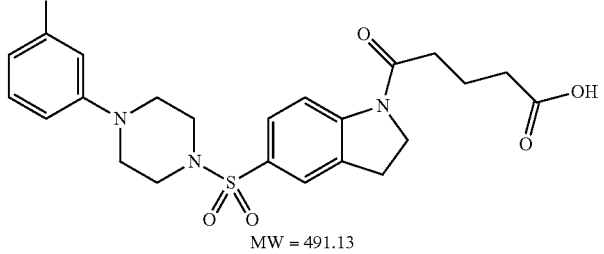<br>MW = 491.13 | 2.8 ± 0.7<br>n = 3 |
| JF028<br>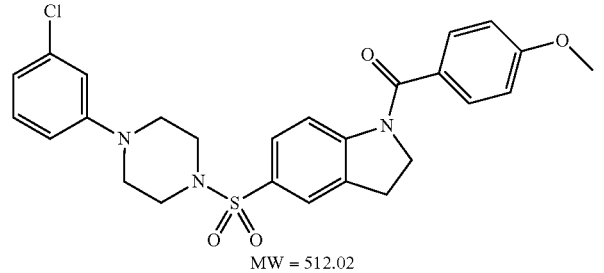<br>MW = 512.02 | 6.3 ± 2.9<br>n = 5 |

TABLE 3-continued
IC$_{50}$ values for indoline Shp2 inhibitors of the present invention, as determined by in vitro phosphotyrosine phosphatase activity (DiFMUP) assay. Numerous batches were tested, as indicated by the batch number in column 1.
| Name, Structure, Molecular Weight | IC$_{50}$ (µM) |
|---|---|
| JHE-02-065A 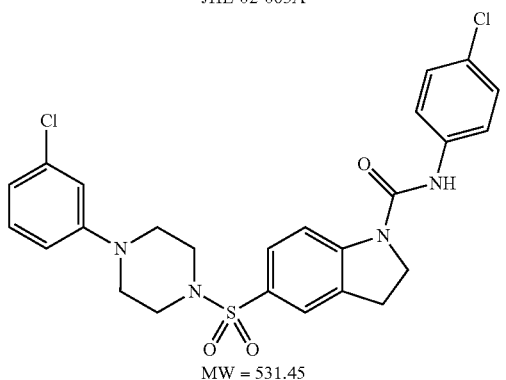 MW = 531.45 | 19.1 ± 5.1 n = 5 |
| JF026 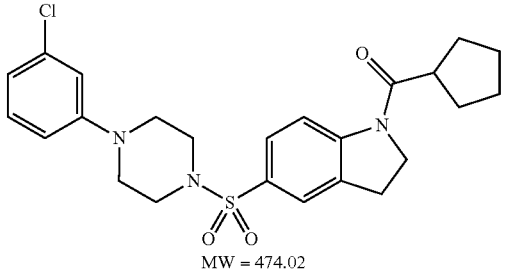 MW = 474.02 | 6.9 ± 2.2 n = 5 |
| JF020 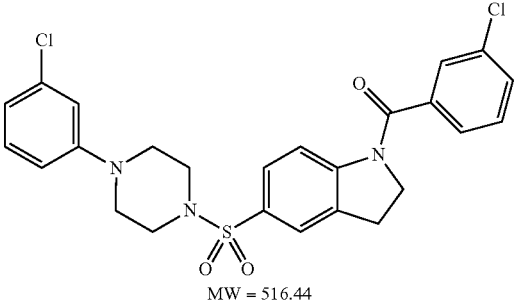 MW = 516.44 | 5.7 ± 3.9 n = 4 |
| JHE-01-137 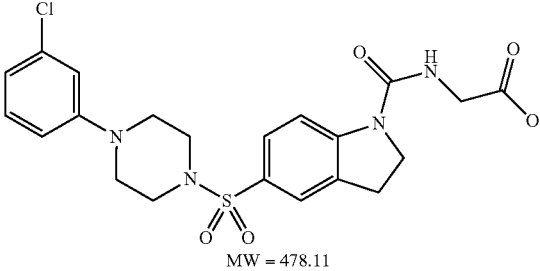 MW = 478.11 | 4.6 ± 0.3 n = 3 |

TABLE 3-continued
IC$_{50}$ values for indoline Shp2 inhibitors of the present invention, as determined by in vitro phosphotyrosine phosphatase activity (DiFMUP) assay. Numerous batches were tested, as indicated by the batch number in column 1.
| Name, Structure, Molecular Weight | IC$_{50}$ (μM) |
|---|---|
| JHE-02-033B 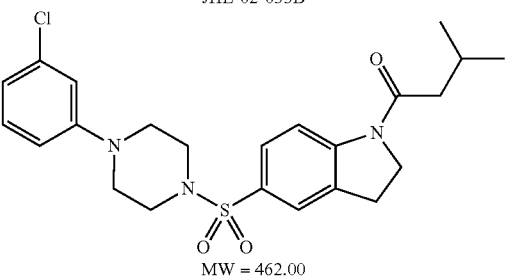 MW = 462.00 | 20.7 ± 10.8 n = 4 |
| JHE-02-038 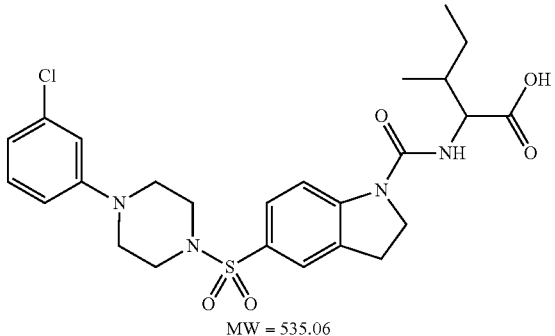 MW = 535.06 | 15.5 ± 7.5 n = 4 |
| JHE-02-032B 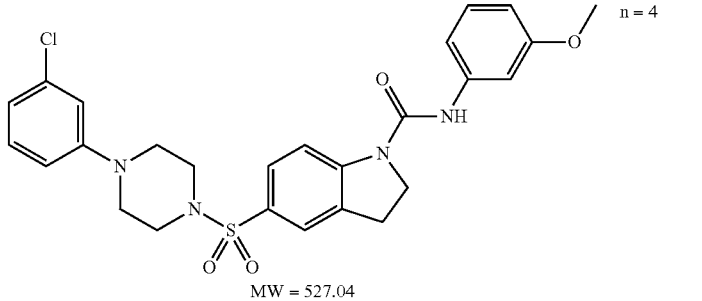 MW = 527.04 | 9.9 ± 3.5 n = 4 |
| JF025 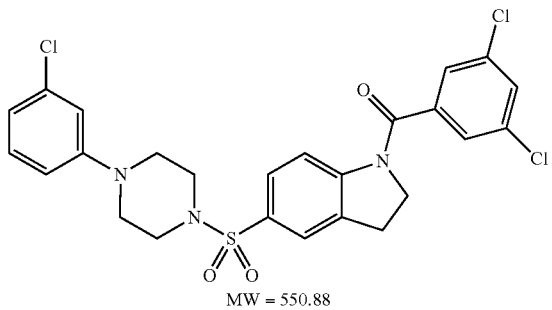 MW = 550.88 | 8.2 ± 2.6 n = 5 |

TABLE 3-continued
IC$_{50}$ values for indoline Shp2 inhibitors of the present invention, as determined by in vitro phosphotyrosine phosphatase activity (DiFMUP) assay. Numerous batches were tested, as indicated by the batch number in column 1.
| Name, Structure, Molecular Weight | IC$_{50}$ (µM) |
|---|---|
| JHE-02-063B 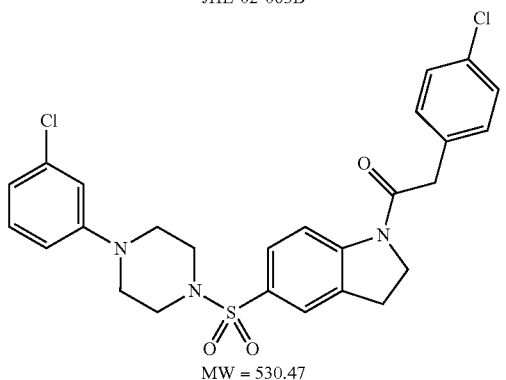 MW = 530.47 | 8.0 ± 1.9 n = 4 |
| JF024 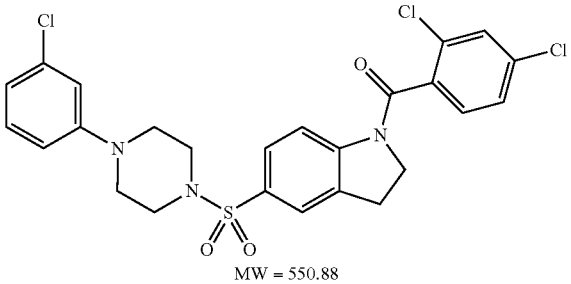 MW = 550.88 | 7.6 ± 1.3 n = 5 |
| XW2-057 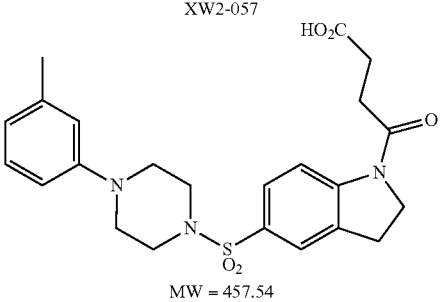 MW = 457.54 | 3.4 ± 2.3 n = 5 |
| XW2-124B 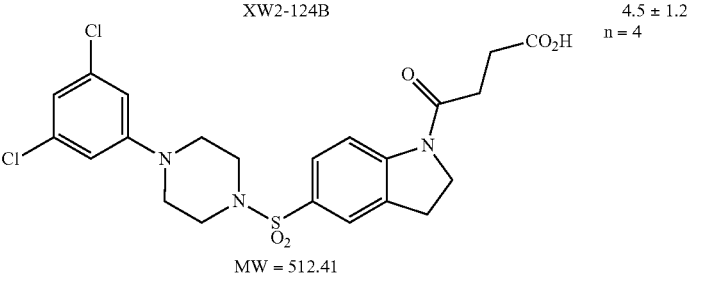 MW = 512.41 | 4.5 ± 1.2 n = 4 |

TABLE 3-continued
IC$_{50}$ values for indoline Shp2 inhibitors of the present invention, as determined by in vitro phosphotyrosine phosphatase activity (DiFMUP) assay. Numerous batches were tested, as indicated by the batch number in column 1.
| Name, Structure, Molecular Weight | IC$_{50}$ (µM) |
|---|---|
| JF038<br>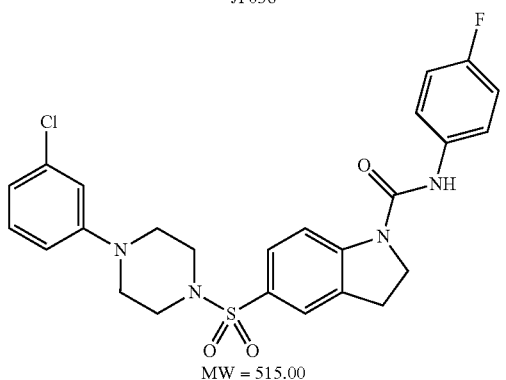<br>MW = 515.00 | 12.6 ± 5.4<br>n = 5 |
| JHE-02-017B<br>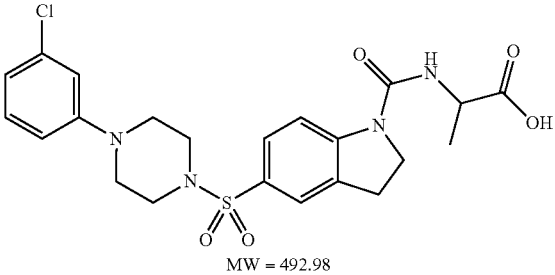<br>MW = 492.98 | 6.4 ± 0.5<br>n = 5 |
| JF027<br>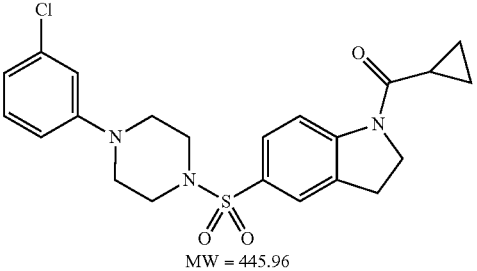<br>MW = 445.96 | 8.5 ± 2.0<br>n = 5 |
| XW2-119<br>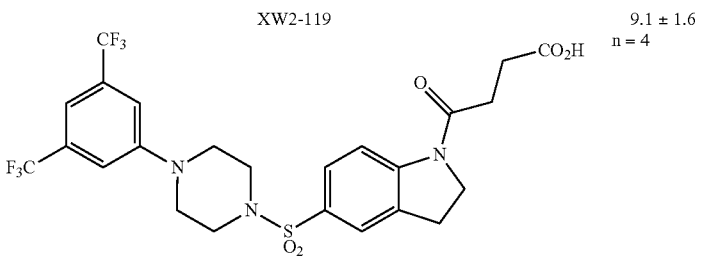<br>MW = 579.51 | 9.1 ± 1.6<br>n = 4 |

TABLE 3-continued
IC$_{50}$ values for indoline Shp2 inhibitors of the present invention, as determined by in vitro phosphotyrosine phosphatase activity (DiFMUP) assay. Numerous batches were tested, as indicated by the batch number in column 1.
| Name, Structure, Molecular Weight | IC$_{50}$ (μM) |
| --- | --- |
| JHE-02-012 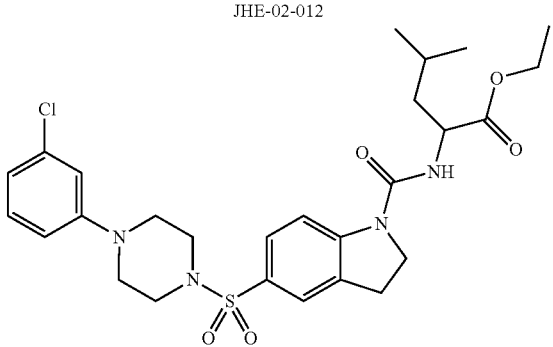 MW = 563.11 | 6.0 ± 2.8 n = 3 |
| XW2-036 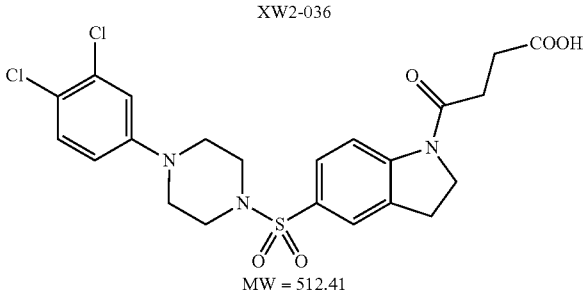 MW = 512.41 | 4.6 ± 2.4 n = 7 |
| JHE-02-035A 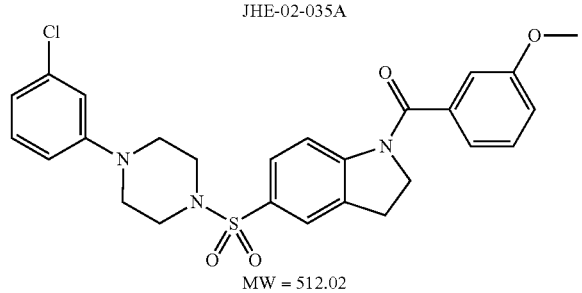 MW = 512.02 | 8.1 ± 0.8 n = 4 |
| JF022 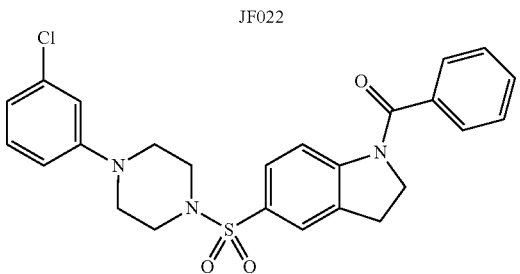 MW = 481.99 | 8.4 ± 2.3 n = 7 |

TABLE 3-continued
IC$_{50}$ values for indoline Shp2 inhibitors of the present invention, as determined by in vitro phosphotyrosine phosphatase activity (DiFMUP) assay. Numerous batches were tested, as indicated by the batch number in column 1.
| Name, Structure, Molecular Weight | IC$_{50}$ (μM) |
| --- | --- |
| JHE-02-017C 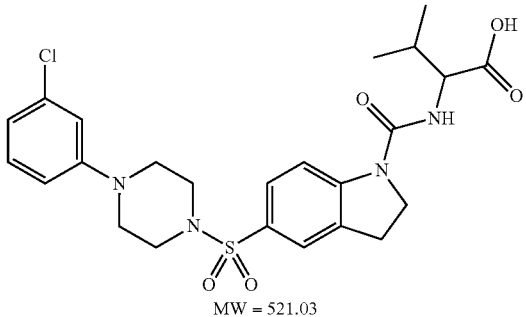 MW = 521.03 | 4.4 ± 1.9 n = 6 |
| JF023 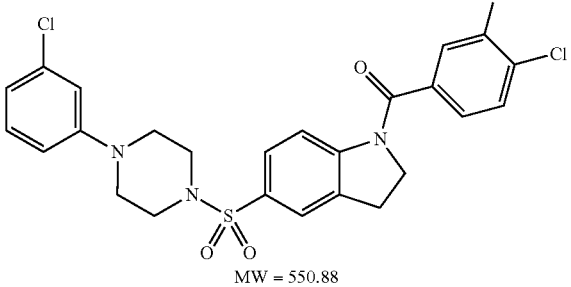 MW = 550.88 | 7.1 ± 1.8 n = 6 |
| JF039 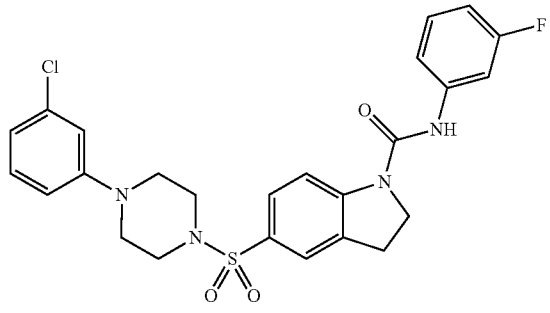 [SMILES: O=C(Nc1cccc(F)c1)N1CCc2cc(S(=O)(=O)N3CCN(c4cccc(Cl)c4)CC3)ccc21] MW = 515.00 | 8.1 ± 1.7 n = 6 |
| JHE-02-069 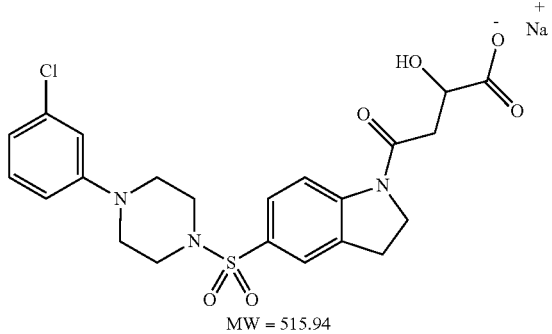 MW = 515.94 | 8.2 ± 0.4 n = 3 |

TABLE 3-continued
IC$_{50}$ values for indoline Shp2 inhibitors of the present invention, as determined by in vitro phosphotyrosine phosphatase activity (DiFMUP) assay. Numerous batches were tested, as indicated by the batch number in column 1.
| Name, Structure, Molecular Weight | IC$_{50}$ (μM) |
| --- | --- |
| JHE-02-010B 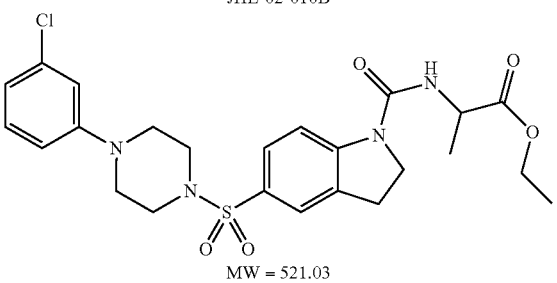 MW = 521.03 | 5.1 ± 2.7 n = 6 |
| JF040 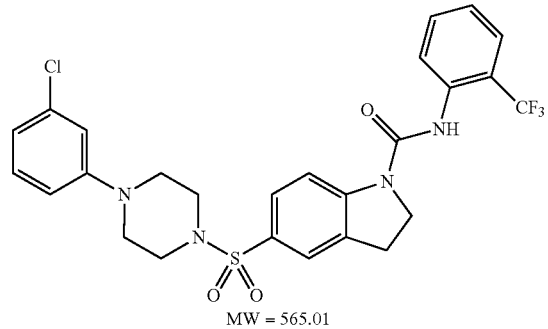 MW = 565.01 | 9.0 ± 1.7 n = 6 |
| JHE-01-155B 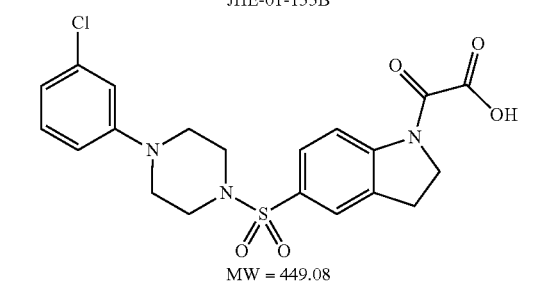 MW = 449.08 | 4.8 ± 2.8 |
| JF021 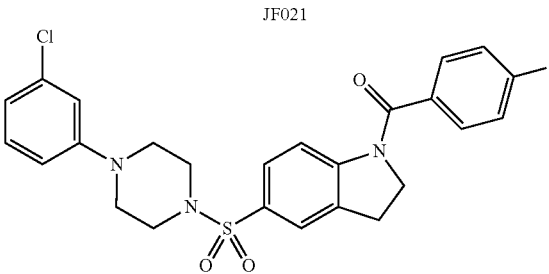 MW = 516.44 | 10.4 ± 2.0 n = 3 |

TABLE 3-continued
IC$_{50}$ values for indoline Shp2 inhibitors of the present invention, as determined by in vitro phosphotyrosine phosphatase activity (DiFMUP) assay. Numerous batches were tested, as indicated by the batch number in column 1.
| Name, Structure, Molecular Weight | IC$_{50}$ (μM) |
|---|---|
| JHE-02-033A 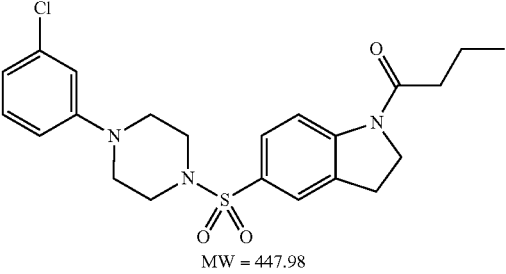 MW = 447.98 | 7.8 ± 2.1 n = 4 |
| JHE-02-017A 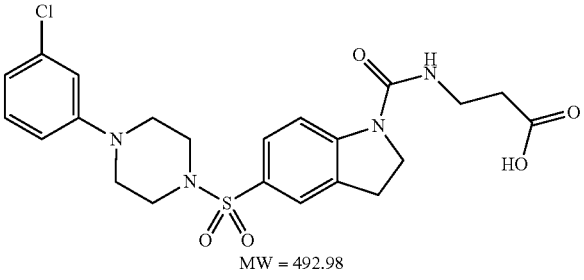 MW = 492.98 | 4.8 ± 3.3 n = 6 |
| JHE-02-010C 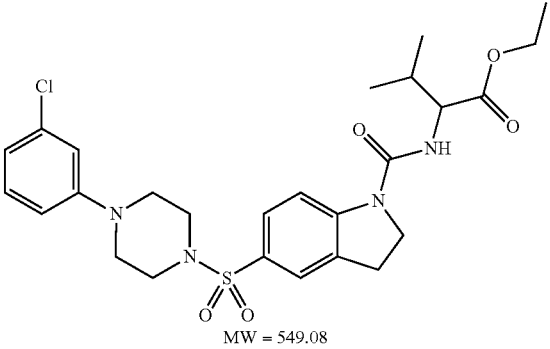 MW = 549.08 | 7.7 ± 2.4 n = 5 |
| JHE-02-019A 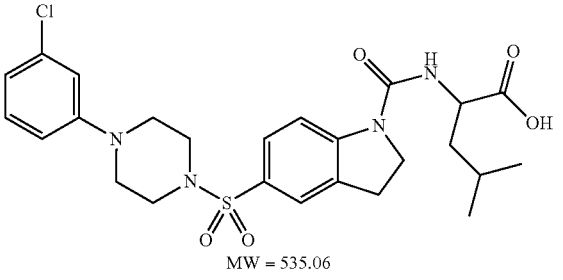 MW = 535.06 | 4.5 ± 3.5 n = 3 |

TABLE 3-continued

IC$_{50}$ values for indoline Shp2 inhibitors of the present invention, as determined by in vitro phosphotyrosine phosphatase activity (DiFMUP) assay. Numerous batches were tested, as indicated by the batch number in column 1.

| Name, Structure, Molecular Weight | IC$_{50}$ (µM) |
|---|---|
| JF035<br>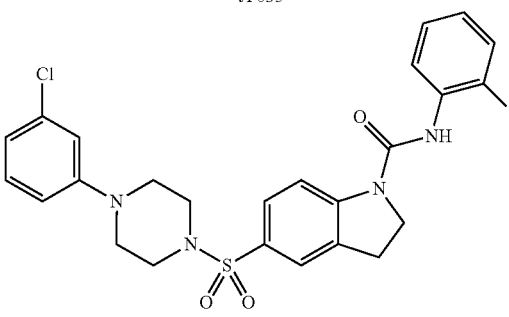<br>MW = 515.00 | 12.2 ± 2.0<br>n = 5 |
| XW2-038F<br>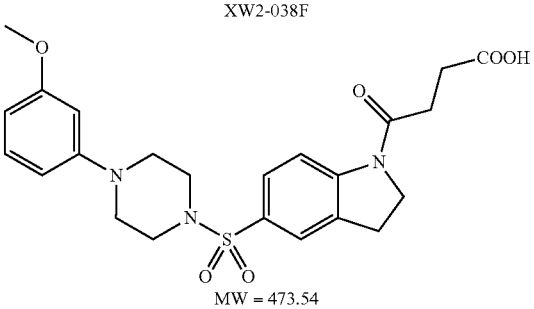<br>MW = 473.54 | 4.7 ± 4.4<br>n = 5 |
| JF033<br>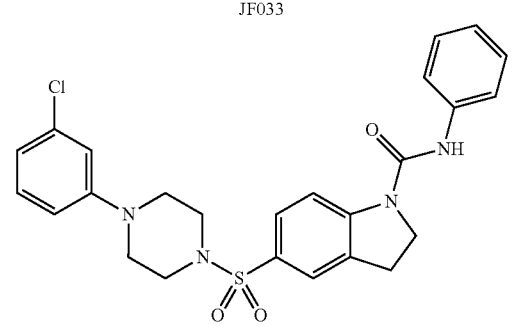<br>MW = 497.01 | 11.7 ± 1.4<br>n = 5 |
| JHE-02-010A<br>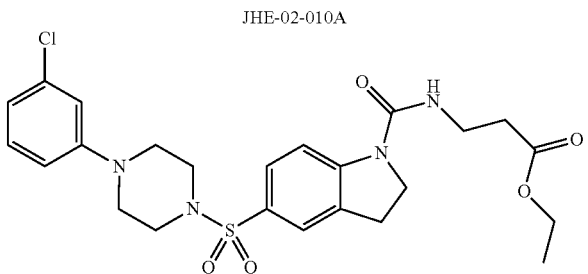<br>MW = 521.03 | 9.3 ± 2.2<br>n = 5 |

TABLE 3-continued
IC$_{50}$ values for indoline Shp2 inhibitors of the present invention, as determined by in vitro phosphotyrosine phosphatase activity (DiFMUP) assay. Numerous batches were tested, as indicated by the batch number in column 1.
| Name, Structure, Molecular Weight | IC$_{50}$ (μM) |
|---|---|
| JHE-02-014 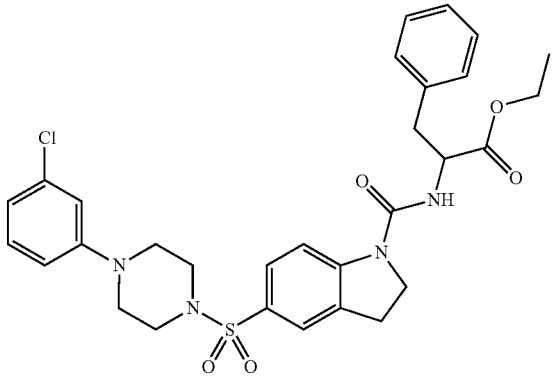 [SMILES: CCOC(=O)C(Cc1ccccc1)NC(=O)N1CCc2cc(S(=O)(=O)N3CCN(c4cccc(Cl)c4)CC3)ccc21] MW = 597.12 | 6.9 ± 4.2 n = 6 |
| JHE-02-029A 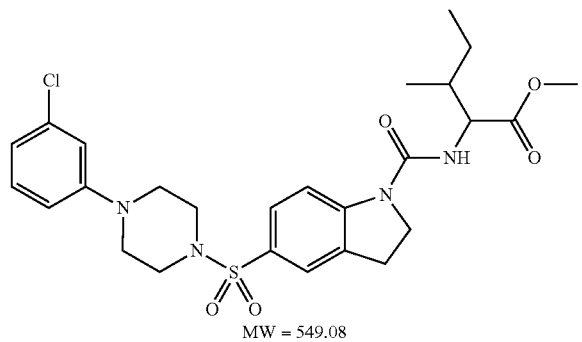 MW = 549.08 | 12.7 ± 0.7 n = 4 |
| XW2-031B 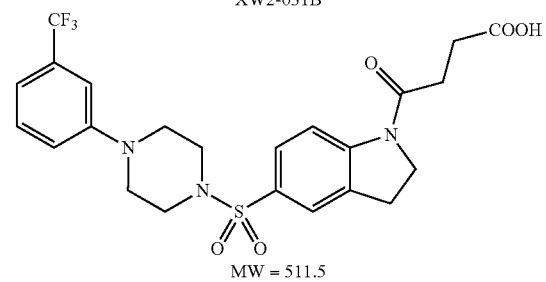 MW = 511.5 | 11.3 ± 3.1 n = 5 |
| JHE-02-020B 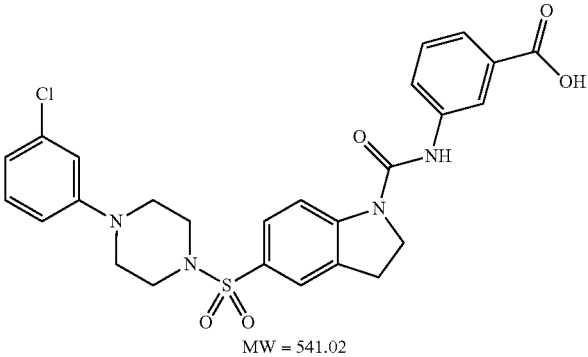 MW = 541.02 | 3.0 ± 0.8 n = 5 |

TABLE 3-continued

IC$_{50}$ values for indoline Shp2 inhibitors of the present invention, as determined by in vitro phosphotyrosine phosphatase activity (DiFMUP) assay. Numerous batches were tested, as indicated by the batch number in column 1.

| Name, Structure, Molecular Weight | IC$_{50}$ (µM) |
|---|---|
| XW2-124A<br />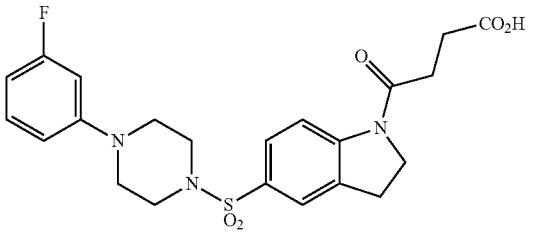<br />MW = 461.51 | 13.2 ± 3.6<br />n = 4 |
| JHE-02-020A<br />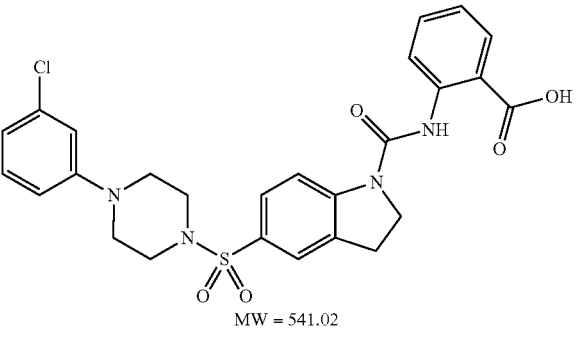<br />MW = 541.02 | 8.3 ± 5.6<br />n = 6 |
| JHE-02-007<br />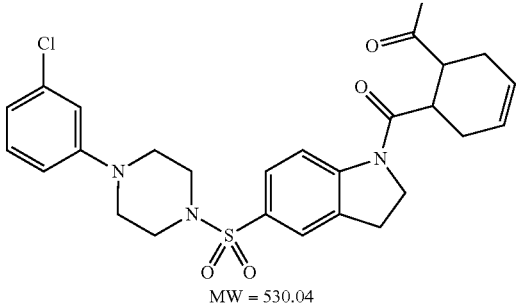<br />MW = 530.04 | 20.3 ± 4.3<br />n = 5 |
| XW2-038E<br />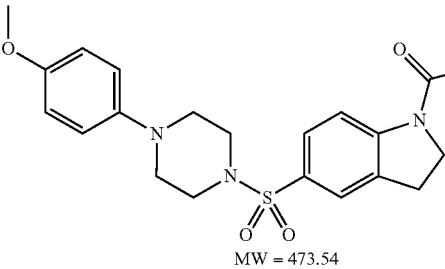<br />MW = 473.54 | 9.0 ± 5.9<br />n = 5 |

TABLE 3-continued
IC$_{50}$ values for indoline Shp2 inhibitors of the present invention, as determined by in vitro phosphotyrosine phosphatase activity (DiFMUP) assay. Numerous batches were tested, as indicated by the batch number in column 1.
| Name, Structure, Molecular Weight | IC$_{50}$ (μM) |
|---|---|
| JHE-02-019B 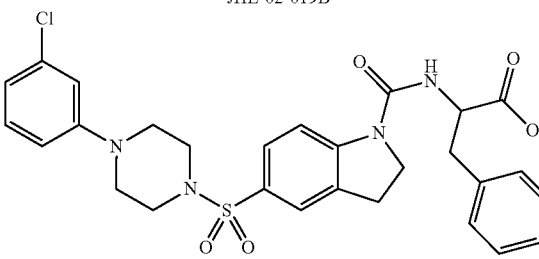 MW = 569.07 | 5.4 ± 2.7 n = 5 |
| JHE-02-015A 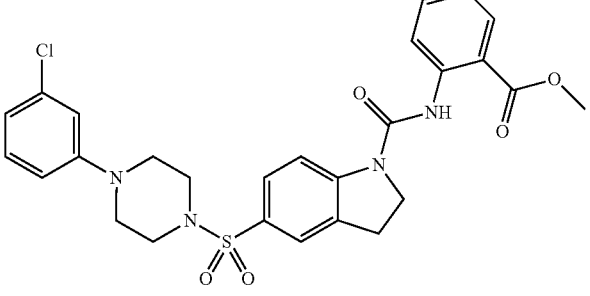 MW = 555.05 | 14.3 ± 4.1 n = 5 |
| XW3-006 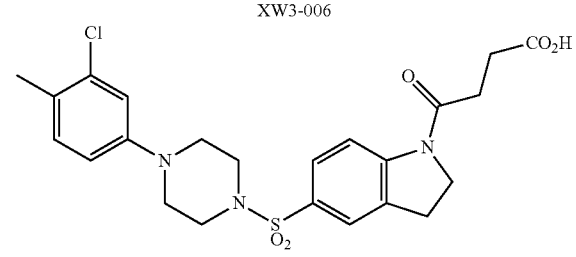 MW = 478.96 | 16.6 ± 3.6 |
| JHE-01-169 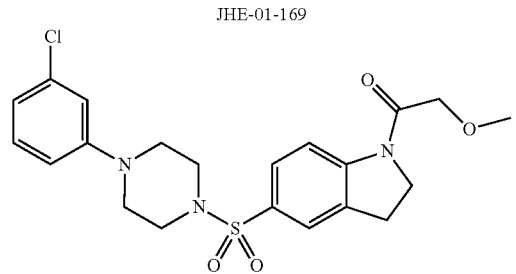 MW = 449.95 | 9.6 ± 2.4 n = 5 |

TABLE 3-continued

IC$_{50}$ values for indoline Shp2 inhibitors of the present invention, as determined by in vitro phosphotyrosine phosphatase activity (DiFMUP) assay. Numerous batches were tested, as indicated by the batch number in column 1.

| Name, Structure, Molecular Weight | IC$_{50}$ (μM) |
|---|---|
| JF031<br />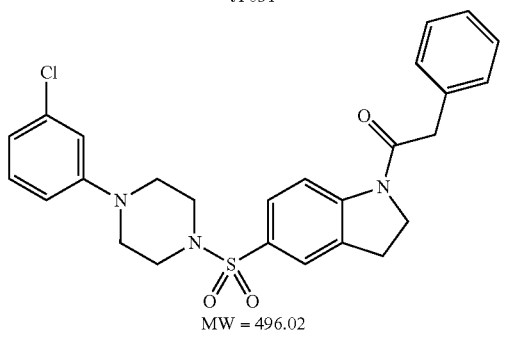<br />MW = 496.02 | 22.8 ± 4.5<br />n = 5 |
| JHE-02-117<br />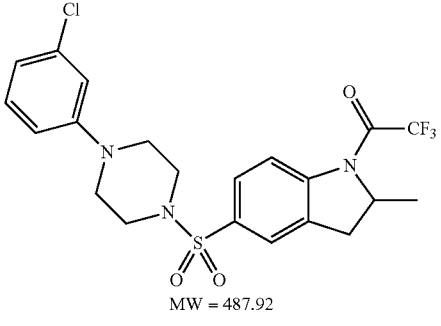<br />MW = 487.92 | 47.0 ± 17.7<br />n = 4 |
| XW2-038A<br />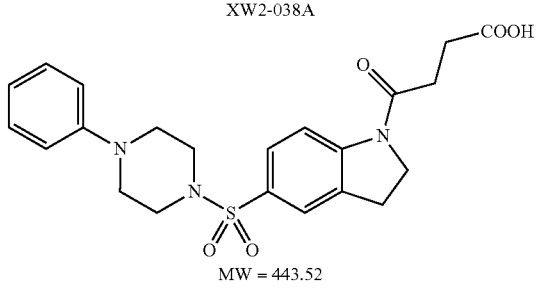<br />MW = 443.52 | 14.8 ± 7.3<br />n = 5 |
| JHE-02-023<br />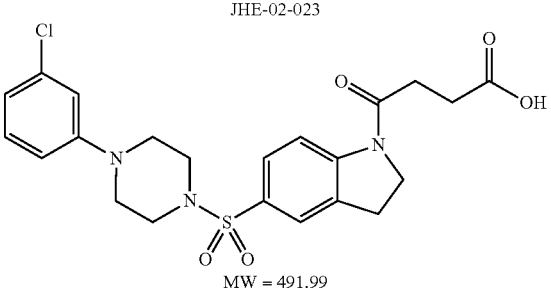<br />MW = 491.99 | 37.3 ± 5.3<br />n = 3 |

TABLE 3-continued

IC$_{50}$ values for indoline Shp2 inhibitors of the present invention, as determined by in vitro phosphotyrosine phosphatase activity (DiFMUP) assay. Numerous batches were tested, as indicated by the batch number in column 1.

| Name, Structure, Molecular Weight | IC$_{50}$ (μM) |
| --- | --- |
| XW2-011B<br>MW = 461.5 | 31.9 ± 10.0<br>n = 5 |
| XW2-038D<br>MW = 461.51 | 34.6 ± 12.6<br>n = 4 |
| JHE-02-052<br>MW = 551.01 | 37.6 ± 13.8<br>n = 6 |
| JHE-01-134A<br>MW = 506.14 | 60.3 |

TABLE 3-continued

IC$_{50}$ values for indoline Shp2 inhibitors of the present invention, as determined by in vitro phosphotyrosine phosphatase activity (DiFMUP) assay. Numerous batches were tested, as indicated by the batch number in column 1.

| Name, Structure, Molecular Weight | IC$_{50}$ (μM) |
|---|---|
| XW2-038G<br>M.W. = 512.41 | 143.6 ± 89.5<br>n = 5 |

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

General

All reagents were purchased from commercial suppliers and used without further purification. Melting points were determined using a Barnstead international melting point apparatus and remain uncorrected. $^1$H NMR spectra were recorded on a Varian Mercury 400 MHz spectrometer with CDCl$_3$ or DMSO-d$_6$ as the solvent. $^{13}$C NMR spectra are recorded at 100 MHz. All coupling constants are measured in Hertz (Hz) and the chemical shifts ($\delta_H$ and $\delta_C$) are quoted in parts per million (ppm) relative to TMS ($\delta 0$), which was used as the internal standard. High resolution mass spectroscopy was carried out on an Agilent 6210 LC/MS (ESI-TOF). Microwave reactions were performed in CEM 908005 model and Biotage initiator 8 machines. HPLC analysis was performed using a JASCO HPLC system equipped with a PU-2089 Plus quaternary gradient pump and a UV-2075 Plus UV-VIS detector, using an Alitech Kromasil C-18 column (150×4.6 mm, 5 μm). Thin layer chromatography was performed using silica gel 60 F254 plates (Fisher), with observation under UV when necessary. Anhydrous solvents (acetonitrile, dimethyl formamide, ethanol, isopropanol, methanol and tetrahydrofuran) were used as purchased from Aldrich. HPLC grade solvents (methanol, acetonitrile and water) were purchased from Burdick and Jackson for HPLC and mass analysis. Compounds were tested for IC$_{50}$ by DiFMUP assay (results shown in Table 3).

Scheme 1.

Conditions and reagents: (a) succinic anhydride, pyridine, microwave, 90° C., 20 min; (b) H$_2$SO$_4$, MeOH, overnight; (c) chlorosulfonic acid, 0-70° C., 45 min; (d) substituted piperazines or substituted amines, pyridine, DCM, rt, 3 hr; (e) 1N LiOH, MeOH, microwave, 90° C., 10 min.

The library with modifications on the piperazine part was synthesized by coupling the sulfonyl chloride XW2-004 with commercially available piperazines or amines. The coupling reaction of indoline with succinic anhydride afforded the free acid XW1-176, which was subsequently methylated to provide ester XW1-181. Sulfonation on the 5-position of XW1-181 gave the key building block XW2-004 in good yield, which was reacted with various piperazines or amines to provide the first generation library.

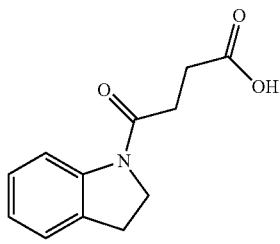 [SMILES: O=C(O)CCC(=O)N1CCc2ccccc21]

XW1-176: 4-(Indolin-1-yl)-4-oxobutanoic acid: *Tetrahedron letters*, 46 (2005), 1021-1022

The procedure was modified from the reported one. In a 20 mL microwave reaction tube equipped with a magnetic stirring bar, indoline (1.196 g, 10 mmol), succinic anhydride (1.004 g, 10 mmol) and pyridine (8 mL) was mixed at room temperature. The tube was capped and irradiated in the microwave reactor (Biotage Initiator I) at 90° C. for 20 minutes. The reaction mixture was acidified to pH=1 using 2 M HCl. The resulting precipitate was filtered, washed with water and dried under high vacuum to afford light pink solid product (1.849 g, 92%). $^1$H NMR (400 MHz, CDCl$_3$) d 8.19 (d, 1H, J=8.5 Hz), 7.18 (m, 2H), 7.03 (t, 1H, J=7.4 Hz), 4.08 (t, 2H, J=8.4 Hz), 3.22 (t, 2H, J=8.4 Hz), 2.78 (m, 4H).

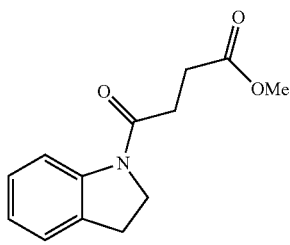 [SMILES: COC(=O)CCC(=O)N1CCc2ccccc21]

XW1-181: Methyl 4-(indolin-1-yl)-4-oxobutanoate

The acid XW1-176 (500 mg, 2.28 mmol) was dissolved in methanol (50 mL) and the solution was chilled in an ice-water bath. At 0° C., 20 drops of concentrated sulfuric acid was added. The solution was allowed to be warmed to room temperature and stirred for 15 hours. The reaction solution was concentrated to about 5 mL. The residue was carefully treated with saturated aq. sodium bicarbonate solution (100 mL). The resulting precipitate was filtered and washed with water. The product was obtained as light pink solid. (475 mg, 89%). $^1$H NMR (400 MHz, CDCl$_3$) d 8.20 (d, 1H, J=8.4 Hz), 7.17 (m, 2H), 7.01 (t, 1H, J=7.3 Hz), 4.10 (t, 2H, J=8.5 Hz), 3.72 (s, 3H), 3.22 (t, 2H, J=8.4 Hz), 2.76 (s, 4H).

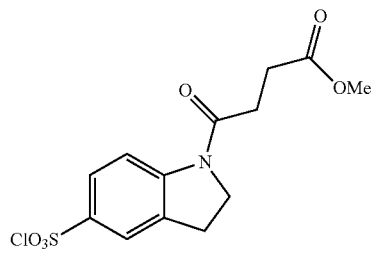

XW2-004:
1-(4-Methoxy-4-oxobutanoyl)indoline-5-sulfonyl chloride

At 0° C., XW1-181 (219 mg, 0.95 mmol) was added to chlorosulfonic acid (1.1 mL) slowly over a period of 20 min. The reaction mixture was then stirred at 0° C. for 3 hours. The clear reaction solution was carefully added to ice-water (70 mL) dropwise. A white precipitate formed and was filtered off and washed with water. The product was obtained as off-white solid. The water filtrate was extracted with ethyl acetate (3×10 mL). Combined ethyl acetate layers were dried over brine, sodium sulfate and the ethyl acetate was then removed under vacuum to afford anther batch of solid product. The two batches of solid product were combined to give of XW2-004 (217 mg, 70%).
$^1$H NMR (400 MHz, CDCl$_3$) δ 8.37 (d, 1H, J=8.3 Hz), 7.88 (dd, 1H, J=2.0, 8.7 Hz), 7.81 (d, 1H, J=2.0 Hz), 4.25 (t, 2H, J=8.0 Hz), 3.72 (s, 3H), 3.32 (t, 2H, J=8.0 Hz), 2.78 (s, 4H).

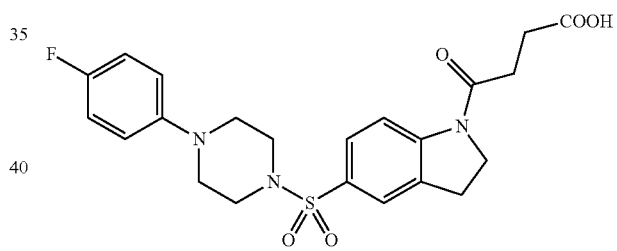

(XW2-011B): 4-(5-(4-(4-Fluorophenyl)piperazin-1-ylsulfonyl)indolin-1-yl)-4-oxobutanoic acid 1-(4-Fluorophenyl)piperazine (185 mg, 1.0 mmol) and pyridine (1 mL) were dissolved in dichloromethane (60 mL) under argon. The solution was chilled in ice-water bath and XW2-004 1-(4-methoxy-4-oxobutanoyl)indoline-5-sulfonyl chloride (333 mg, 1.0 mmol) was added. The reaction solution was then warmed to room temperature and stirred for 3 hours. After the reaction, water [(50 mL with 37% HCl (1 L)] was added to the solution. The organic layer was separated and washed with water, brine and dried over magnesium sulfate. Removal of dichloromethane afforded light green solid product which was then triturated with methanol (10 mL). The white solid product was filtered off to give methyl 4-(5-(4-(4-fluorophenyl)piperazin-1-ylsulfonyl)indolin-1-yl)-4-oxobutanoate, the methyl ester of XW2-011B, (320 mg, yield 67%); $^1$H NMR (400 MHz, CDCl$_3$) δ 8.34 (d, J=8.3 Hz, 1H), 7.62 (dd, 1H, J=8.3, 2.0 Hz), 7.58 (d, 1H, J=2.0 Hz), 6.95 (t, J=9.0 Hz, 2H), 6.84 (m, 2H), 4.21 (t, J=8.6 Hz, 2H), 3.72 (s, 3H), 3.30 (t, J=8.6 Hz, 2H), 3.15 (s, 8H), 2.77 (s, 4H). The white solid obtained from the above reaction (289 mg, 0.63 mmol) was mixed with methanol (10 mL) and lithium hydroxide (1 mL of a 1.0 M aq. solution) in a 20 mL microwave reaction tube. The tube was capped and irradiated in the microwave reactor (Biotage Initiator I) at 90° C. for 10 minutes. The reaction solution was concentrated under vacuum and the residue was diluted with 20 mL of water treated with NaOH solution (1.0 M) till pH>10. The aqueous solution was extracted with ethyl acetate (2×10 mL). Then the aqueous layer was acidified to pH~4, extracted with ethyl acetate (2×150 mL). The organic layer was dried over sodium sulfate and concentrated under vacuum. The resulted solid was washed with dichloromethane to afford XW2-011B (180 mg, 69%) as a light orange solid product. Mp=213-215° C.; $^1$H NMR (400 MHz, CDCl$_3$) δ 8.34 (d, J=8.3 Hz, 1H), 7.58-7.65 (m, 2H), 6.95 (t, J=9.0 Hz, 2H), 6.82 (dd, J=4.5, 4.5 Hz, 2H), 4.20 (t, J=8.6 Hz, 2H), 3.31 (t, J=8.6 Hz, 2H), 3.15 (s, 8H), 2.80 (s, 4H); HPLC 98% (R$_t$=3.30, 90% methanol in acetonitrile); HRMS (ESI-ve) m/z calculated for C$_{22}$H$_{23}$FN$_3$O$_5$S (M−H)−460.13479. found 460.13475.

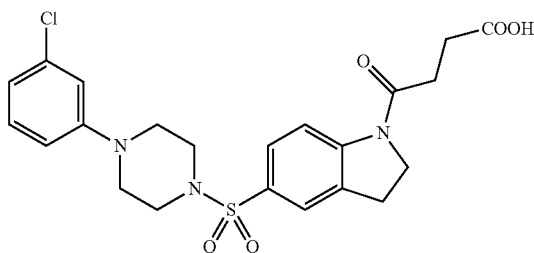 [SMILES: O=C(O)CCC(=O)N1CCc2cc(S(=O)(=O)N3CCN(c4cccc(Cl)c4)CC3)ccc21]

(XW2-038H) 4-(5-(4-(3-Chlorophenyl)piperazin-1-ylsulfonyl)indolin-1-yl)-4-oxobutanoic acid XW2-038H was prepared using the same procedure as described for the preparation of XW2-011B as a white solid, (yield 64%). Mp=228-230° C.; $^1$H NMR (400 MHz, CDCl$_3$) δ 8.21 (d, J=7.4 Hz, 1H), 7.55-7.60 (m, 2H), 7.19 (t, J=8.1 Hz, 2H), 6.78-6.91 (m, 3H), 4.20 (bs, 2H), 3.25 (s, 8H), 2.96 (s, 4H), 2.70 (s, 2H); HPLC 98% (R$_t$=3.00, 30% water in acetonitrile with 0.1% TFA); HRMS (ESI-ve) m/z calculated for C$_{22}$H$_{23}$ClN$_3$O$_5$S (M−H)−476.10524. found 476.10541.

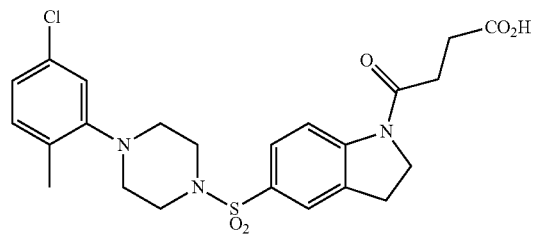 [SMILES: Cc1ccc(Cl)cc1N1CCN(S(=O)(=O)c2ccc3c(c2)CCN3C(=O)CCC(=O)O)CC1]

(XW2-125B) 4-(5-(4-(5-Chloro-2-methylphenyl) piperazin-1-ylsulfonyl)indolin-1-yl)-4-oxobutanoic acid XW2-125B was prepared using the same procedure as described for the preparation of XW2-011B as a white solid, (yield 34%). Mp=255-256° C.; $^1$H NMR (400 MHz, CDCl$_3$) δ 8.22 (d, J=8.0 Hz, 1H), 7.55-7.59 (m, 2H), 7.13 (d, J=8.0 Hz, 1H), 6.99 (m, 2H), 4.20 (t, J=8.5 Hz, 2H), 3.24 (t, J=8.4 Hz, 2H), 2.98 (s, 4H), 2.90 (s, 4H), 2.69 (bs, 2H), 2.07 (s, 3H); HRMS (ESI-ve) m/z calculated for C$_{23}$H$_{27}$ClN$_3$O$_5$S (M+H)+ 492.13545. found 492.13568.

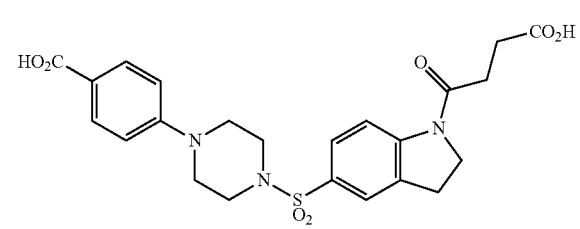 [SMILES: O=C(O)CCC(=O)N1CCc2cc(S(=O)(=O)N3CCN(c4ccc(C(=O)O)cc4)CC3)ccc21]

(XW3-002) 4-(4-(1-(3-Carboxypropanoyl)indolin-5-ylsulfonyl)piperazin-1-yl)benzoic acid XW3-002 was prepared using the same procedure as described in the preparation of XW2-011B as a brown solid (yield 25%). Decomposed at 250° C.; $^1$H NMR (400 MHz, DMSO-D$_6$) δ 12.2 (bs, 2H), 8.20 (d, J=8.0 Hz, 1H), 7.74 (d, 2H, J=8.2 Hz), 7.55-7.59 (m, 2H), 6.92 (d, J=8.3 Hz, 1H), 4.18 (t, J=8.5 Hz, 2H), 3.23 (t, J=8.4 Hz, 2H), 2.96 (bs, 6H), 2.70 (s, 2H); HRMS (ESI-ve) m/z calculated for C$_{23}$H$_{25}$N$_3$O$_7$S (M−H)−486.13404. found 486.13467.

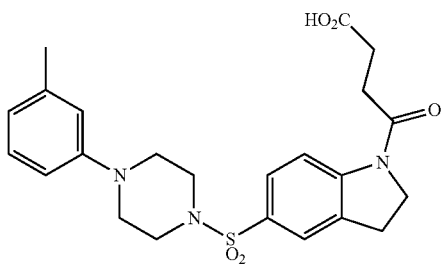 [SMILES: Cc1cccc(N2CCN(S(=O)(=O)c3ccc4c(c3)CCN4C(=O)CCC(=O)O)CC2)c1]

(XW2-057) 4-Oxo-4-(5-(4-m-tolylpiperazin-1-ylsulfonyl)indolin-1-yl)butanoic acid XW2-057 was prepared using the same procedure as described for the preparation of XW2-011B as an off-white solid (yield 64%). Mp=255-257° C.; $^1$H NMR (400 MHz, CDCl$_3$) δ 8.27 (d, J=8.0 Hz, 1H), 7.58 (d, J=8.0 Hz, 1H), 7.52 (s, 1H), 7.07 (t, 1H, J=7.9 Hz), 6.63 (m, 3H), 4.13 (t, 2H, J=8.6 Hz), 3.23 (t, 2H, J=8.5 Hz), 3.15 (bs, 4H), 3.08 (bs, 4H), 2.73 (bs, 4H), 2.23 (s, 3H); HRMS (ESI-ve) m/z calculated for C$_{23}$H$_{26}$N$_3$O$_5$S (M+H)+456.15987. found 456.16067.

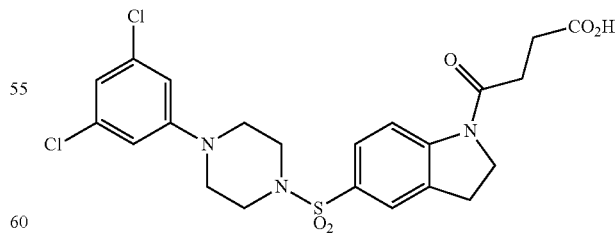

(XW2-124B) 4-(5-(4-(3,5-Dichlorophenyl)piperazin-1-ylsulfonyl)indolin-1-yl)-4-oxobutanoic acid XW2-124B was prepared using the same procedure as described for the preparation of XW2-011B as a white solid (yield 88%). Decomposed at 250° C.; $^1$H NMR (400 MHz, CDCl$_3$) δ 8.20 (d, J=8.0 Hz, 1H), 7.53-7.55 (m, 2H), 6.90 (s, 2H), 6.85 (s, 1H), 4.19 (t, J=8.5 Hz, 2H), 3.28 (bs, 4H), 3.20 (t, J=8.4 Hz, 2H), 2.92 (bs, 4H), 2.59 (t, J=6.4 Hz4H), 2.30 (t, J=6.8 Hz, 2H); HRMS (ESI-ve) m/z calculated for $C_{22}H_{24}Cl_2N_3O_5S$ (M+H)+511.08082. found 511.08076.

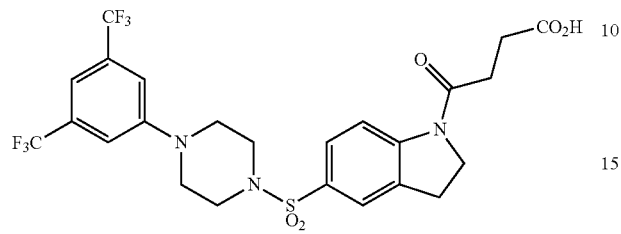

(XW2-119) 4-(5-(4-(3,5-Bis(trifluoromethyl)phenyl)piperazin-1-ylsulfonyl)indolin-1-yl)-4-oxobutanoic acid XW2-119 was prepared using the same procedure as described in the preparation of XW2-011B as a white solid (yield 84%). Mp=206-207° C.; $^1$H NMR (400 MHz, DMSO-D$_6$) δ 8.19 (d, J=8.0 Hz, 1H), 7.59 (s, 1H), 7.57 (d, J=8.0 Hz, 1H), 7.43 (s, 2H), 7.30 (s, 1H), 4.17 (t, J=8.5 Hz, 2H), 3.42 (bs, 4H), 3.24 (t, J=8.4 Hz, 2H), 2.97 (bs, 4H), 2.70 (s, 4H), 2.69 (t, J=6.8 Hz, 2H), 2.49 (t, J=6.4 Hz, 2H); HRMS (ESI-ve) m/z calculated for $C_{24}H_{24}F_6N_3O_5S$ (M+H)+ 580.13354. found 580.13313.

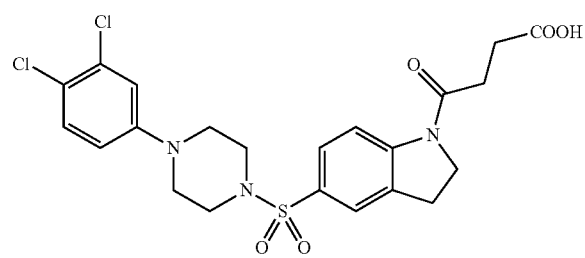 [SMILES: O=C(O)CCC(=O)N1CCc2cc(S(=O)(=O)N3CCN(c4ccc(Cl)c(Cl)c4)CC3)ccc21]

(XW2-036) 4-(5-(4-(3,4-Dichlorophenyl)piperazin-1-ylsulfonyl)indolin-1-yl)-4-oxobutanoic acid XW2-036 was prepared using the same procedure as described for the preparation of XW2-011B as a white solid (yield 51%). Decomposed at 250° C. $^1$H NMR (400 MHz, DMSO-D$_6$) δ 8.22 (d, J=8.0 Hz, 1H), 7.60 (s, 1H), 7.57 (d, J=8.0 Hz, 1H), 7.38 (d, J=8.9 Hz, 1H), 7.11 (d, J=2.6 Hz, 1H), 6.90 (dd, J=2.6, 9.0 Hz, 1H), 4.19 (t, J=8.5 Hz, 2H), 3.26 (bs, 8H), 2.96 (s, 4H), 2.71 (s, 2H); HRMS (ESI-ve) m/z calculated for $C_{22}H_{22}Cl_2N_3O_5S$ (M−H)− 510.06627. found 510.06782.

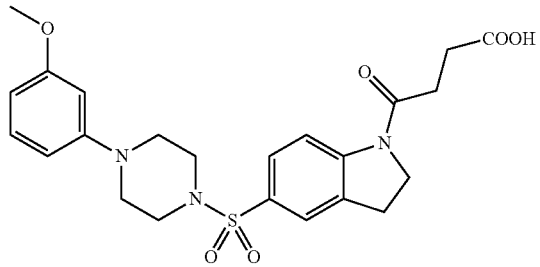 [SMILES: COc1cccc(N2CCN(S(=O)(=O)c3ccc4c(c3)CCN4C(=O)CCC(=O)O)CC2)c1]

(XW2-038F) 4-(5-(4-(3-Methoxyphenyl)piperazin-1-ylsulfonyl)indolin-1-yl)-4-oxobutanoic acid XW2-038F was prepared using the same procedure as described for the preparation of XW2-011B as an off-white solid (yield 77%). Mp=215-216° C. $^1$H NMR (400 MHz, DMSO-D$_6$) δ 8.22 (dm J=8.0 Hz, 1H), 7.60 (s, 1H), 7.57 (d, J=8.0 Hz, 1H), 7.08 (t, J=8.2, 1H), 6.47 (d, J=8.6 Hz, 1H), 6.42 (s, 1H), 6.38 (d, J=7.9 Hz, 1H), 4.20 (t, J=8.4 Hz, 2H), 3.68 (s, 3H), 3.20 (bs, 6H), 2.96 (s, 4H), 2.71 (t, J=6.0 Hz, 2H); HRMS (ESI-ve) m/z calculated for $C_{23}H_{28}N_3O_6S$ (M+H)+ 474.16933. found 474.16964.

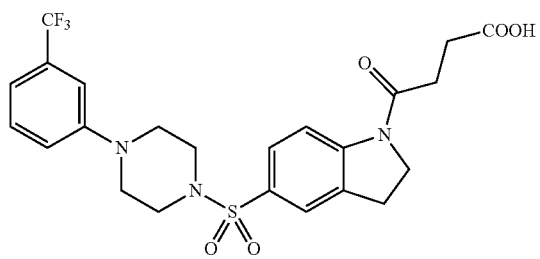

(XW2-031B) 4-oxo-4-(5-(4-(3-(trifluoromethyl)phenyl)piperazin-1-ylsulfonyl)indolin-1-yl)butanoic acid XW2-031B was prepared using the same procedure as described for the preparation of XW2-011B as a ink solid (yield 95%). Mp=218-219° C. $^1$H NMR (400 MHz, DMSO-D$_6$) δ 12.14 (bs, 1H), 8.22 (d, J=8.1 Hz, 1H), 7.61 (s, 1H), 7.57 (d, J=8.0 Hz, 1H), 7.40 (t, J=8.0 Hz, 1H), 7.18 (d, J=8.5 Hz, 1H), 7.15 (s, 1H), 7.09 (d, J=7.8, 1H), 4.20 (t, J=8.6 Hz, 2H), 3.24 (t, J=8.7 Hz, 2H), 2.99 (s, 4H), 2.71 (t, J=5.9 Hz, 2H), 2.52 (t, J=6.0 Hz, 2H); HRMS (ESI-ve) m/z calculated for $C_{23}H_{23}F_3ClN_3O_5S$ (M−H)− 510.13160. found 510.13180.

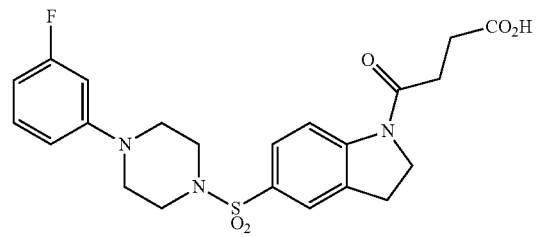

(XW2-124A) 4-(5-(4-(3-Fluorophenyl)piperazin-1-ylsulfonyl)indolin-1-yl)-4-oxobutanoic acid XW2-124A was prepared using the same procedure as described in the preparation of XW2-011B as a white solid (yield 55%). Mp=274-276° C. $^1$H NMR (400 MHz, DMSO-D$_6$) δ 8.20 (d, J=8.0 Hz, 1H), 7.52-7.55 (m, 2H), 7.17 (q, J=8.4 Hz, 1H), 6.69 (m, 2H), 6.53 (m, 1H), 4.20 (t, J=8.5 Hz, 2H), 3.17-3.24 (m, 6H), 2.94 (bs, 4H), 2.54 (t, J=6.4 Hz, 2H), 2.22 (1, J=6.8 Hz, 2H); HRMS (ESI-ve) m/z calculated for C$_{22}$H$_{25}$FN$_3$O$_5$S (M+H)+ 461.14935. found 461.14921.

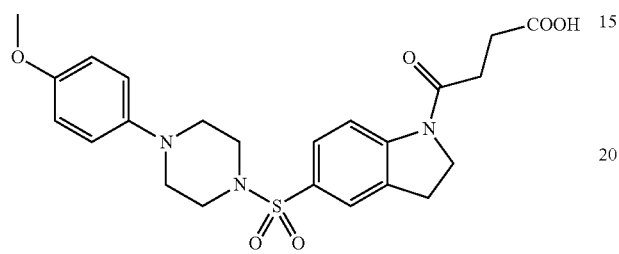

(XW2-038E) 4-(5-(4-(4-Methoxyphenyl)piperazin-1-ylsulfonyl)indolin-1-yl)-4-oxobutanoic acid XW2-038E was prepared using the same procedure as described FOR the preparation of XW2-011B as a white solid (yield 82%). Decomposed at 250° C. $^1$H NMR (400 MHz, DMSO-D$_6$) δ 8.23 (d, J=7.1, 1H), 7.56 (m, 2H), 6.85 (d, J=9.1, 2H), 6.79 (d, J=9.1, 2H), 4.22 (t, J=8.4, 2H), 3.66 (s, 3H), 3.23 (t, J=8.3, 2H), 3.06 (s, 4H), 2.97 (s, 4H), 2.61 (t, J=6.1, 2H), 2.31 (t, J=6.7, 2H); HRMS (ESI-ve) m/z calculated for C$_{23}$H$_{28}$N$_3$O$_6$S (M+H)+ 474.16933. found 474.17042.

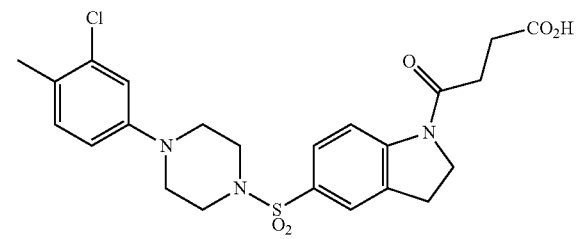 [SMILES: Cc1ccc(N2CCN(S(=O)(=O)c3ccc4c(c3)CCN4C(=O)CCC(=O)O)CC2)cc1Cl]

(XW3-006) 4-(5-(4-(3-Chloro-4-methylphenyl)piperazin-1-ylsulfonyl)indolin-1-yl)-4-oxobutanoic acid XW3-006 was prepared using the same procedure as described for the preparation of XW2-011B as an off-white solid (yield 86%). Decomposed at 250° C. $^1$H NMR (400 MHz, DMSO-D$_6$) δ 8.20 (d, J=8.0 Hz, 1H), 7.53-7.56 (m, 2H), 7.12 (d, J=8.4 Hz, 1H), 6.90 (d, J=2.4 Hz, 1H), 6.77 (dd, J=2.4, 8.4 Hz, 1H), 4.20 (t, J=8.5 Hz, 2H), 3.18 (bs, 6H), 2.93 (bs, 4H), 2.60 (bs, 2H), 2.30 (t, J=6.8 Hz, 2H), 2.17 (s, 3H); HRMS (ESI-ve) m/z calculated for C$_{23}$H$_{27}$ClN$_3$O$_5$S (M+H)+ 492.13545. found 492.13577.

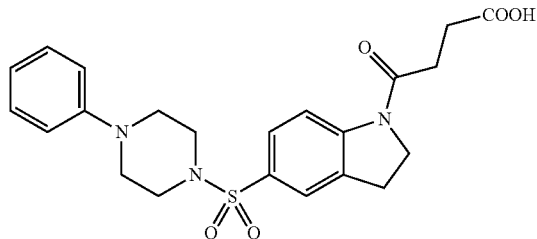 [SMILES: O=C(O)CCC(=O)N1CCc2cc(S(=O)(=O)N3CCN(c4ccccc4)CC3)ccc21]

(XW2-038A) 4-oxo-4-(5-(4-Phenylpiperazin-1-ylsulfonyl)indolin-1-yl)butanoic acid XW2-038A was prepared using the same procedure as described for the preparation of XW2-011B as a white solid (yield 64%). Mp=221-223° C. $^1$H NMR (400 MHz, CDCl$_3$) δ 8.34 (d, J=8.3 Hz, 1H), 7.63 (d, J=8.3 Hz, 1H), 7.58 (s, 1H), 7.26 (m, 2H), 6.87 (m, 3H), 4.19 (t, J=8.5 Hz, 2H), 3.30 (t, J=8.4 Hz, 2H), 3.24 (bs, 4H), 3.16 (bs, 4H), 2.79 (s, 4H); HRMS (ESI-ve) m/z calculated for C$_{22}$H$_{26}$ClN$_3$O$_5$S (M+H)+ 444.15877. found 444.15878.

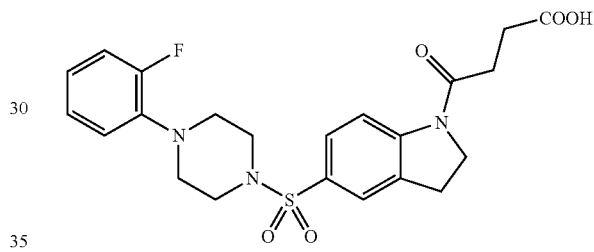

(XW2-038D) 4-(5-(4-(2-Fluorophenyl)piperazin-1-ylsulfonyl)indolin-1-yl)-4-oxobutanoic acid XW2-0380 was prepared using the same procedure as described for the preparation of XW2-011B as a pink solid (yield 36%). Mp=228-230° C. $^1$H NMR (400 MHz, DMSO-D$_6$) δ 12.13 (bs, 1H), 8.23 (d, J=8.4 Hz, 1H), 7.61 (s, 1H), 7.59 (d, 8.5 Hz, 1H), 7.06 (m, 4H), 4.20 (d, J=8.6 Hz, 2H), 3.27 (t, J=8.5 Hz, 2H), 3.07 (s, 4H), 3.01 (s, 4H), 2.72 (s, 2H), 2.54 (t, J=6.6 Hz, 2H); HRMS (ESI-ve) m/z calculated for C$_{22}$H$_{25}$FN$_3$O$_5$S (M+H)+ 462.14935. found 462.14984.

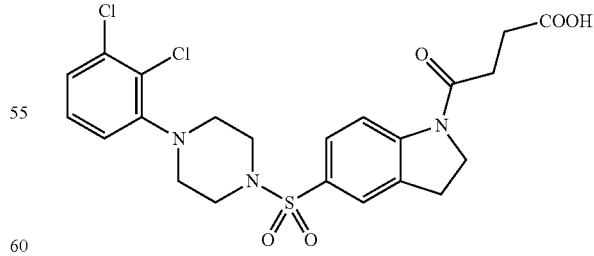

(XW2-038G) 4-(5-(4-(2,3-Dichlorophenyl)piperazin-1-ylsulfonyl)indolin-1-yl)-4-oxobutanoic acid XW2-038D was prepared using the same procedure as described for the preparation of XW2-011B as a white solid (yield 59%). Mp=240-242. $^1$H NMR (400 MHz, DMSO-D$_6$) δ 8.24 (d, J=8.2 Hz, 1H), 7.62 (s, 1H), 7.60 (d, J=8.5 Hz, 1H), 7.32 (m, 2H), 7.17 (dd, J=3.6, 6.1 Hz, 1H), 4.22 (t, J=8.6, 2H), 3.27 (t, J=8.0 Hz, 2H), 3.04 (bs, 8H), 2.73 (t, 2H, J=6.1), 2.53 (t, J=6.0 Hz, 2H): HRMS (ESI-ve) m/z calculated for C$_{22}$H$_{24}$Cl$_2$N$_3$O$_5$S (M+H)+ 512.08082. found 512.08044.

Scheme 2.

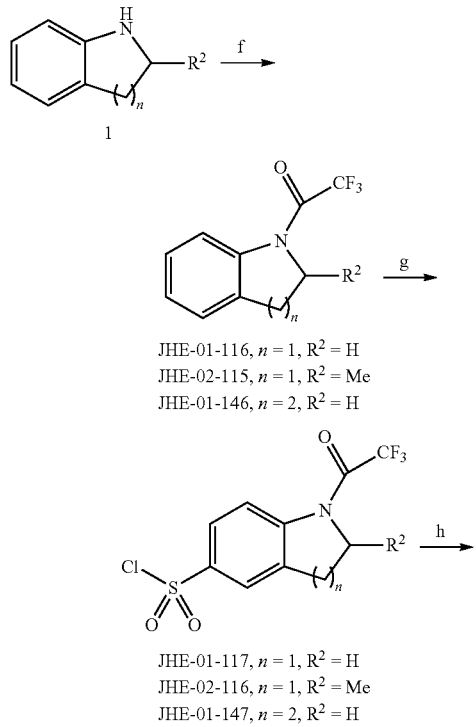

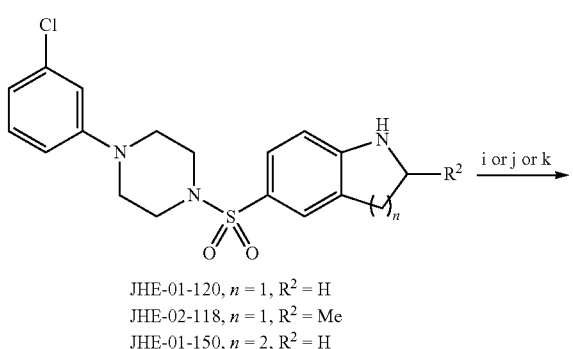

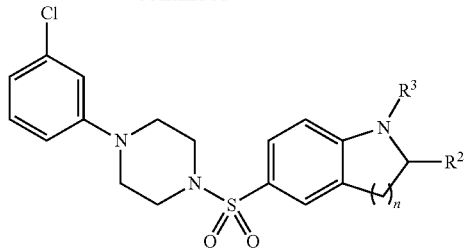

Reagents and conditions: (f) trifluoroacetic anhydride, DCM, 0° C., 1 hr; (g) chlorosulfonic acid, 0-70° C., 45 min; (h) 1-(3-chlorophenyl)piperazine, pyridine, DCE, microwave, 150° C., 15 min; (d) 1N NaOH, THF, rt, 18 hr; (i) acid chloride, Et$_3$N, DCM, microwave, 80° C.; (j) isocyanates, THF, microwave, 100° C., 20 min; (k) anhydrides, chloroform, 100° C., 30 min.

Starting from indoline (1), the NH group was first protected as its trifluoroacetamide. Following Carlier's procedure (*J. Org. Chem.* 1988, 2047-52), N-trifluoroacetylindoline JHE-01-116 next underwent sulfonation at the para-5-position by treatment with chlorosulfonic acid. The resulting chlorosulfonylindoline JHE-01-117 was coupled with 1-(3-chlorophenyl)piperazine to afford indoline JHE-01-119. After deprotection, indoline JHE-01-120 was obtained, which could be used directly to next reaction without purification. JHE-01-118 (when R$^2$=Me) and JHE-01-150 (when n=2) were synthesized in a similar fashion. The following coupling reactions were carried with a variety of acid chlorides, isocyanates and anhydrides.

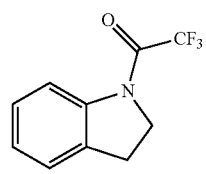

(JHE-01-116) 2,2,2-Trifluoro-1-(indolin-1-yl)ethanone WO 2005/123748

To a solution of indoline (2.0 mL, 17.7 mmol) in anhydrous dichloromethane (18 mL) at 0° C., trifluoroacetic anhydride (5.0 mL, 35.3 mmol) was added drop-wise over 5 minutes. After stirring for another 1 hr, the reaction was quenched with water at 0° C. The mixture was extracted with dichloromethane and the organic layer was washed with NaHCO$_3$ (sat. sol.) and brine. After concentration, the solid was washed with hexane to afford crude product (4.04 g, 100%). $^1$H NMR (400 MHz, CDCl$_3$) δ 8.21 (d, J=8.8 Hz, 1H), 7.28 (m, 2H), 7.16 (t, J=7.1 Hz, 1H), 4.29 (t, J=8.3 Hz, 2H), 3.27 (t, J=8.3 Hz, 2H)

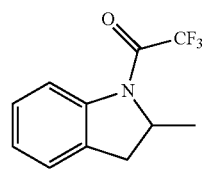 [SMILES: CC1Cc2ccccc2N1C(=O)C(F)(F)F]

(JHE-02-115) 2,2,2-Trifluoro-1-(2-methylindolin-1-yl)ethanone

JHE-02-115 was prepared from 2-methylindoline using the same procedure as described for the preparation of JHE- 01-116. Yield 100%; ¹H NMR (400 MHz, CD3CN) δ 8.05 (d, J=8.0 Hz, 1H), 7.38 (d, J=7.4 Hz, 1H), 7.32 (t, J=7.7 Hz, 1H), 7.23 (t, J=7.4, 1H), 4.86 (t, J=6.4 Hz, 1H), 3.47 (dd, J=8.0, 15.7 Hz, 1H), 2.78 (d, J=15.8 Hz, 1H), 1.30 (d, J=6.4 Hz, 3H).

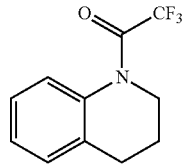 [SMILES: O=C(N1CCCc2ccccc21)C(F)(F)F]

(JHE-01-146) 1-(3,4-Dihydroquinolin-1(2H)-yl)-2,2,2-trifluoroethanone

JHE-01-146 was prepared from 1,2,34-tetrahydroquinoline using the same procedure as described for the preparation of JHE-01-116. Yield 100%; ¹H NMR (400 MHz, CDCl₃) δ 7.75 (bs, 1H), 7.18-7.25 (m, 3H), 3.84 (t, J=6.4 Hz, 2H), 2.88 (bs, 2H), 2.08 (bs, 2H).

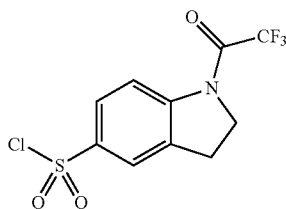 [SMILES: O=C(N1CCc2cc(S(=O)(=O)Cl)ccc21)C(F)(F)F]

(JHE-01-117) 1-(2,2,2-trifluoroacetyl)indoline-5-sulfonyl chloride (*J. Org. Chem.* 1988, 2051)

The product JHE-01-116 (5.07 g, 23.6 mmol) was added to chlorosulfonic acid (7.8 mL, 118.0 mmol) drop-wise at 0° C. over 15 minutes. After addition the reaction was slowly warmed to room temperature over 30 minutes and then heated to 70° C. for 2.5 hours. After cooling down, the solid was filtered and washed with water to afford crude product JHE-01-117 (6.17 g, 84%). ¹H NMR (400 MHz, CDCl₃) δ 8.42 (d, J=8.7 Hz, 1H), 7.99 (d, J=8.7 Hz, 1H) 7.92 (s, 1H), 4.43 (t, J=8.4 Hz, 1H), 3.40 (t, J=8.3 Hz, 2H).

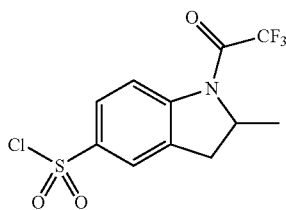 [SMILES: CC1Cc2cc(S(=O)(=O)Cl)ccc2N1C(=O)C(F)(F)F]

(JHE-02-116) 2-Methyl-1-(2,2,2-trifluoroacetyl)indoline-5-sulfonyl chloride

JHE-02-116 was prepared from JHE-02-115 using the same procedure as described for the preparation of JHE-01-117. Yield 95%; ¹H NMR (400 MHz, CD3CN) δ 8.29 (d, J=9.2 Hz, 1H), 8.06 (s, 1H), 8.04 (d, J=8.7 Hz, 1H), 4.99 (m, 1H), 3.55 (dd, J=8.2, 16.4 Hz, 1H), 2.93 (d, J=16.2 Hz, 1H), 1.34 (d, J=6.4 Hz, 3H).

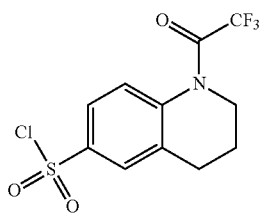 [SMILES: O=C(N1CCCc2cc(S(=O)(=O)Cl)ccc21)C(F)(F)F]

JHE-01-147) 1-(2,2,2-Trifluoroacetyl)-1,2,3,4-tetrahydroquinoline-6-sulfonyl chloride JHE-01-147 was prepared from JHE-01-146 using the same procedure as described in the preparation of JHE-01-117. Yield 79%; ¹H NMR (400 MHz, CDCl₃) δ 7.99 (d, J=8.6 Hz, 1H), 7.89 (m, 2H), 3.91 (t, J=6.0 Hz, 2H), 3.02 (t, J=6.8 Hz, 2H), 2.16 (m, 2H).

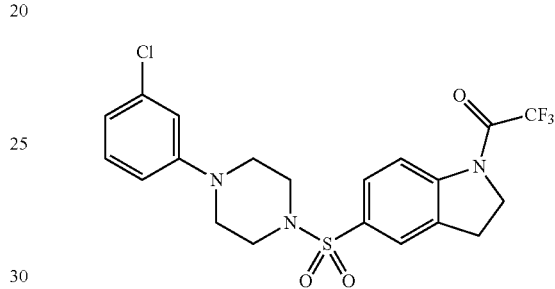

(JHE-01-119) 1-(5-(4-(3-Chlorophenyl)piperazin-1-ylsulfonyl)indolin-1-yl)-2,2,2-trifluoroethanone To a solution of JHE-01-117 (325 mg, 1.65 mmol) in dichloromethane (6 mL) was added 1-(3-chlorophenyl)piperazine (517 g, 1.65 mmol) and pyridine (0.4 mL, 4.96 mmol) at room temperature. The reaction mixture was irradiated in microwave reactor at 150° C. for 15 minutes and then the mixture was concentrated. The resulting solid was washed with water to afford JHE-01-119 (678 mg, 86%). ¹H NMR (400 MHz, CD3CN) δ 8.30 (d, J=8.2 Hz, 1H), 7.71 (m, 2H), 7.20 (t, J=8.0 Hz, 1H), 6.91 (t, J=2.0 Hz, 1H), 6.84 (m, 2H), 4.37 (t, J=8.2 Hz, 2H), 3.35 (t, J=8.2 Hz, 2H), 3.27 (t, J=4.2 Hz, 4H), 3.09 (t, J=4.0 Hz, 4H)

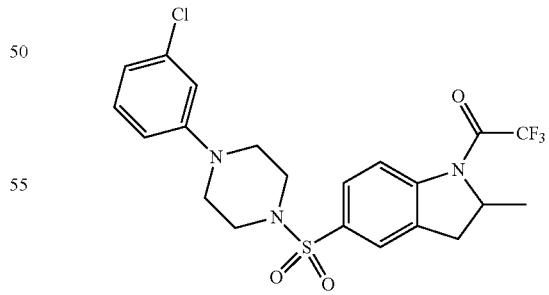

(JHE-02-117) 1-(5-(4-(3-chlorophenyl)piperazin-1-ylsulfonyl)-2-methylindolin-1-yl)-2,2,2-trifluoroethanone JHE-02-117 was prepared from JHE-02-116 using the same procedure as described for the preparation of JHE-01-

119 as an off-white solid (yield 86%). Mp=174-175° C.; $^1$H NMR (CD$_3$CN, 400 MHz) δ 8.22 (d, J=8.4 Hz, 1H), 7.76 (s, 1H), 7.73 (d, J=8.4 Hz, 1H), 7.21 (dd, J=8.0 Hz, 8.0 Hz, 1H), 6.92 (dd, J=2.2 Hz, 2.2 Hz, 1H), 6.86-6.82 (m, 2H), 4.98-4.91 (m, 1H), 3.52 (dd, J=15.8 Hz, 8.0 Hz, 1H), 3.27 (t, J=5.2 Hz, 3H), 3.11 (t, J=5.2 Hz, 3H), 2.88 (d, J=15.8 Hz, 1H), 1.32 (d, J=6.4 Hz, 3H); HPLC 98% [t$_R$=10.53, 70% acetonitrile in water (0.1% TFA)]; HPLC 98% (t$_R$=29.53, 70% methanol in water (0.1% TFA)).

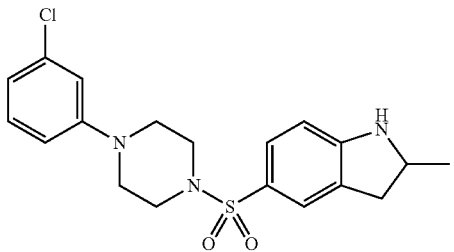

(JHE-02-118) 5-(4-(3-Chlorophenyl)piperazin-1-ylsulfonyl)-2-methylindoline

JHE-02-118 was prepared from JHE-02-117 using the same procedure as described for the preparation of JHE-01-120. Yield 100%; $^1$H NMR (400 MHz, CD3CN) δ 7.38 (m, 2H), 7.20 (t, J=8.1 Hz, 1H), 6.91 (t, J=2.1 Hz, 1H), 6.83 (ddd, J=1.7, 3.7, 7.1 Hz, 2H), 6.58 (d, J=8.6 Hz, 1H), 5.17 (s, NH), 4.07 (m, 1H), 3.25 (m, 4H), 3.19 (m, 1H), 3.01 (m, 4H), 2.64 (dd, J=7.4, 16.1 Hz, 1H), 1.25 (d, J=6.2 Hz, 3H)

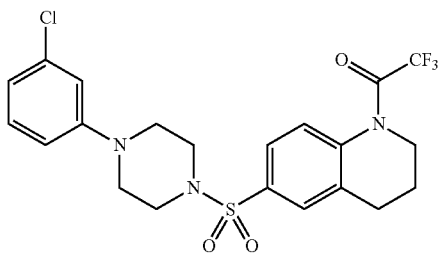 [SMILES: O=C(N1CCCc2cc(S(=O)(=O)N3CCN(c4cccc(Cl)c4)CC3)ccc21)C(F)(F)F]

(JHE-01-148) 1-(6-(4-(3-Chlorophenyl)piperazin-1-ylsulfonyl)-3,4-dihydroquinolin-1(2H)-yl)-2,2,2-trifluoroethanone JHE-01-148 was prepared from JHE-01-147 using the same procedure as described for the preparation of JHE-01-119. Yield 86%; $^1$H NMR (400 MHz, CD3CN) δ 7.89 (d, J=7.0 Hz, 1H), 7.67 (s, 1H), 7.63 (d, J=9.0 Hz, 1H), 7.21 (t, J=8.1 Hz, 1H), 6.92 (s, 1H), 6.85 (s, 2H), 3.87 (t, J=6.0 Hz, 2H), 3.27 (t, J=4.8 Hz, 4H), 3.10 (t, J=4.8 Hz, 4H), 2.97 (t, J=6.4 Hz, 2H), 2.09 (m, 2H)

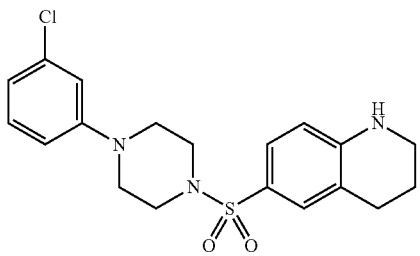

(JHE-01-150) 6-(4-(3-Chlorophenyl)piperazin-1-ylsulfonyl)-1,2,3,4-tetrahydroquinoline JHE-01-150 was prepared from JHE-01-148 using the same procedure as described for the preparation of JHE-01-120. Yield 100%; $^1$H NMR (400 MHz, CD3CN) δ 7.28 (m, 2H), 7.20 (t, 1H, J=8.1 Hz), 6.91 (s, 1H), 6.84 (m, 2H), 6.54 (d, 1H, J=9.1 Hz), 5.29 (s, NH), 3.30 (m, 2H), 3.25 (t, J=4.8 Hz, 4H), 3.00 (t, J=5.2 Hz, 4H), 2.77 (t, 2H, J=6.2 Hz), 1.87 (m, 2H)

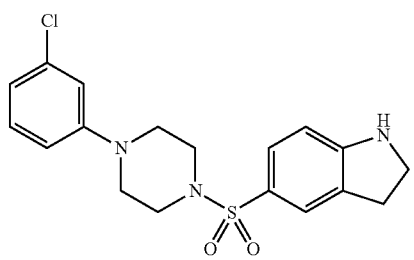 [SMILES: O=S(=O)(c1ccc2c(c1)CCN2)N1CCN(c2cccc(Cl)c2)CC1]

(JHE-01-120) 5-(4-(3-Chlorophenyl)piperazin-1-ylsulfonyl)indoline

To a solution of JHE-01-119 (265 mg, 0.56 mmol) in tetrahydrofuran (1 mL) was added NaOH (1.0 M in H$_2$O, 2 mL). The reaction was stirred overnight. After concentration, the solid was washed with water to afford the indoline JHE-01-120 (204 mg, 97%). $^1$H NMR (400 MHz, CD3CN) δ 7.39 (m, 2H), 7.20 (t, J=8.1 Hz, 1H), 6.91 (s, 1H), 6.84 (t, J=7.1 Hz, 2H), 6.62 (d, J=8.0 Hz, 1H), 5.05 (s, NH), 3.62 (t, J=8.7 Hz, 2H), 3.25 (t, J=4.8 Hz, 4H), 3.04 (m, 6H)

Scheme 3

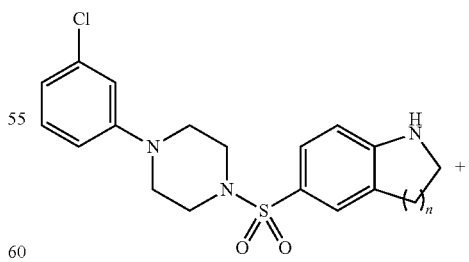

JHE-01-120, n = 1
JHE-01-150, n = 2

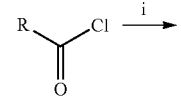

-continued

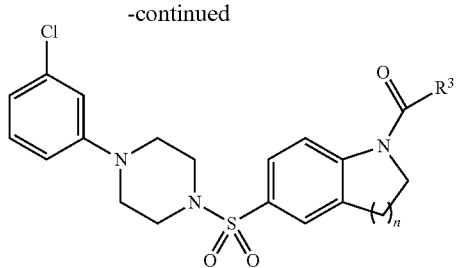

JF020, n = 1, R³ = 3-ClPh
JF021, n = 1, R³ = 4-ClPh
JF022, n =1, R³ = Ph
JF023, n = 1, R³ = 3,4-DiClPh
JF024, n = 1, R³ = 2,4-DiClPh
JF024, n = 1, R³ = 3,5-DiClPh
JF026, n = 1, R³ = CycloPentane
JF027, n = 1, R³ = CycloPropane
JF028, n = 1, R³ = 4-MeOPh
JF031, n = 1, R³ = Bn
JHE-02-035, n = 1, R³ = 3-MeOPh
JHE-02-33A, n = 1, R³ = n-Pr
JHE-02-033B, n = 1, R³ = i-Bu
JHE-02-063B, n = 1, R³ = 4-ClPh
JHE-01-169, n = 1, R³ = CH₂OCH₃
JHE-01-155B, n = 1, R³ = CO₂H
JHE-02-023, n = 2, R³ = CH₂CH₂CO₂H JHE-01-179, n = 1, R² = [dioxolanone group]

JHE-02-001, n = 1, R² = [hydroxy diacid group]

Reagents and conditions: (i) acid chloride, Et₃N, DCM, microwave, 80° C; (1) AcOH, THF, H₂O 450° C., 7 hr.

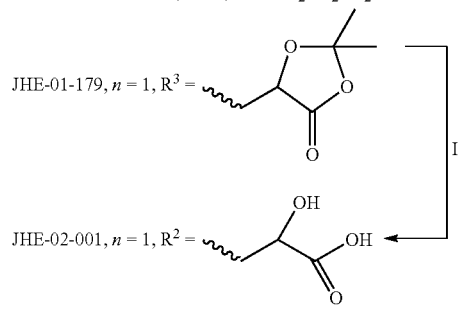

(JF028) (5-(4-(3-Chlorophenyl)piperazin-1-ylsulfonyl)indolin-1-yl)(4-methoxyphenyl)methanone In a microwave reaction tube equipped with a magnetic stirring bar, JHE-01-120 (54.0 mg, 0.143 mmol) was dissolved in dichloromethane (0.5 mL) at room temperature. To the solution was added triethylamine (18.3 µl, 0.143 mmol) and 4-methoxybenzyl chloride (24 mg, 0.143 mmol). The reaction tube was capped and irradiated in the microwave reactor (Biotage Initiator I) at 80° C. for 20 minutes. After concentration the solid product was purified by washing with water to provide JF028 as an off-white solid yield 95%. Mp=193-194° C.; ¹H NMR (DMSO-d₆, 400 MHz) δ 7.92 (s, br, 1H), 7.63-7.58 (m, 2H), 7.18 (dd, J=8.0 Hz, 8.0 Hz, 1H), 7.01 (d, J=8.0 Hz, 2H), 6.91 (dd, J=2.0 Hz, 2.0 Hz, 1H), 6.85 (dd, J=8.0 Hz, 2.0 Hz, 1H), 6.78 (dd, J=8.0 Hz, 2.0 Hz, 1H), 6.77 (d, J=7.6 Hz, 1H), 4.11 (t, J=8.4 Hz, 2H), 3.81 (s, 3H), 3.27-3.24 (m, 4H), 3.16 (t, J=8.4 Hz, 2H), 2.96-2.94 (m, 4H); HPLC 94% (t$_R$=7.25, 70% acetonitrile in water (0.1% TFA)); HPLC 97% [t$_R$=10.57, 70% methanol in water (0.1% TFA)]; HRMS (ESI-ve) m/z calcd. for C₂₆H₂₇ClN₃O₄S, 512.1405 (M+H)⁺. found 512.1410 (M+H)⁺.

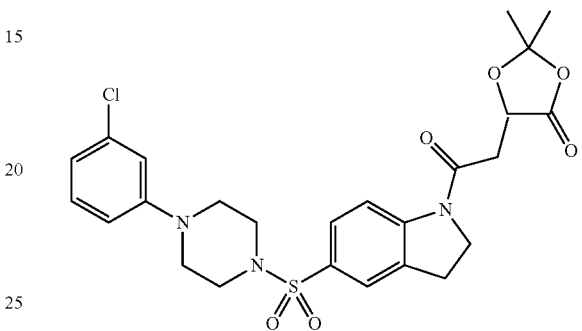

(JHE-01-179) 5-(2-(5-(4-(3-Chlorophenyl)piperazin-1-ylsulfonyl)indolin-1-yl)-2-oxoethyl)-2,2-dimethyl-1,3-dioxolan-4-one JHE-01-179 was prepared from JHE-01-120 and 2-(2,2-dimethyl-5-oxo-1,3-dioxolan-4-yl)acetyl chloride (converted from the corresponding acid) using the same procedure as described for the preparation of JF028. The product was purified by column chromatography (ethyl acetate:hexane, 2:3) to give a dark brown solid, yield 85%. ¹H NMR (CD₃CN, 400 MHz) δ 8.29 (d, J=8.3 Hz, 1H), 7.61 (d, J=8.5 Hz, 2H), 7.20 (t, J=8.1 Hz, 1H), 6.91 (t J=2.1 Hz, 1H), 6.83 (m, 2H), 4.85 (dd, J=3.6, 5.6 Hz, 1H), 4.18 (t, J=8.4 Hz, 2H), 3.26 (m, 6H), 3.06 (m, 6H), 1.62 (s, 3H), 1.58 (s, 3H)

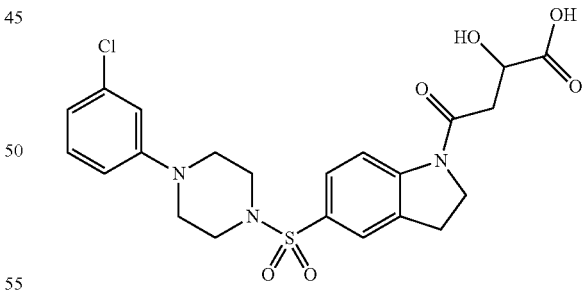

(JHE-02-001) 4-(5-(4-(3-Chlorophenyl)piperazin-1-ylsulfonyl)indolin-1-yl)-2-hydroxy-4-oxobutanoic acid At room temperature. JHE-01-179 (118 mg, 0.033 mmol) was mixed with acetic acid (4 mL), THF (1 mL) and water (2 mL) in a round bottom flask. The reaction mixture was heated to 45° C. for 7 hours. After concentration, the residue was triturated with water. The precipitate was filtered and washed with dichloromethane, acetonitrile and methanol. JHE-02-

001: Off white solid, yield 70%. Mp=190-191° C.; $^1$H NMR (DMSO-$d_6$, 400 MHz) δ 8.21 (d, J=8.0 Hz, 1H), 7.58-7.55 (m, 2H), 7.17 (dd, J=8.0 Hz, 8.0 Hz, 1H), 6.90 (1H, s), 6.84 (d, J=8.0 Hz, 1H), 6.78 (d, J=8.0 Hz, 1H), 4.39 (t, J=8.0 Hz, 1H), 4.18 (t, J=8.0 Hz, 2H), 3.23 (m, 6H), 2.94 (m, 4H), 2.88-2.75 (m, 2H); HRMS (ESI-ve) m/z calcd. for $C_{22}H_{25}ClN_3O_6S$, 494.1147 (M+H)$^+$. found 494.1147 (M+H)$^+$.

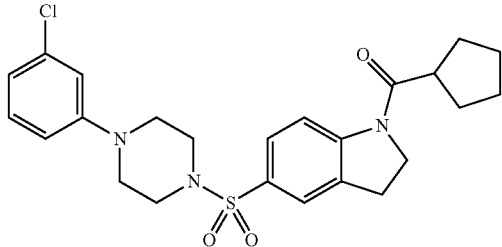 [SMILES: O=C(C1CCCC1)N1CCc2cc(S(=O)(=O)N3CCN(c4cccc(Cl)c4)CC3)ccc21]

(JF026) (5-(4-(3-Chlorophenyl)piperazin-1-ylsulfonyl)indolin-1-yl)(cyclopentyl)methanone JF026 was prepared from JHE-01-120 and cyclopentanecarbonyl chloride (converted from the corresponding acid) using the same procedure as described for the preparation of JF028. JF026: Off-white solid, yield 83%. Mp=166-167° C.; $^1$H NMR (DMSO-$d_6$, 400 MHz) δ 8.24 (d, J=8.4 Hz, 1H), 7.57 (s, 1H), 7.55 (d, J=8.4 Hz, 1H), 7.17 (dd, J=8.0 Hz, 8.0 Hz, 1H), 6.90 (dd, J=2.0 Hz, 2.0 Hz, 1H), 6.84 (dd, J=8.0 Hz, 2.0 Hz, 1H), 6.77 (dd, J=8.0 Hz, 2.0 Hz, 1H), 4.22 (t, J=8.4 Hz, 2H), 3.27-3.19 (m, 6H), 3.05-2.92 (m, 5H), 1.90-1.82 (m, 2H), 1.77-1.52 (m, 6H); HPLC 98% ($t_R$=10.05, 70% acetonitrile in water (0.1% TFA)); HPLC 99% [$t_R$=12.61, 70% methanol in water (0.1% TFA)]; HRMS (ESI-ve) m/z calcd. for $C_{24}H_{29}ClN_3O_3S$, 476.1613 (M+H)$^+$. found 476.1621 (M+H)$^+$.

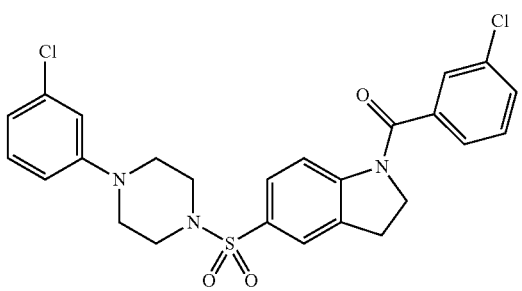 [SMILES: O=C(c1cccc(Cl)c1)N1CCc2cc(S(=O)(=O)N3CCN(c4cccc(Cl)c4)CC3)ccc21]

(JF020) (3-Chlorophenyl)(5-(4-(3-chlorophenyl)piperazin-1-ylsulfonyl)indolin-1-yl)methanone J1020 was prepared from JHE-01-120 and 3-chlorobenzoyl chloride (converted from the corresponding acid) using the same procedure as described in the preparation of JF028. JF020: Off-white solid, yield 92%. Mp=221-222° C.; $^1$H NMR (DMSO-$d_6$, 400 MHz) δ 8.14 (s, br, 1H), 7.67-7.50 (m, 6H), 7.18 (dd, J=8.0 Hz, 8.0 Hz, 1H), 7.01 (d, J=8.0 Hz, 2H), 6.91 (dd, J=2.0 Hz, 2.0 Hz, 1H), 6.87 (dd, J=8.0 Hz, 2.0 Hz, 1H), 6.78 (dd, J=8.0 Hz, 2.0 Hz, 1H), 4.04 (t, J=8.4 Hz, 2H), 3.29-3.24 (m, 4H), 3.16 (t, J=8.4 Hz, 2H), 2.96-2.94 (m, 4H); HPLC 98% [$t_R$=9.58, 70% acetonitrile in water (0.1% TFA)]; HRMS (ESI-ve) m/z calcd. for $C_{25}H_{24}Cl_2N_3O_3S$, 516.0910 (M+H)$^+$. found 516.0935 (M+H)$^+$.

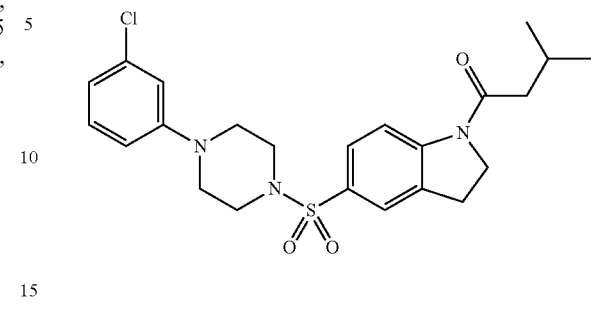

(JHE-02-033B) 1-(5-(4-(3-Chlorophenyl)piperazin-1-ylsulfonyl)indolin-1-yl)-3-methylbutan-1-one JHE-02-033B was prepared from JHE-01-120 and 3-methylbutanoyl chloride (converted from the corresponding acid) using the same procedure as described for the preparation of JF028. JHE-02-033B: off-white solid, yield 86%. Mp=162-163° C.; $^1$H NMR (CD$_3$CN, 400 MHz) δ 8.30 (d, J=8.8 Hz, 1H), 7.60-7.58 (m, 2H), 7.20 (dd, J=8.0 Hz, 8.0 Hz, 1H), 6.91 (dd, J=2.0 Hz, 2.0 Hz, 1H), 6.85-6.82 (m, 2H), 4.16 (t, J=8.4 Hz, 2H), 3.27-3.22 (m, 6H), 3.07 (t, J=5.2 Hz, 4H), 2.37 (d, J=6.8 Hz, 2H), 2.25-2.18 (m, 1H), 1.02 (s, 3H), 1.00 (s, 3H); HPLC 98% [$t_R$=9.61, 70% acetonitrile in water (0.1% TFA)]; HPLC 98% [$t_R$=23.81, 70% methanol in water (0.1% TFA)]; HRMS (ESI-ve) m/z calcd. for $C_{23}H_{29}ClN_3O_3S$, 462.1613 (M+H)$^+$. found 462.1613 (M×H)$^+$.

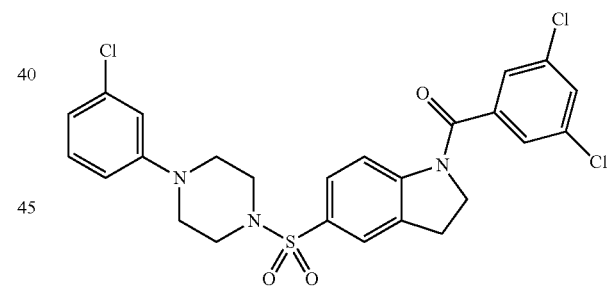

(JF025) (5-(4-(3-Chlorophenyl)piperazin-1-ylsulfonyl)indolin-1-yl)(3,5-dichlorophenyl)methanone JF025 was prepared from JHE-01-120 and 3,5-dichlorobenzoyl chloride (converted from the corresponding acid) using the same procedure as described for the preparation of JF028. JF025: off-white solid, yield 90%. Mp=262-263° C.; $^1$H NMR (DMSO-$d_6$, 400 MHz) δ 8.20 (s, br, 1H), 7.92 (s, 1H), 7.69-7.62 (m, 4H), 7.18 (dd, J=8.0 Hz, 8.0 Hz, 1H), 6.91 (d, J=2.0 Hz, 1H), 6.85 (dd, J=8.0 Hz, 2.0 Hz, 1H), 6.78 (d, J=8.0 Hz, 1H), 4.03 (t, J=8.4 Hz, 2H), 3.29-3.23 (m, 4H), 3.17 (t, J=8.4 Hz, 2H), 2.98-2.94 (m, 4H); HRMS (ESI-ve) m/z calcd. for $C_{25}H_{23}Cl_3N_3O_3S$, 550.0520 (M+H)$^+$. found 550.0518 (M+H)$^+$.

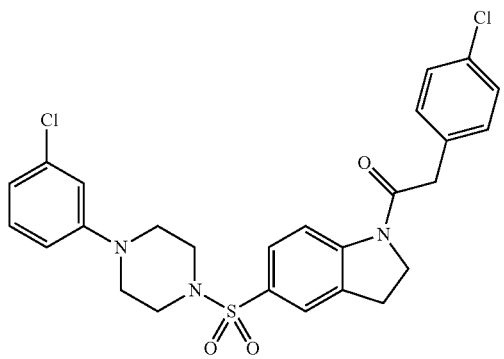 [SMILES: O=C(Cc1ccc(Cl)cc1)N1CCc2cc(S(=O)(=O)N3CCN(c4cccc(Cl)c4)CC3)ccc21]

(JHE-02-063B) 2-(4-Chlorophenyl)-1-(5-(4-(3-chlorophenyl)piperazin-1-ylsulfonyl)indolin-1-yl)ethanone JHE-02-063B was prepared from JHE-01-120 and 2-(4-chlorophenyl)acetyl chloride (converted from the corresponding acid) using the same procedure as described for the preparation of JF028. JHE-02-063B: off-white solid, yield 79%. Mp=186-187° C.; $^1$H NMR (DMSO-d$_6$, 400 MHz) δ 8.19 (d, J=8.4 Hz, 1H), 7.59 (s, 1H), 7.56 (d, J=8.4 Hz, 1H), 7.37 (d, J=8.4 Hz, 1H), 7.28 (d. J=8.4 Hz, 1H), 7.17 (dd, J=8.0 Hz, 8.0 Hz, 1H), 6.90 (dd, J=2.0 Hz, 2.0 Hz, 1H), 6.84 (dd, J=8.0 Hz, 2.0 Hz, 1H), 6.78 (dd, J=8.0 Hz, 2.0 Hz, 1H), 4.24 (t, J=8.4 Hz, 2H), 3.88 (s, 2H), 3.25-3.21 (m, 6H), 2.95-2.92 (m, 414); HPLC 99% [t$_R$=11.43, 70% acetonitrile in water (0.1% TFA)].

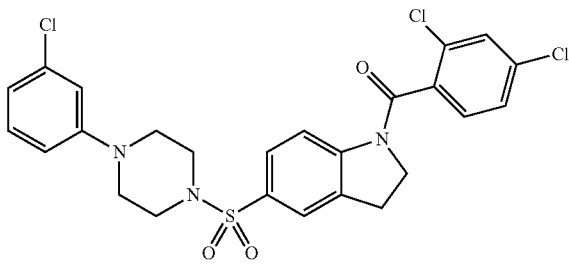 [SMILES: O=C(c1ccc(Cl)cc1Cl)N1CCc2cc(S(=O)(=O)N3CCN(c4cccc(Cl)c4)CC3)ccc21]

(JF024) (5-(4-(3-Chlorophenyl)piperazin-1-ylsulfonyl)indolin-1-yl)(2,4-dichlorophenyl)methanone JF024 was prepared from JHE-01-120 and 2,4-dichlorobenzoyl chloride (converted from the corresponding acid) using the same procedure as described for the preparation of JF028. JF024: yellow solid, yield 77%. Mp=184-184.5° C.: $^1$H NMR (DMSO-d$_6$, 400 MHz) δ 8.32 (d, J=8.8 Hz, 1H), 7.81 (s, 1H), 7.68-7.57 (m, 4H), 7.18 (d, J=8.0 Hz, 1H), 6.92 (s, 1H), 6.85 (d, J=8.0 Hz, 1H), 6.79 (d, J=8.0 Hz, 1H), 3.81 (d, J=8.0 Hz, 2H), 3.27-3.17 (m, 6H), 2.99-2.94 (m, 4H); HPLC 96% [t$_R$=12.93, 70% acetonitrile in water (0.1% TFA)]; FIRMS (ESI-ve) m/z calcd. for $C_{25}H_{23}Cl_3N_3O_3S$, 550.0520 (M+H)$^+$. found 550.0525 (M+H)$^+$.

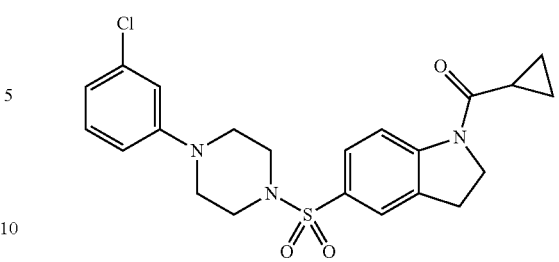

(JF027) (5-(4-(3-Chlorophenyl)piperazin-1-ylsulfonyl)indolin-1-yl)(cyclopropyl)methanone JF027 was prepared from JHE-01-120 and cyclopropanecarbonyl chloride (converted from the corresponding acid) using the same procedure as described for the preparation of JF028. JF027: Off-white solid, yield 93%. Mp=162.5-163° C.; $^1$H NMR (DMSO-d$_6$, 400 MHz) δ 8.16 (d, J=8.4 Hz, 1H), 7.58 (s, 1H), 7.34 (d, J=8.4 Hz, 1H), 7.17 (dd, J=8.0 Hz, 8.0 Hz, 1H), 6.90 (dd, J=2.0 Hz, 2.0 Hz, 1H), 6.84 (dd, J=8.0 Hz, 2.0 Hz, 1H), 6.77 (dd, J=8.0 Hz, 2.0 Hz, 1H), 4.22 (t, J=8.4 Hz, 2H), 3.27-3.19 (m, 6H), 3.05-2.92 (m, 5H), 1.90-1.82 (m, 2H), 1.77-1.52 (m, 6H); HPLC 99% (t$_R$=5.63, 70% acetonitrile in water (0.1% TFA)); HPLC 98% [t$_R$=10.10, 70% methanol in water (0.1% TFA)]; HRMS (ESI-ve) m/z calcd. for $C_{22}H_{25}ClN_3O_3S$, 446.1300 (M+H). found 446.1310 (M+H)$^+$.

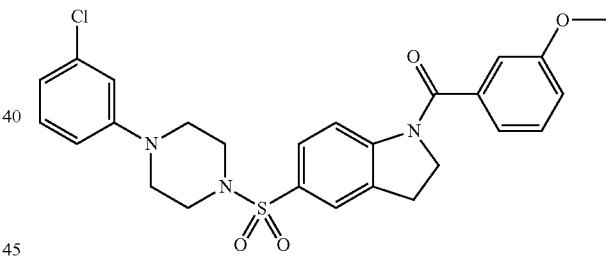

(JHE-02-035A) (5-(4-(3-chlorophenyl)piperazin-1-ylsulfonyl)indolin-1-yl)(3-methoxyphenyl)methanone JHE-02-035A was prepared from JHE-01-120 and 3-methoxybenzoyl chloride (converted from the corresponding acid) using the same procedure as described in the preparation of JF028. JHE-02-035A: Off-white solid, yield 90%. Mp=155-156° C.; $^1$H NMR (CD$_3$CN, 400 MHz) δ 7.65 (s, 1H), 7.61 (d, J=8.0 Hz, 1H), 7.30 (dd, J=7.6 Hz, 7.6 Hz, 1H), 7.21 (dd, J=8.0 Hz, 8.0 Hz, 1H), 7.14-7.09 (m, 4H), 6.92 (dd, J=2.4 Hz, 2.4 Hz, 1H), 6.86-6.82 (m, 2H), 4.09 (t, J=8.4 Hz, 2H), 3.84 (s, 3H), 3.27 (t, J=5.2 Hz, 4H), 3.20 (t, J=8.4 Hz, 2H), 3.08 (t, J=5.2 Hz, 4H); ); HPLC 98% (t$_R$=7.51, 70% acetonitrile in water (0.1% TFA)); HPLC 98% (t$_R$=19.45, 70% methanol in water (0.1% TFA)); HRMS (ESI-ve) m/z calcd. for $C_{26}H_{27}ClN_3O_4S$, 512.1405 (M+H)$^+$. found 512.1406 (M+H)$^+$.

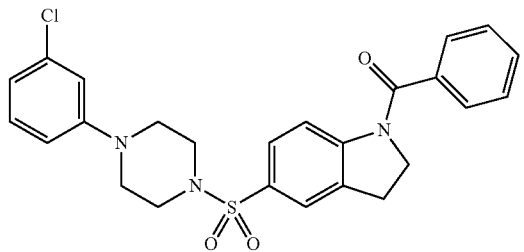 [SMILES: O=C(c1ccccc1)N1CCc2cc(S(=O)(=O)N3CCN(c4cccc(Cl)c4)CC3)ccc21]

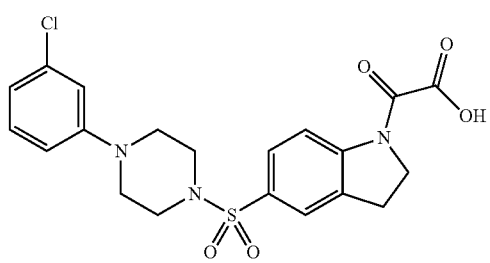

(JF022) (5-(4-(3-Chlorophenyl)piperazin-1-ylsulfonyl)indolin-1-yl)(phenyl)methanone JF022 was prepared from JHE-01-120 and benzoyl chloride (converted from the corresponding acid) using the same procedure as described for the preparation of JF028. JF022: Light brown solid, yield 87%. Mp=200-201° C.; $^1$H NMR (DMSO-d$_6$, 400 MHz) δ 7.64-7.46 (m, 8H), 7.18 (dd, J=8.0 Hz, 8.0 Hz, 1H), 6.92 (dd, J=2.0 Hz, 2.0 Hz, 1H), 6.86 (dd, J=8.0 Hz, 2.0 Hz, 1H), 6.79 (dd, J=8.0 Hz, 2.0 Hz, 1H), 4.04 (t, J=8.4 Hz, 2H), 3.27-3.24 (m, 4H), 3.16 (t, J=8.4 Hz, 2H), 2.97-2.94 (m, 4H); $^{13}$C NMR (DMSO-d$_6$, 100.6 MHz) δ 169.5, 152.2, 147.6, 137.1, 135.2, 134.5, 131.2, 129.6, 129.2, 128.4, 125.1, 119.5, 116.9, 115.9, 115.0, 51.6, 48.0, 46.3, 28.1; ); HPLC 95% [t$_R$=7.44, 70% acetonitrile in water (0.1% TFA)]; HPLC 95% [t$_R$=16.75, 70% methanol in water (0.1% TFA)]; HRMS (ESI-ve) m/z calcd. for C$_{25}$H$_{25}$ClN$_3$O$_3$S, 482.1300 (M+H)$^+$. found 482.1322 (M+H)$^+$.

(JHE-01-155B) 2-(5-(4-(3-Chlorophenyl)piperazin-1-ylsulfonyl)indolin-1-yl)-2-oxoacetic acid (JHE-01-155B) was hydrolyzed in the same fashion as JHE-01-137 from the corresponding ethyl ester which was prepared from the corresponding acid chloride and JHE-01-150 according the procedure described as for the preparation of JF028. (JHE-01-155B): off-white solid, yield 90%. Mp=219-220° C.; $^1$H NMR (DMSO-d$_6$, 400 MHz) δ 8.16 (d, J=8.8 Hz, 1H), 7.67 (s, 1H), 7.64 (d, J=8.8 Hz, 1H), 7.17 (d, J=8.4 Hz, 1H), 6.91 (s, 1H), 6.85 (d, J=8.4 Hz, 1H), 6.78 (d, J=8.4 Hz, 1H), 4.22 (t, J=8.4 Hz, 2H), 3.27-3.22 (m, 6H), 2.97-2.94 (m, 4H); HPLC 97% [t$_R$=3.47, 70% acetonitrile in water (0.1% TFA)]; HRMS (ESI-ve) m/z calcd. for C$_{20}$H$_{21}$ClN$_3$O$_5$S, 450.0885 (M+H)$^+$. found 450.0881 (M+H)$^+$.

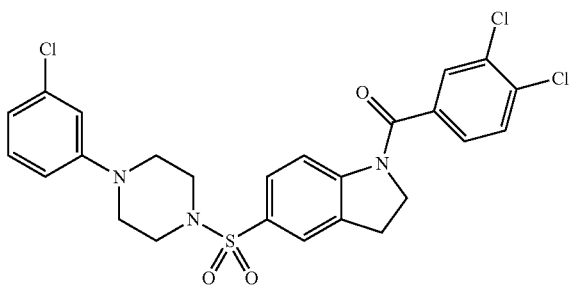 [SMILES: O=C(c1ccc(Cl)c(Cl)c1)N1CCc2cc(S(=O)(=O)N3CCN(c4cccc(Cl)c4)CC3)ccc21]

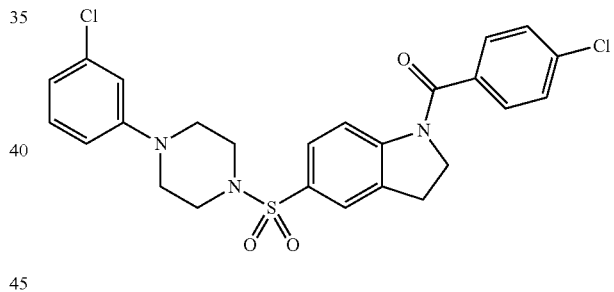

(JF023) (5-(4-(3-Chlorophenyl)piperazin-1-ylsulfonyl)indolin-1-yl)(3,4-dichlorophenyl)methanone JF023 was prepared from JHE-01-120 and 3,4-dichlorobenzoyl chloride (converted from the corresponding acid) using the same procedure as described for the preparation of JF028. JF028: Pale yellow solid, yield 27%. Mp=174-175° C.; $^1$H NMR (DMSO-d$_6$, 400 MHz) δ 7.90 (d, J=2.0 Hz, 1H), 7.90 (d, J=8.4 Hz, 1H), 7.65-7.59 (m, 3H), 7.18 (dd, J=8.4 Hz, 8.4 Hz, 1H), 6.91 (dd, J=2.0 Hz, 2.0 Hz, 1H), 6.85 (dd, J=8.4 Hz, 2.0 Hz, 1H), 6.78 (dd, J=8.4 Hz, 2.0 Hz, 1H), 4.05 (t, J=8.4 Hz, 2H), 3.26 (t, J=4.8 Hz, 4H), 3.16 (t, J=8.4 Hz, 2H), 2.95 (t, J=4.8 Hz, 4H); $^{13}$C NMR (DMSO-d$_6$, 100.6 MHz) δ 167.1, 152.2, 147.2, 137.5, 135.3, 134.5, 133.9, 132.1, 131.6, 131.2, 129.8, 128.5, 128.0, 125.2, 119.5, 117.0, 115.9, 115.0, 105.0, 51.5, 48.0, 46.3, 28.3; ); HPLC 96% [t$_R$=13.70, 70% acetonitrile in water (0.1% TFA)]; FIRMS (ESI-ve) m/z calcd. for C$_{25}$H$_{23}$Cl$_2$KN$_3$O$_3$S 554.0469 (M+K)$^+$. found 554.0470 (M+K)$^+$.

(JF021) (4-Chlorophenyl)(5-(4-(3-chlorophenyl)piperazin-1-ylsulfonyl)indolin-1-yl)methanone JF021 was prepared from JHE-01-120 and 4-chlorobenzoyl chloride (converted from the corresponding acid) using the same procedure as described in the preparation of JF028. JF021: off-white solid, yield 91%. Mp=191-192° C.; $^1$H NMR (DMSO-d$_6$, 400 MHz) δ 8.07 (s, hr, 1H), 7.64-7.55 (m, 6H), 7.18 (dd, J=8.4 Hz, 8.4 Hz, 1H), 6.91 (dd, J=2.0 Hz, 2.0 Hz, 1H), 6.85 (dd, J=8.4 Hz, 2.0 Hz, 1H), 6.78 (dd, J=8.4 Hz, 2.0 Hz, 1H), 4.05 (t, J=8.4 Hz, 2H), 3.30-3.24 (m, 4H), 3.16 (t, J=8.4 Hz, 2H), 2.96-2.94 (m, 4H); $^{13}$C NMR (DMSO-d$_6$, 100.6 MHz) δ 168.5, 152.2, 147.4, 135.9, 135.8, 135.2, 134.5, 131.2, 129.8, 129.7, 129.3, 128.5, 125.1, 119.5, 117.0, 115.9, 115.0, 51.6, 48.0, 46.3, 28.1; HPLC 97% [t$_R$=9.72, 70% acetonitrile in water (0.1% TFA)]; HRMS (ESI-ve) m/z calcd. for C$_{25}$H$_{24}$Cl$_2$N$_3$O$_3$S, 515.0910 (M+H)$^+$. found 515.0904 (M+H)$^+$.

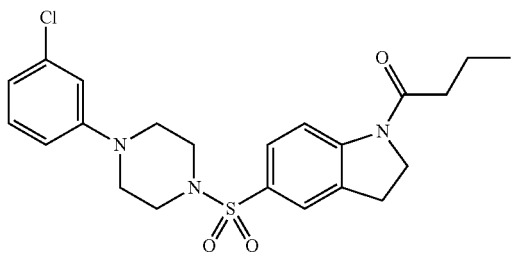 [SMILES: CCCC(=O)N1CCc2cc(S(=O)(=O)N3CCN(c4cccc(Cl)c4)CC3)ccc21]

(JHE-02-033A) 1-(5-(4-(3-Chlorophenyl)piperazin-1-ylsulfonyl)indolin-1-yl)butan-1-one JHE-02-033A was prepared from JHE-01-120 and butyryl chloride (converted from the corresponding acid) using the same procedure as described for the preparation of JF028. JHE-02-033A: Pale yellow solid, yield 84%. Mp=267-268° C.; $^1$H NMR (CD$_3$CN, 400 MHz) δ 8.32 (d, J=8.0 Hz, 1H), 7.60-7.58 (m, 2H), 7.20 (dd, J=8.0 Hz, 8.0 Hz, 1H), 6.91 (dd, J=2.0 Hz, 2.0 Hz, 1H), 6.85-6.81 (m, 2H), 4.16 (t, J=8.4 Hz, 2H), 3.27-3.22 (m, 6H), 3.07 (t, J=5.2 Hz, 4H), 2.46 (t, J=6.8 Hz, 2H), 1.74-1.65 (m, 2H), 1.00 (t, J=7.6 Hz, 3H); HPLC 99% (t$_R$=7.29, 70% acetonitrile in water (0.1% TFA)); HPLC 98% (t$_R$=16.01, 70% methanol in water (0.1% TFA)); HRMS (ESI-ve) m/z calcd. for C$_{22}$H$_{27}$ClN$_3$O$_3$S, 448.1456 (M+H)$^+$. found 448.1456 (M+H)$^+$.

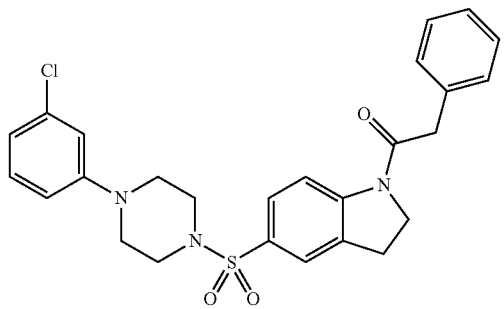

(JF031) 1-(5-(4-(3-Chlorophenyl)piperazin-1-ylsulfonyl)indolin-1-yl)-2-phenylethanone JF031 was prepared from JHE-01-120 and 2-phenylacetyl chloride (converted from the corresponding acid) using the same procedure as described for the preparation of JF028. JF031: Off-white solid, yield 84%. Mp=213-214° C.; $^1$H NMR (DMSO-d$_6$, 400 MHz) 8.20 (d, J=8.4 Hz, 1H), 7.58-7.55 (m, 2H), 7.33-7.21 (m, 5H), 7.17 (dd, J=8.0 Hz, 8.0 Hz, 1H), 6.90 (dd, J=1.6 Hz, 1.6 Hz, 1H), 6.84 (dd, J=8.0 Hz, 1.6 Hz, 1H), 6.78 (dd, J=8.0 Hz, 1.6 Hz, 1H), 4.24 (t, J=8.4 Hz, 2H), 3.87 (s, 2H), 3.25-3.21 (m, 6H), 2.96-2.92 (m, 4H); HPLC 97% (t$_R$=7.77, 70% acetonitrile in water (0.1% TFA)); HPLC 98% [t$_R$=14.33, 70% methanol in water (0.1% TFA)]; HRMS (ESI-ve) m/z calcd. for C$_{26}$H$_{27}$ClN$_3$O$_3$S, 496.1456 (M+H)$^+$. found 496.1457 (M+H)$^+$.

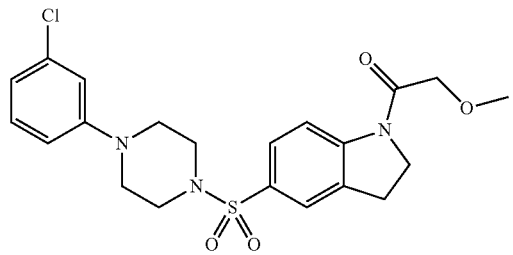 [SMILES: COCC(=O)N1CCc2cc(S(=O)(=O)N3CCN(c4cccc(Cl)c4)CC3)ccc21]

(JHE-01-169) 1-(5-(4-(3-Chlorophenyl)piperazin-1-ylsulfonyl)indolin-1-yl)-2-methoxyethanone JHE-01-169 was prepared from JHE-01-120 and 2-methoxyacetyl chloride (converted from the corresponding acid) using the same procedure as described for the preparation of JF028. JHE-01-169: Off-white solid, yield 89%. Mp=229.5-230° C.; $^1$H NMR (CD$_3$CN, 400 MHz) δ 8.29 (s, 1H), 8.63-8.62 (m, 2H), 7.20 (dd, J=8.0 Hz, 8.0 Hz, 1H), 6.91 (dd, J=2.4 Hz, 2.4 Hz, 1H), 6.85-6.82 (m, 2H), 4.18 (s, 2H), 4.09 (t, J=8.4 Hz, 2H), 3.44 (s, 3H), 3.30-3.25 (m, 6H), 3.07 (t, J=5.2 Hz, 4H), 3.08 (t, J=5.6 Hz, 4H); HPLC 99% (t$_R$=3.81, 70% acetonitrile in water (0.1% TFA)); HPLC 98% [t$_R$=7.13, 70% methanol in water (0.1% TFA)]; HRMS (ESI-ve) m/z calcd. for C$_{27}$H$_{28}$ClN$_4$O$_5$S, 555.1463 (M+H)$^+$. found 555.1454 (M+H)$^+$.

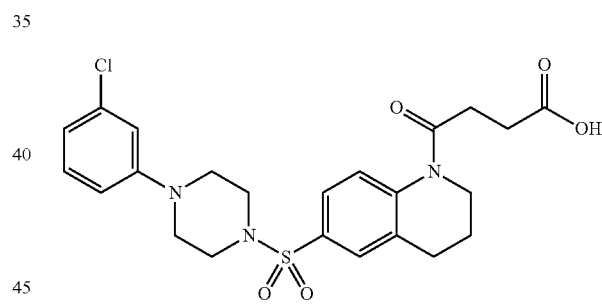

(JHE-02-023) 4-(6-(4-(3-Chlorophenyl)piperazin-1-ylsulfonyl)-3,4-dihydroquinolin-1(2H)-yl)-4-oxobutanoic acid (JHE-02-023) was hydrolyzed in the same fashion as JHE-01-137 from the corresponding ethyl ester (not reported here) which was prepared from the corresponding acid chloride and JHE-01-150 according the procedure described as for the preparation of JF028. JHE-02-023: Off-white solid, yield 53%. Mp=135-136° C.; $^1$H NMR (CD$_3$CN, 400 MHz) δ 7.85 (d, J=8.4 Hz, 1H), 7.59 (s, 1H), 7.56 (d, J=8.4 Hz, 1H), 7.20 (dd, J=8.0 Hz, 8.0 Hz, 1H), 6.92 (s, 1H), 6.86-6.82 (m, 2H), 3.78 (t, J=6.4 Hz, 2H), 3.27 (t, J=5.2 Hz, 4H), 3.09 (t, J=5.2 Hz, 4H), 2.85 (t, J=6.4 Hz, 2H), 2.81-2.78 (m, 2H), 2.62-2.59 (m, 2H), 2.01-1.98 (m, 2H); HPLC 95% (t$_R$=3.16, 70% acetonitrile in water (0.1% TFA)]; HRMS (ESI-ve) m/z calcd. for C$_{23}$H$_{27}$ClN$_3$O$_5$S, 492.1355 (M+H)$^+$. found 492.1356 (M+H)$^+$.

Scheme 4.

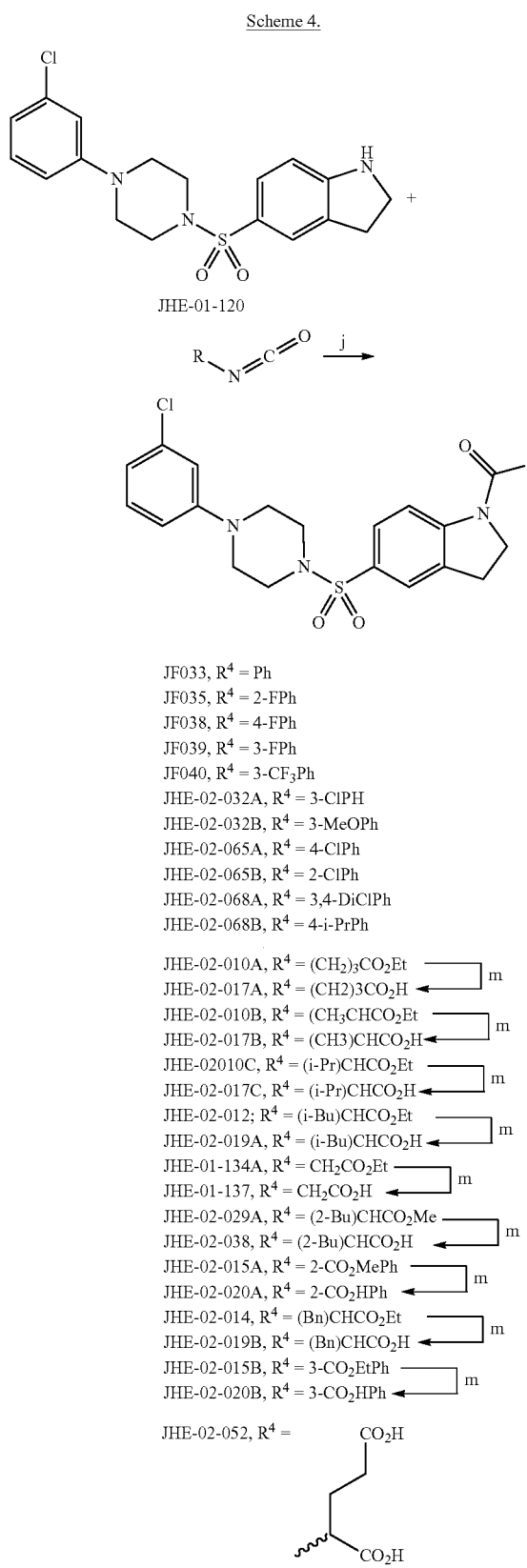

JHE-01-120

JF033, R⁴ = Ph
JF035, R⁴ = 2-FPh
JF038, R⁴ = 4-FPh
JF039, R⁴ = 3-FPh
JF040, R⁴ = 3-CF₃Ph
JHE-02-032A, R⁴ = 3-ClPH
JHE-02-032B, R⁴ = 3-MeOPh
JHE-02-065A, R⁴ = 4-ClPh
JHE-02-065B, R⁴ = 2-ClPh
JHE-02-068A, R⁴ = 3,4-DiClPh
JHE-02-068B, R⁴ = 4-i-PrPh

JHE-02-010A, R⁴ = (CH₂)₃CO₂Et  ⎤ m
JHE-02-017A, R⁴ = (CH2)3CO₂H  ⎦
JHE-02-010B, R⁴ = (CH₃CHCO₂Et  ⎤ m
JHE-02-017B, R⁴ = (CH3)CHCO₂H  ⎦
JHE-02010C, R⁴ = (i-Pr)CHCO₂Et  ⎤ m
JHE-02-017C, R⁴ = (i-Pr)CHCO₂H  ⎦
JHE-02-012; R⁴ = (i-Bu)CHCO₂Et  ⎤ m
JHE-02-019A, R⁴ = (i-Bu)CHCO₂H  ⎦
JHE-01-134A, R⁴ = CH₂CO₂Et  ⎤ m
JHE-01-137, R⁴ = CH₂CO₂H  ⎦
JHE-02-029A, R⁴ = (2-Bu)CHCO₂Me  ⎤ m
JHE-02-038, R⁴ = (2-Bu)CHCO₂H  ⎦
JHE-02-015A, R⁴ = 2-CO₂MePh  ⎤ m
JHE-02-020A, R⁴ = 2-CO₂HPh  ⎦
JHE-02-014, R⁴ = (Bn)CHCO₂Et  ⎤ m
JHE-02-019B, R⁴ = (Bn)CHCO₂H  ⎦
JHE-02-015B, R⁴ = 3-CO₂EtPh  ⎤ m
JHE-02-020B, R⁴ = 3-CO₂HPh  ⎦

JHE-02-052, R⁴ =

Reagents and conditions: (j) isocyanate, THF, microwave, 100° C., 30 min.
(m) 6N NaOH, THF, EtOH, microwave, 80° C., 10 min.

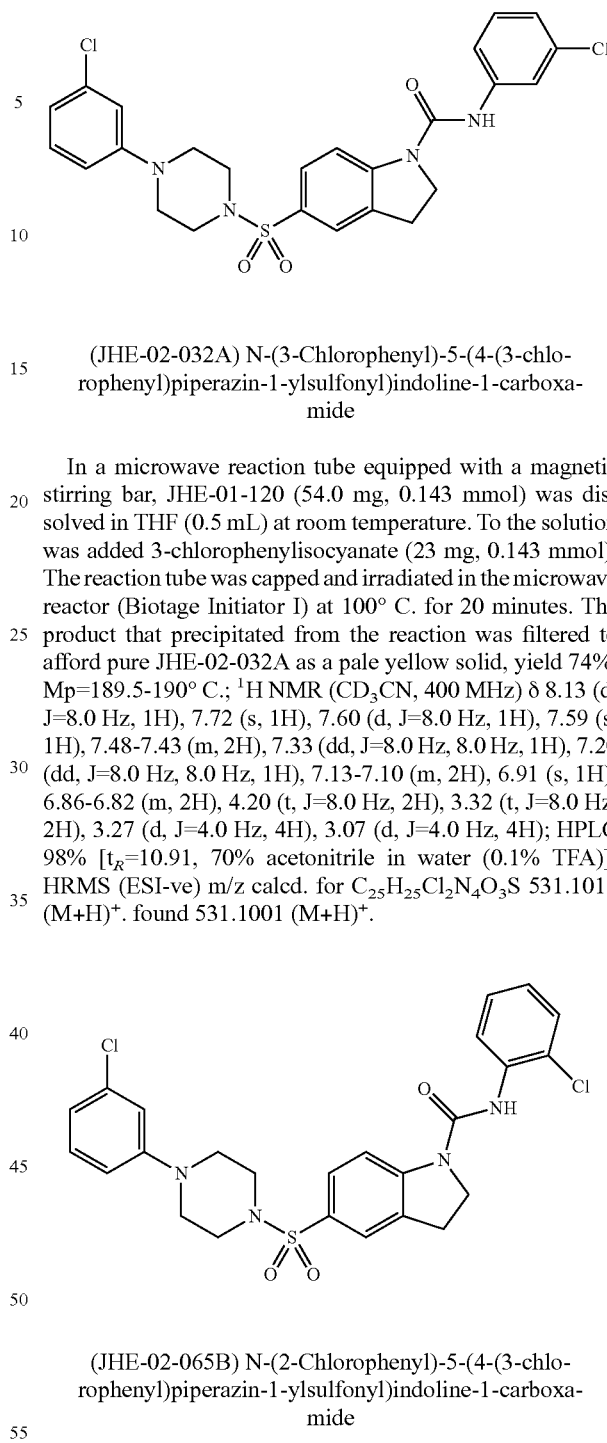

(JHE-02-032A) N-(3-Chlorophenyl)-5-(4-(3-chlorophenyl)piperazin-1-ylsulfonyl)indoline-1-carboxamide In a microwave reaction tube equipped with a magnetic stirring bar, JHE-01-120 (54.0 mg, 0.143 mmol) was dissolved in THF (0.5 mL) at room temperature. To the solution was added 3-chlorophenylisocyanate (23 mg, 0.143 mmol). The reaction tube was capped and irradiated in the microwave reactor (Biotage Initiator I) at 100° C. for 20 minutes. The product that precipitated from the reaction was filtered to afford pure JHE-02-032A as a pale yellow solid, yield 74%. Mp=189.5-190° C.; $^1$H NMR (CD₃CN, 400 MHz) δ 8.13 (d, J=8.0 Hz, 1H), 7.72 (s, 1H), 7.60 (d, J=8.0 Hz, 1H), 7.59 (s, 1H), 7.48-7.43 (m, 2H), 7.33 (dd, J=8.0 Hz, 8.0 Hz, 1H), 7.20 (dd, J=8.0 Hz, 8.0 Hz, 1H), 7.13-7.10 (m, 2H), 6.91 (s, 1H), 6.86-6.82 (m, 2H), 4.20 (t, J=8.0 Hz, 2H), 3.32 (t, J=8.0 Hz, 2H), 3.27 (d, J=4.0 Hz, 4H), 3.07 (d, J=4.0 Hz, 4H); HPLC 98% [$t_R$=10.91, 70% acetonitrile in water (0.1% TFA)]; HRMS (ESI-ve) m/z calcd. for C₂₅H₂₅Cl₂N₄O₃S 531.1019 (M+H)⁺. found 531.1001 (M+H)⁺.

(JHE-02-065B) N-(2-Chlorophenyl)-5-(4-(3-chlorophenyl)piperazin-1-ylsulfonyl)indoline-1-carboxamide JHE-02-065B was prepared using the same procedure as described for the preparation of JHE-02-032A. JHE-02-065B: Off-white solid, yield 83%. Mp=205-206° C.; $^1$H NMR (DMSO-d₆, 400 MHz) δ 8.55 (s, 1H), 7.98 (d, J=8.8 Hz, 1H), 7.56-7.50 (m, 4H), 7.34 (ddd, J=8.0 Hz, 8.0 Hz, 1.2 Hz, 1H), 7.23 (ddd, J=8.0 Hz, 8.0 Hz, 1.2 Hz, 1H), 7.18 (dd, J=8.0 Hz, 8.0 Hz, 1H), 6.91 (s, 1H), 6.85 (d, J=8.0 Hz, 1H), 6.78 (d, J=8.0 Hz, 1H), 4.21 (t, J=8.8 Hz, 2H), 3.31-3.23 (m, 6H), 2.96-2.93 (m, 4H); HPLC 99% [$t_R$=10.32, 70% acetonitrile in water (0.1% TFA)]; HPLC 98% [$t_R$=27.85, 70% acetonitrile in water (0.1% TFA)].

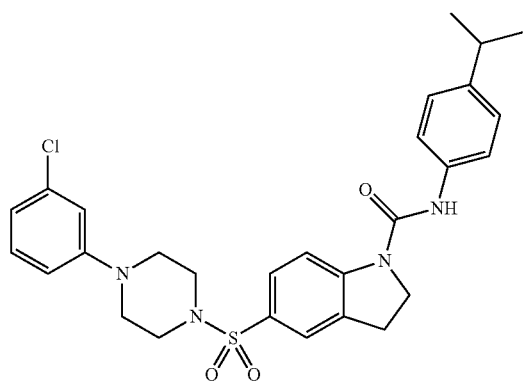 [SMILES: CC(C)c1ccc(NC(=O)N2CCc3cc(S(=O)(=O)N4CCN(c5cccc(Cl)c5)CC4)ccc32)cc1]

(JHE-02-068B) 5-(4-(3-Chlorophenyl)piperazin-1-ylsulfonyl)-N-(4-isopropylphenyl)indoline-1-carboxamide JHE-02-068B was prepared using the same procedure as described for the preparation of JHE-02-032A. JHE-02-068B: Off-white solid, yield 83%. Mp=182-182.5° C.; $^1$H NMR (DMSO-d$_6$, 400 MHz) δ 8.63 (s, 1H), 8.02 (d, J=8.8 Hz, 1H), 7.54-7.51 (m, 2H), 7.43 (d, J=8.4 Hz, 1H), 7.20-7.14 (m, 3H), 6.91 (s, 1H), 6.85 (d, J=8.0 Hz, 1H), 6.78 (d, J=8.0 Hz, 1H), 4.19 (t, J=8.8 Hz, 2H), 3.27-3.22 (m, 6H), 2.96-2.93 (m, 4H), 2.86-2.79 (m, 1H), 1.17 (d, J=7.2 Hz, 6H); HPLC 98% [t$_R$=15.00, 70% acetonitrile in water (0.1% TFA)].

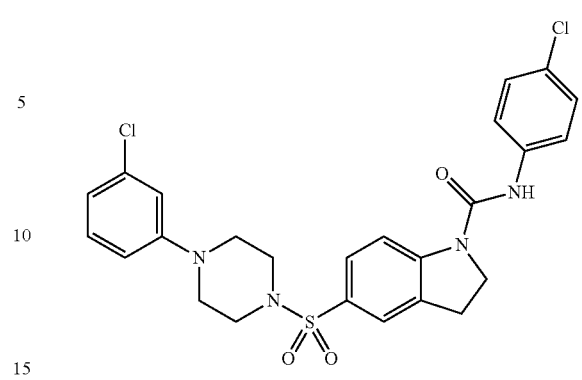

(JHE-02-065A) N-(4-Chlorophenyl)-5-(4-(3-chlorophenyl)piperazin-1-ylsulfonyl)indoline-1-carboxamide JHE-02-065A was prepared using the same procedure as described for the preparation of JHE-02-032A. JHE-02-065A: off-white solid, yield 81%; Mp=188-188.5° C.; $^1$H NMR (DMSO-d$_6$, 400 MHz) δ 8.82 (s, 1H), 8.03 (d, J=9.2 Hz, 1H), 7.61-7.53 (m, 4H), 7.35-7.33 (m, 2H), 7.18 (dd, J=8.0 Hz, 8.0 Hz, 1H), 6.91 (dd, J=2.0 Hz, 2.0 Hz, 1H), 6.85 (dd, J=8.0 Hz, 2.0 Hz, 1H), 6.78 (dd, J=8.0 Hz, 2.0 Hz, 1H), 4.20 (t, J=8.8 Hz, 2H), 3.27-3.23 (m, 6H), 2.96-2.93 (m, 4H); HPLC 98% [t$_R$=10.45, 70% acetonitrile in water (0.1% TFA)].

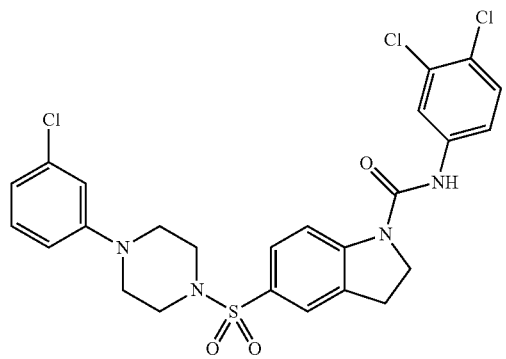 [SMILES: O=C(Nc1ccc(Cl)c(Cl)c1)N1CCc2cc(S(=O)(=O)N3CCN(c4cccc(Cl)c4)CC3)ccc21]

(JHE-02-068A) 5-(4-(3-Chlorophenyl)piperazin-1-ylsulfonyl)-N-(3,4-dichlorophenyl)indoline-1-carboxamide JHE-02-068A was prepared using the same procedure as described in the preparation of JHE-02-032A. JHE-02-068A: Off-white solid, yield 92%. Mp=195-196° C.; $^1$H NMR (DMSO-d$_6$, 400 MHz) δ 8.96 (s, 1H), 8.03 (d, J=9.2 Hz, 1H), 7.92 (d, J=2.0 Hz, 1H), 7.59-7.53 (m, 4H), 7.17 (dd, J=8.0 Hz, 8.0 Hz, 1H), 6.91 (dd, J=2.0 Hz, 2.0 Hz, 1H), 6.85 (dd, J=8.0 Hz, 2.0 Hz, 1H), 6.78 (dd, J=8.0 Hz, 2.0 Hz, 1H), 4.19 (t, J=8.8 Hz, 2H), 3.29-3.23 (m, 6H), 2.96-2.93 (m, 4H); HPLC 98% [t$_R$=16.65, 70% acetonitrile in water (0.1% TFA)].

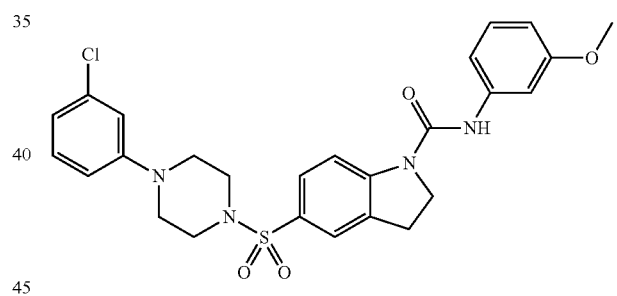

(JHE-02-032B) 5-(4-(3-Chlorophenyl)piperazin-1-ylsulfonyl)-N-(3-methoxyphenyl)indoline-1-carboxamide JHE-02-032B was prepared using the same procedure as described for the preparation of JHE-02-032A. JHE-02-032B: pale yellow solid, yield 79%. Mp=199-199.5° C.; $^1$H NMR (CD$_3$CN, 400 MHz) δ 8.13 (d, J=8.0 Hz, 1H), 7.60-7.58 (m, 2H), 7.31 (s, br, 1H, NH), 7.27-7.13 (m, 4H), 6.91 (dd, J=2.0 Hz, 2.0 Hz, 2H), 6.86-6.82 (m, 2H), 6.68 (dd, =8.0 Hz, 2.0 Hz, 1H), 4.20 (t, J=8.8 Hz, 2H), 3.80 (s, 3H), 3.34-3.25 (m, 6H), 3.07 (t, J=5.2 Hz, 4H); HPLC 98% [t$_R$=6.88, 70% acetonitrile in water (0.1% TFA)]; HPLC 97% [t$_R$=21.43, 70% methanol in water (0.1% TFA)]; HRMS (ESI-ve) m/z calcd. for C$_{26}$H$_{28}$ClN$_4$O$_4$S, 527.1514 (M+H)$^+$. found 527.1515 (M+H)$^+$.

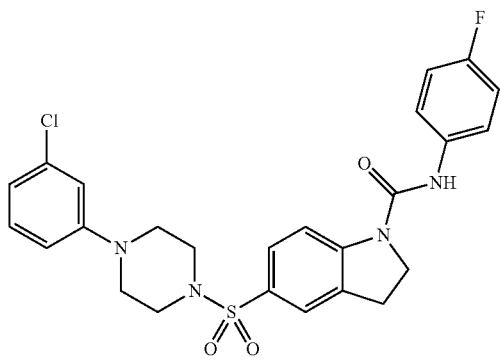

(JF038) 5-(4-(3-Chlorophenyl)piperazin-1-ylsulfonyl)-N-(4-fluorophenyl)indoline-1-carboxamide JF038 was prepared using the same procedure as described for the preparation of JHE-02-032A. JF038: off-white solid, yield 62%. Mp=192.5-193.5° C.; $^1$H NMR (DMSO-d$_6$, 400 MHz) δ 8.76 (s, 1H), 8.02 (d, J=8.8 Hz, 1H), 7.56-7.52 (m, 4H), 7.20-7.11 (m, 3H), 6.91 (dd, J=2.0 Hz, 2.0 Hz, 1H), 6.84 (dd, J=8.0 Hz, 2.0 Hz, 1H), 6.78 (dd, J=8.0 Hz, 2.0 Hz, 1H), 4.19 (t, J=8.4 Hz, 2H), 3.27-3.23 (m, 6H), 2.97-2.93 (m, 4H); HPLC 97% [t$_R$=7.13, 70% acetonitrile in water (0.1% TFA)]; HPLC 97% [t$_R$=14.63, 70% methanol in water (0.1% TFA)]; HRMS (ESI-ve) m/z calcd. for C$_{25}$H$_{25}$ClFN$_4$O$_3$S, 515.1314 (M+H)$^+$. found 515.1310 (M+H)$^+$.

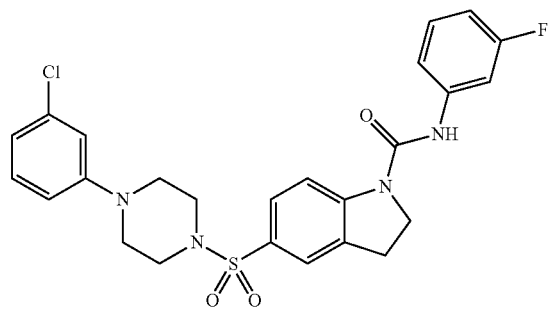 [SMILES: O=C(Nc1cccc(F)c1)N1CCc2cc(S(=O)(=O)N3CCN(c4cccc(Cl)c4)CC3)ccc21]

(J039) 5-(4-(3-Chlorophenyl)piperazin-1-ylsulfonyl)-N-(3-fluorophenyl)indoline-1-carboxamide JF039 was prepared using the same procedure as described for the preparation of JHE-02-032A. JF039: white solid, 84%. Mp=208.5-209.5° C.; $^1$H NMR (DMSO-d$_6$, 400 MHz) δ 8.88 (s, 1H), 8.03 (d, J=8.8 Hz, 1H), 7.55-7.49 (m, 3H), 7.38-7.28 (m, 2H), 7.18 (dd, J=8.0 Hz, 8.0 Hz, 1H), 6.91, (s, 1H), 6.84 (d, J=8.0 Hz, 1H), 6.78 (d, J=8.0 Hz, 1H), 4.21 (t, J=8.4 Hz, 2H), 3.29-3.23 (m, 6H), 2.96-2.93 (m, 4H); $^{13}$C NMR (DMSO-d$_6$, 100.6 MHz) δ 163.9, 161.6, 153.0, 148.7, 142.0, 134.5, 133.5, 131.2, 130.7, 128.7, 127.5, 124.8, 119.5, 116.7, 115.9, 115.0, 109.7, 107.8, 48.7, 48.0, 46.3, 27.6; HPLC 96% [t$_R$=8.19, 70% acetonitrile in water (0.1% TFA)]; HRMS (ESI-ve) nil: calcd. for C$_{25}$H$_{25}$ClFN$_4$O$_3$S, 515.1314 (M+H)$^+$. found 515.1313 (M+H)$^+$.

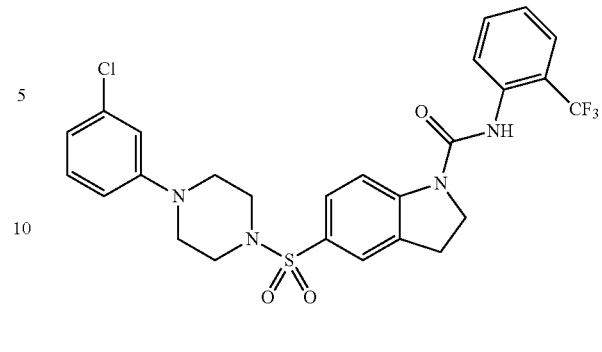

(JF040) 5-(4-(3-Chlorophenyl)piperazin-1-ylsulfonyl)-N-(2-(trifluoromethyl)phenyl)indoline-1-carboxamide JF040 was prepared using the same procedure as described for the preparation of JHE-02-032A. JF040: White solid, yield 68%. Mp=204-205° C.; $^1$H NMR (DMSO-d$_6$, 400 MHz) δ 8.63 (s, br, 1H), 7.97 (d, J=8.4 Hz, 1H), 7.73 (d, J=8.0 Hz, 1H), 7.97 (dd, J=7.6 Hz, 7.6 Hz, 1H), 7.56-7.45 (m, 4H), 7.18 (dd, J=8.0 Hz, 8.0 Hz, 1H), 6.91, (s, 1H), 6.85 (d, J=8.0 Hz, 1H), 6.79 (d, J=8.0 Hz, 1H), 4.17 (t, J=8.8 Hz, 2H), 3.30-3.24 (m, 6H), 2.95-2.93 (m, 4H); $^{13}$C NMR (DMSO-d$_6$, 100.6 MHz) δ 154.1, 152.3, 148.9, 134.5, 133.6, 133.2, 131.5, 131.2, 128.8, 127.1, 124.8, 119.5, 115.9, 115.0, 114.6, 48.6, 48.0, 46.4, 27.6; $^{19}$F NMR (DMSO-d$_6$, 100.6 MHz) δ −59.4; HPLC 97% [t$_R$=8.63, 70% acetonitrile in water (0.1% TFA)]; HRMS (ESI-ve) m/z calcd. for C$_{26}$H$_{25}$ClF$_3$N$_4$O$_3$S 565.1283 (M+H)$^+$. found 565.1283 (M+H)$^+$.

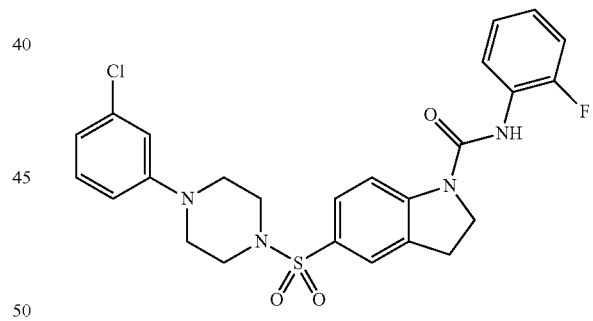

(JF035) 5-(4-(3-Chlorophenyl)piperazin-1-ylsulfonyl)-N-(2-fluorophenyl)indoline-1-carboxamide JF035 was prepared using the same procedure as described for the preparation of JHE-02-032A. JF035: White solid, yield 62%. Mp=174-175° C.; $^1$H NMR (DMSO-d$_6$, 400 MHz) δ 8.62 (s, 1H), 7.98 (d, J=8.4 Hz, 1H), 7.54 (s, 1H), 7.53 (d, J=8.4 Hz, 1H), 7.27-7.15 (m, 4H), 6.91 (s, 1H), 6.85 (d, J=8.0 Hz, 1H), 6.78 (d, J=8.0 Hz, 1H), 4.20 (t, J=8.8 Hz, 2H), 3.29-3.24 (m, 6H), 2.96-2.93 (m, 4H); HPLC 100% [t$_R$=6.38, 70% acetonitrile in water (0.1% TFA)]; HPLC 99% [t$_R$=12.52, 70% methanol in water (0.1% TFA)]; FIRMS (ESI-ve) m/z calcd. for C$_{25}$H$_{25}$ClFN$_4$O$_3$S, 515.1314 (M+H)$^+$. found 515.1320 (M+H)$^+$.

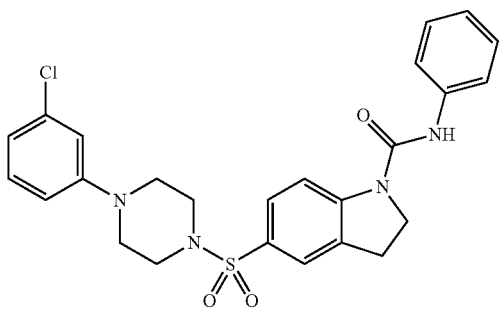 [SMILES: O=C(Nc1ccccc1)N1CCc2cc(S(=O)(=O)N3CCN(c4cccc(Cl)c4)CC3)ccc21]

(JF033) 5-(4-(3-Chlorophenyl)piperazin-1-ylsulfonyl)-N-phenylindoline-1-carboxamide JF033 was prepared using the same procedure as described for the preparation of JHE-02-032A. JF033: White solid, yield 85%. Mp=177-178° C.; $^1$H NMR (DMSO-d$_6$, 400 MHz) δ 8.70 (s, 1H), 8.03 (d, J=8.8 Hz, 1H), 7.55-7.53 (m, 4H), 7.31-7.27 (m, 2H), 7.18 (dd, J=8.0 Hz, 8.0 Hz, 1H), 7.03 (dd, J=7.2 Hz, 7.2 Hz, 1H), 6.91 (dd, J=2.0 Hz, 1H), 6.85 (dd, J=8.4 Hz, 2.0 Hz, 1H), 6.78 (dd, J=8.4 Hz, 2.0 Hz, 1H), 4.21 (t, J=8.8 Hz, 2H), 3.37-3.23 (m, 6H), 2.97-2.93 (m, 4H); $^{13}$C NMR (DMSO-d$_6$, 100.6 MHz) δ 153.2, 152.3, 149.0, 139.8, 134.5, 133.3, 131.2, 129.1, 128.7, 127.2, 124.7, 123.7, 121.4, 119.5, 115.9, 115.0, 114.9, 48.7, 48.0, 46.4, 27.6; HPLC 99% [t$_R$=6.52, 70% acetonitrile in water (0.1% TFA)]; HPLC 99% [t$_R$=13.22, 70% methanol in water (0.1% TFA)]; HRMS (ESI-ve) m/z calcd. for C$_{25}$H$_{26}$ClN$_4$O$_3$S, 497.1409 (M+H)$^+$. found 497.1416 (M+H)$^+$.

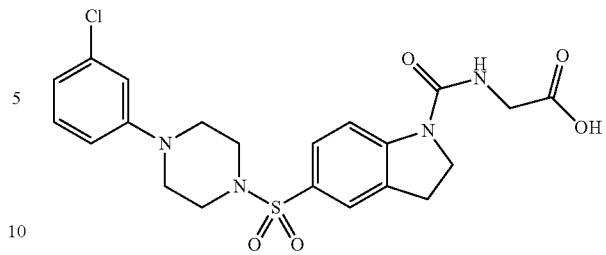

(JHE-01-137) 2-(5-(4-(3-Chlorophenyl)piperazin-1-ylsulfonyl)indoline-1-carboxamido)acetic acid JHE-01-134A (50 mg, 0.01 mmol) was mixed with NaOH (6.0M, 0.1 mL), ethanol (0.2 mL) and THF (0.4 mL) at room temperature in a microwave reaction tube equipped with a magnetic stirring bar. The reaction tube was capped and irradiated in the microwave reactor (Biotage Initiator I) at 80° C. for 10 minutes. After concentration, the reaction mixture was acidified to pH-4 and diluted with water. The product was filtered and washed with water. JHE-01-137: gray solid, yield 97%. Mp=214-214.5° C.; $^1$H NMR (DMSO-d$_6$, 400 MHz) δ 7.97 (d. J=8.8 Hz, 1H), 7.50-7.48 (m, 2H), 7.27 (t, J=5.6 Hz, 1H, NH), 7.17 (dd, J=8.0 Hz, 8.0 Hz, 1H), 6.90 (1H, s), 6.84 (d, J=8.8 Hz, 1H), 6.77 (d, J=7.2 Hz, 1H), 3.98 (t, J=8.8 Hz, 2H), 3.74 (d, J=5.6 Hz, 2H), 3.26-3.19 (m, 6H), 2.94-2.91 (m, 4H); HPLC 94% [t$_R$=2.60, 70% acetonitrile in water (0.1% TFA)]; HRMS (ESI-ve) m/z calcd. for C$_{21}$H$_{24}$ClN$_4$O$_5$S, 479.1150 (M+H)$^+$. found 479.1141 (M+H)$^+$.

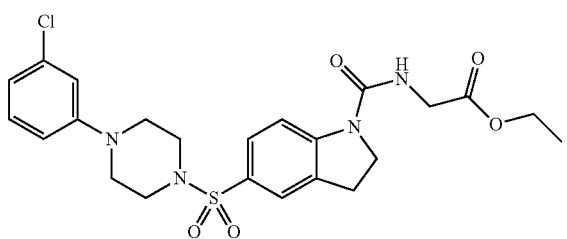 [SMILES: CCOC(=O)CNC(=O)N1CCc2cc(S(=O)(=O)N3CCN(c4cccc(Cl)c4)CC3)ccc21]

(JHE-01-134A) ethyl 2-(5-(4-(3-Chlorophenyl)piperazin-1-ylsulfonyl)indoline-1-carboxamido)acetate JHE-01-134A was prepared using the same procedure as described for the preparation of JHE-02-032A. JHE-01-134A: light brown solid, yield 100%. Mp=149.5-150.5° C.; $^1$H NMR (CD$_3$CN, 400 MHz) δ 8.05 (d, J=9.2 Hz, 1H), 7.56-7.53 (m, 2H), 7.20 (dd, J=8.0 Hz, 8.0 Hz, 1H), 6.91 (dd, J=2.0 Hz, 2.0 Hz, 1H), 6.85-6.82 (m, 2H), 5.92 (t, J=6.0 Hz, 1H, NH), 4.18 (q, J=7.2 Hz, 2H), 4.03 (t, J=8.8 Hz, 2H), 3.93 (d, J=6.0 Hz, 2H), 3.30-3.24 (m, 6H), 3.06 (t, J=5.2 Hz, 4H), 1.26 (t, J=7.2 Hz, 3H); HPLC 96% [t$_R$=4.13, 70% acetonitrile in water (0.1% TFA)]; HPLC 98% [t$_R$=9.37, 70% methanol in water (0.1% TFA)]; HRMS (ESI-ve) m/z calcd. for C$_{22}$H$_{25}$ClN$_3$O$_6$S, 494.1147 (M+H)$^+$. found 494.1147 (M+H)$^+$.

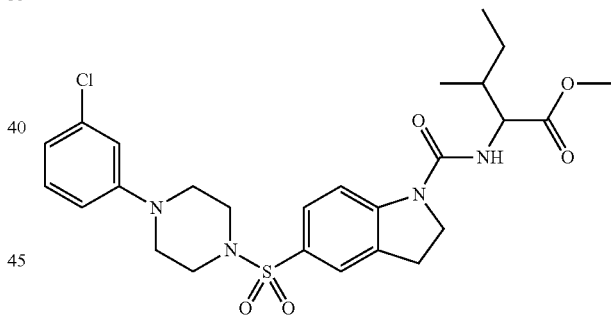

(JHE-02-029A) Methyl 2-(5-(4-(3-chlorophenyl)piperazin-1-ylsulfonyl)indoline-1-carboxamido)-3-methylpentanoate JHE-02-029A was prepared using the same procedure as described for the preparation of JHE-02-032A. JHE-02-029A: white solid, yield 87%. Mp=145-146° C.; $^1$H NMR (CD$_3$CN, 400 MHz) δ 8.03 (d, J=9.2 Hz, 1H), 7.55-7.53 (m, 2H), 7.20 (dd, J=8.0 Hz, 8.0 Hz, 1H), 6.91 (dd, J=2.0, Hz, 2.0 Hz, 1H), 6.85-6.82 (m, 2H), 5.55 (t, J=8.0 Hz, 1H, NH), 4.34 (dd, J=8.0 Hz, 6.4 Hz, 1H), 4.07 (t, J=8.8 Hz, 2H), 3.71 (s, 3H), 3.30-3.24 (m, 6H), 3.06 (t, J=5.2 Hz, 4H), 1.81-1.78 (m, 1H), 1.59-1.51 (m, 1H), 1.33-1.21 (m, 1H), 0.96-0.89 (m, 6H); HPLC 98% (t$_R$=8.44, 70% acetonitrile in water (0.1% TFA)); HPLC 99% [t$_R$=26.23, 70% methanol in water (0.1% TFA)]; HRMS (ESI-ve) m/z calcd. for C$_{26}$H$_{34}$ClN$_4$O$_5$S, 549.1933 (M+H)$^+$. found 549.1937 (M+H)$^+$.

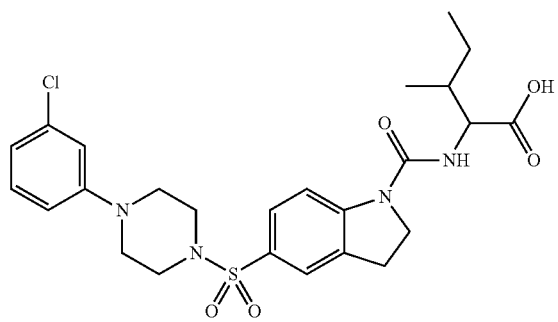 [SMILES: CCC(C)C(NC(=O)N1CCc2cc(S(=O)(=O)N3CCN(c4cccc(Cl)c4)CC3)ccc21)C(=O)O]

(JHE-02-038) 2-(5-(4-(3-Chlorophenyl)piperazin-1-ylsulfonyl)indoline-1-carboxamido)-3-methylpentanoic acid JHE-02-038 was prepared from JHE-02-029A using the same procedure as described for the preparation of JHE-02-137. JHE-02-038: light pink solid, yield 93%. Mp=163-164° C.; $^1$H NMR (CD$_3$CN, 400 MHz) δ 8.04 (d, J=8.4 Hz, 1H), 7.56-7.54 (m, 2H), 7.20 (dd, J=8.0 Hz, 8.0 Hz, 1H), 6.91 (dd, J=2.0 Hz, 2.0 Hz, 1H), 6.85-6.82 (m, 2H), 5.55 (d, J=7.6 Hz, 1H, NH), 4.28 (dd, J=7.6 Hz, 6.4 Hz, 2H), 4.07 (t, J=8.0 Hz, 2H), 3.29-3.24 (m, 6H), 3.06 (t, J=5.2 Hz, 4H), 1.63-1.53 (m, 1H), 1.34-1.21 (m, 1H), 0.99 (d, J=6.4 Hz, 3H), 0.95 (t, J=8.0 Hz, 3H); HPLC 99% [$t_R$=4.53, 70% acetonitrile in water (0.1% TFA)]; HPLC 99.5% [$t_R$=18.53, 70% methanol in water (0.1% TFA)]; HRMS (ESI-ve) m/z calcd. for C$_{25}$H$_{32}$ClN$_4$O$_5$S, 535.1776 (M+H)$^+$. found 535.1780 (M+H)$^+$.

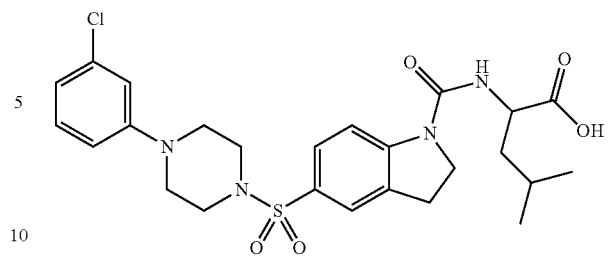

(JHE-02-019A) 2-(5-(4-(3-Chlorophenyl)piperazin-1-ylsulfonyl)indoline-1-carboxamido)-4-methylpentanoic acid JHE-02-019A was prepared from JHE-02-012 using the same procedure as described for the preparation of JHE-02-137. JHE-02-019A: pink solid, yield 87%. Mp=138.5-140° C.; $^1$H NMR (CD$_3$CN, 400 MHz) δ 8.03 (d, J=9.2 Hz, 1H), 7.55-7.53 (m, 2H), 7.20 (dd, J=8.0 Hz, 8.0 Hz, 1H), 6.91 (t, J=2.0 Hz, 1H), 6.85-6.81 (m, 2H), 5.71 (d, J=8.0 Hz, 1H, NH), 4.39-4.34 (m, 1H), 4.10-3.99 (m, 2H), 3.29-3.24 (m, 6H), 3.05 (t, J=5.2 Hz, 2H), 1.80-1.72 (m, 2H), 1.68-1.63 (m, 1H), 0.98 (d, J=6.4 Hz, 3H), 0.95 (d, J=6.4 Hz, 3H); HPLC 96% [$t_R$=4.56, 70% acetonitrile in water (0.1% TFA)]; HPLC 96% [$t_R$=19.05, 70% methanol in water (0.1% TFA)]; HRMS (ESI-ve) m/z calcd. for C$_{25}$H$_{32}$ClN$_4$O$_5$S, 535.1776 (M+H)$^+$. found 535.1773 (M+H)$^+$.

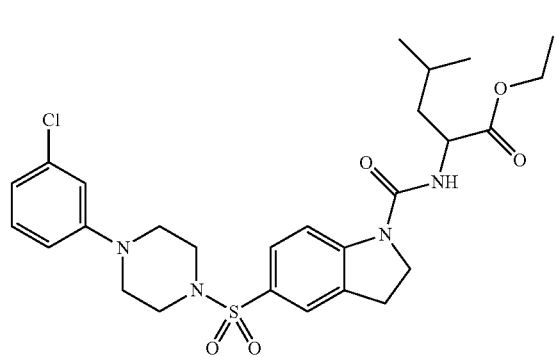 [SMILES: CCOC(=O)C(CC(C)C)NC(=O)N1CCc2cc(S(=O)(=O)N3CCN(c4cccc(Cl)c4)CC3)ccc21]

(JHE-02-012) Ethyl 2-(5-(4-(3-chlorophenyl)piperazin-1-ylsulfonyl)indoline-1-carboxamido)-4-methylpentanoate JHE-01-12 was prepared using the same procedure as described for the preparation of JHE-02-032A. JHE-02-012: light orange foam-like solid, yield 100%. Mp=76-77° C.; $^1$H NMR (CD$_3$CN, 400 MHz) δ 8.03 (d, J=6.8 Hz, 1H), 7.55 (s, 1H), 7.54 (d, J=6.8 Hz, 1H), 7.20 (dd, J=8.0 Hz, 8.0 Hz, 1H), 6.91 (d, J=2.0 Hz, 1H), 6.85-6.81 (m, 2H), 5.67 (d, J=8.0 Hz, 1H, NH), 4.43-4.37 (m, 1H), 4.19-4.12 (m, 2H), 4.09-3.99 (m, 2H), 3.29-3.24 (m, 6H), 3.05 (t, J=5.2 Hz, 4H), 1.82-1.58 (m, 3H), 1.25 (t, J=8.4 Hz, 3H), 0.98 (d, J=6.4 Hz, 3H), 0.95 (t, J=6.4 Hz, 3H); HPLC 95% [$t_R$=10.47, 70% acetonitrile in water (0.1% TFA)]; HPLC 96% [$t_R$=9.77, 70% methanol in water (0.1% TFA)]; HRMS (ESI-ve) m/z calcd. for C$_{27}$H$_{36}$ClN$_4$O$_5$S, 563.2090 (M+H)$^+$. found 563.2090 (M+H)$^+$.

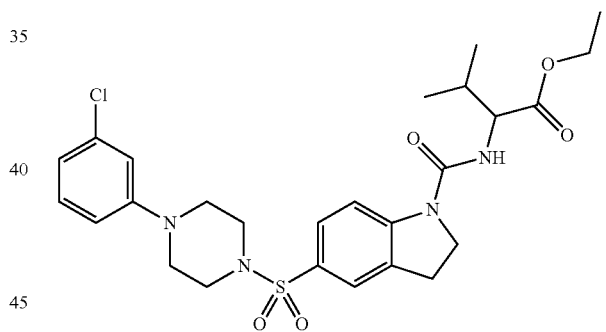

(JHE-02-010C) Ethyl 2-(5-(4-(3-chlorophenyl)piperazin-1-ylsulfonyl)indoline-1-carboxamido)-3-methylbutanoate JHE-02-010C was prepared using the same procedure as described for the preparation of JHE-02-032A. JHE-02-010C: off-white solid, yield 95%. Mp=143-143.5° C.; $^1$H NMR (CD$_3$CN, 400 MHz) δ 8.03 (d, J=9.2 Hz, 1H), 7.55-7.53 (m, 2H), 7.20 (dd, J=8.0 Hz, 8.0 Hz, 1H), 6.91 (t, J=2.0 Hz, 1H), 6.85-6.81 (m, 2H), 5.52 (d, J=8.0 Hz, 1H, NH), 4.27 (dd, J=8.0 Hz, 6.4 Hz, 1H), 4.23-4.14 (m, 2H), 4.09 (t, J=8.8 Hz, 2H), 3.29-3.24 (m, 6H), 3.05 (t, J=5.2 Hz, 4H), 1.27 (t, J=7.2 Hz, 3H), 1.00 (d, J=7.2 Hz, 3H), 0.99 (d, J=7.2 Hz, 3H), 0.96-0.87 (m, 1H); HPLC 95% [$t_R$=8.57, 70% acetonitrile in water (0.1% TFA)]; HPLC 96% [$t_R$=25.36, 70% methanol in water (0.1% TFA)]; HRMS (ESI-ve) m/z calcd. for C$_{26}$H$_{34}$ClN$_4$O$_5$S, 549.1933 (M+H)$^+$. found 549.1936 (M+H)$^+$.

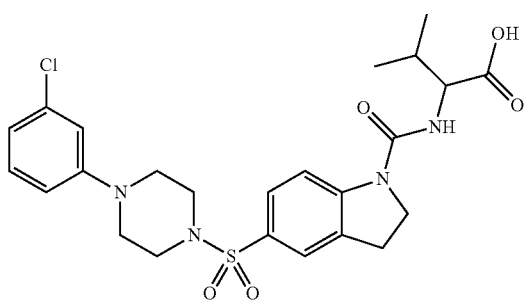 [SMILES: CC(C)C(NC(=O)N1CCc2cc(S(=O)(=O)N3CCN(c4cccc(Cl)c4)CC3)ccc21)C(=O)O]

(JHE-02-017C) 2-(5-(4-(3-Chlorophenyl)piperazin-1-ylsulfonyl)indoline-1-carboxamido)-3-methylbutanoic acid JHE-02-017C was prepared from JHE-02-010C using the same procedure as described for the preparation of JHE-02-137. JHE-02-017C: gray solid, yield 49%. Mp=185-186° C.; NMR (DMSO-$d_6$, 400 MHz) δ 8.04 (d, J=8.4 Hz, 1H), 7.56-7.54 (m, 2H), 7.20 (dd, J=8.0 Hz, 8.0 Hz, 1H), 6.91 (d, J=2.0 Hz, 1H), 6.85-6.82 (m, 2H), 5.54 (d, J=8.0 Hz, 1H, NH), 4.24 (dd, J=8.0 Hz, 6.4 Hz, 1H), 4.08 (d, J=8.8 Hz, 1H), 3.29-3.24 (m, 6H), 3.05 (t, J=5.2 Hz, 4H), 1.01 (d, J=6.4 Hz, 3H), 1.00 (d, J=6.4 Hz, 3H); ); HPLC 96% [$t_R$=3.81, 70% acetonitrile in water (0.1% TFA)]: HPLC 96% [$t_R$=12.69, 70% methanol in water (0.1% TFA)]; HRMS (ESI-ve) m/z calcd. for $C_{24}H_{30}ClN_4O_5S$, 521.1620 (M+H)$^+$. found 526.1618 (M+H)$^+$.

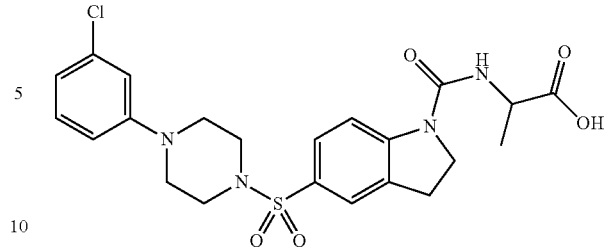

(JHE-02-017B) 2-(5-(4-(3-Chlorophenyl)piperazin-1-ylsulfonyl)indoline-1-carboxamido)propanoic acid JHE-02-017B was prepared from JHE-02-010B using the same procedure as described for the preparation of JHE-02-137. JHE-02-017B: off-white solid, yield 95%. Mp=175-176° C.; $^1$H NMR (DMSO-$d_6$, 400 MHz) δ 7.95 (d, J=8.4 Hz, 1H), 7.49 (s, 1H), 7.48 (d, J=8.4 Hz, 1H), 7.17 (dd, J=8.4 Hz, 8.4 Hz, 1H), 7.13 (d, J=6.8 Hz, 1H, NH), 6.90 (s, 1H), 6.84 (d, J=8.4 Hz, 1H), 6.78 (d, J=8.4 Hz, 1H), 4.35 (t, J=8.4 Hz, 2H), 3.27-3.23 (m, 6H), 2.95-2.93 (m, 4H), 1.99-1.93 (m, 1H), 0.88 (d, J=6.0 Hz, 4H); HPLC 95% [$t_R$=2.89, 70% acetonitrile in water (0.1% TFA)]; HPLC 94% [$t_R$=7.16, 70% methanol in water (0.1% TFA)]; HRMS (ESI-ve) m/z calcd. for $C_{22}H_{26}ClN_4O_5S$, 493.1307 (M+H)$^+$. found 493.1306 (M+H)$^+$.

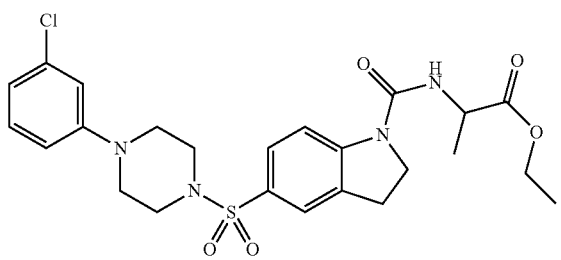 [SMILES: CCOC(=O)C(C)NC(=O)N1CCc2cc(S(=O)(=O)N3CCN(c4cccc(Cl)c4)CC3)ccc21]

(JHE-02-010B) Ethyl 2-(5-(4-(3-chlorophenyl)piperazin-1-ylsulfonyl)indoline-1-carboxamido)propanoate JHE-02-010B was prepared using the same procedure as described for the preparation of JHE-02-032A. JHE-02-010B: off-white solid, yield 94%. Mp=167-168.5° C.; $^1$H NMR (CD$_3$CN, 400 MHz) δ 8.04 (d, J=8.4 Hz, 1H), 7.55-7.53 (m, 2H), 7.20 (dd, J=8.4 Hz, 8.4 Hz, 1H), 6.91 (dd, J=2.0 Hz, 2.0 Hz, 1H), 6.85-6.82 (m, 2H), 5.77 (d, J=7.2 Hz, 1H, NH), 4.38 (dq, J=7.2 Hz, 7.2 Hz, 1H), 4.20-4.12 (m, 2H), 4.09-3.99 (m, 2H), 3.29-3.24 (m, 6H), 3.07-3.04 (m, 4H), 1.43 (d, J=7.2 Hz, 1H), 1.29-1.22 (m, 3H); HPLC 93% [$t_R$=5.13, 70% acetonitrile in water (0.1% TFA)]; HRMS (ESI-ve) m/z calcd. for $C_{24}H_{30}ClN_4O_5S$, 521.1620 (M+H)$^+$. found 521.1630 (M+H)$^+$.

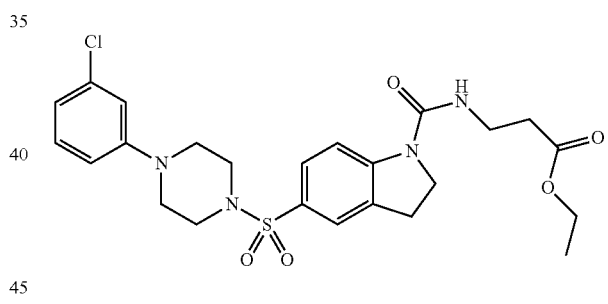

(JHE-02-010A) Ethyl 3-(5-(4-(3-chlorophenyl)piperazin-1-ylsulfonyl)indoline-1-carboxamido)propanoate JHE-02-010A was prepared using the same procedure as described for the preparation of JHE-02-032A. JHE-02-010A: light orange solid, yield 92%. Mp=161.5-162.5° C.; $^1$H NMR (CD$_3$CN, 400 MHz) δ 8.07 (d, J=9.2 Hz, 1H), 7.56-7.53 (m, 2H), 7.20 (dd, J=8.0 Hz, 8.0 Hz, 1H), 6.91 (dd, J=2.0, Hz, 2.0 Hz, 1H), 6.85-6.81 (m, 2H), 5.71 (t, J=6.8 Hz, 1H, NH), 4.12 (q, J=7.2 Hz, 2H), 3.94 (q, J=8.4 Hz, 2H), 3.48 (dt, J=6.8 Hz, 6.8 Hz, 2H), 3.27-3.12 (m, 6H), 3.05 (t, J=5.2 Hz, 4H), 2.55 (t, J=6.8 Hz, 2H), 1.23 (t, J=7.2 Hz, 3H); HPLC 98% [$t_R$=4.47, 70% acetonitrile in water (0.1% TFA)]; HPLC 98% [$t_R$=11.67, 70% methanol in water (0.1% TFA)]; HRMS (ESI-ve) m/z calcd. for $C_{24}H_{30}ClN_4O_5S$, 521.1620 (M+H)$^+$. found 521.1631 (M+H)$^+$.

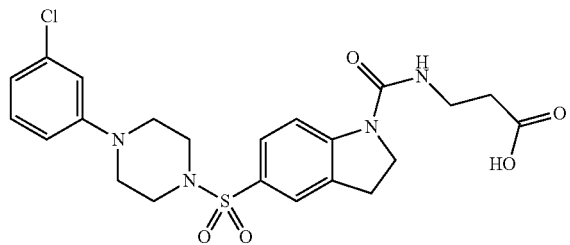 [SMILES: O=C(O)CCNC(=O)N1CCc2cc(S(=O)(=O)N3CCN(c4cccc(Cl)c4)CC3)ccc21]

(JHE-02-017A) 3-(5-(4-(3-Chlorophenyl)piperazin-1-ylsulfonyl)indoline-1-carboxamido)propanoic acid JHE-02-017A was prepared from JHE-02-010A using the same procedure as described for the preparation of JHE-02-137. JHE-02-017A: off-white solid, yield 81%. Mp=199-199.5° C.; $^1$H NMR (DMSO-$d_6$, 400 MHz) δ 7.98 (d, J=8.8 Hz, 1H), 7.49-7.47 (m, 2H), 7.17 (dd, J=8.0 Hz, 8.0 Hz, 1H), 6.96 (t, J=5.6 Hz, 1H, NH), 6.90 (s, 1H), 6.84 (d, J=8.4 Hz, 1H), 6.77 (d, J=8.4 Hz, 1H), 3.91 (t, J=8.8 Hz, 2H), 3.29-3.17 (m, 8H), 2.93-2.90 (m, 4H), 2.43 (t, J=7.2 Hz, 2H); HPLC 97% [$t_R$=2.65, 70% acetonitrile in water (0.1% TFA)]; HPLC 97% [$t_R$=6.49, 70% methanol in water (0.1% TFA)]; HRMS (ESI-ve) m/z calcd. for $C_{22}H_{26}ClN_4O_5S$, 493.1307 (M+H)$^+$. found 493.1304 (M−H)$^+$.

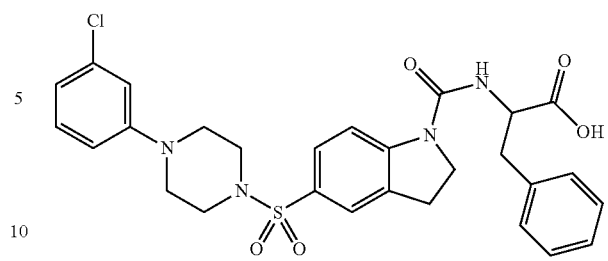

(JHE-02-019B) 2-(5-(4-(3-Chlorophenyl)piperazin-1-ylsulfonyl)indoline-1-carboxamido)-3-phenylpropanoic acid JHE-02-019B was prepared from JHE-02-014 using the same procedure as described for the preparation of JHE-02-137. JHE-02-019B: light pink solid, yield 74%. Mp=134-135° C.; $^1$H NMR (CD$_3$CN, 400 MHz) δ 7.98 (d, J=9.2 Hz, 1H), 7.54-7.52 (m, 2H), 7.35-7.19 (m, 6H), 6.93 (s, 1H), 6.87-6.83 (m, 2H), 5.72 (d, J=8.4 Hz, 1H), 4.63-4.57 (m, 1H), 3.99-3.87 (m, 2H), 3.27-3.20 (m, 7H), 3.11-3.05 (m, 5H); HPLC 97% [$t_R$=4.33, 70% acetonitrile in water (0.1% TFA)]; HPLC 98% [$t_R$=18.15, 70% methanol in water (0.1% TFA)]; HRMS (ESI-ve) m/z calcd. for $C_{28}H_{30}ClN_4O_5S$, 569.1620 (M+H)$^+$. found 569.1627 (M+H)$^+$.

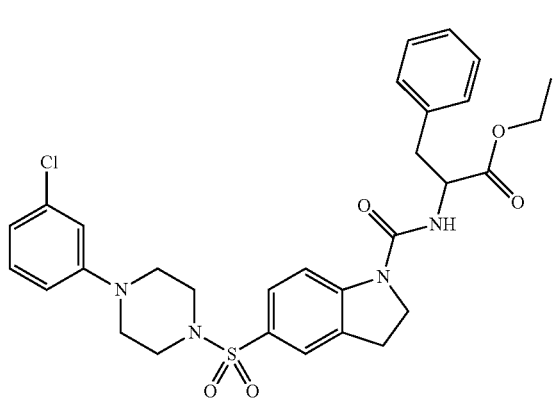 [SMILES: CCOC(=O)C(Cc1ccccc1)NC(=O)N1CCc2cc(S(=O)(=O)N3CCN(c4cccc(Cl)c4)CC3)ccc21]

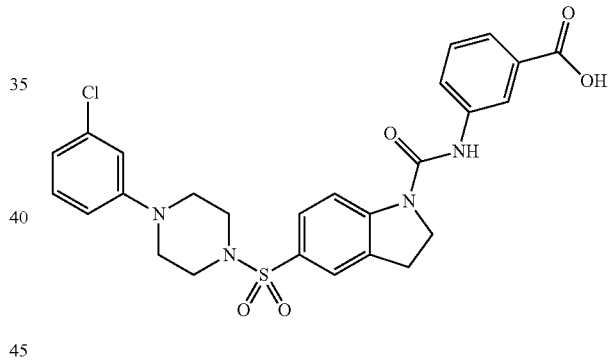

(JHE-02-020B) 3-(5-(4-(3-Chlorophenyl)piperazin-1-ylsulfonyl)indoline-1-carboxamido)benzoic acid (JHE-02-014) Ethyl 2-(5-(4-(3-chlorophenyl)piperazin-1-ylsulfonyl)indoline-1-carboxamido)-3-phenylpropanoate JHE-02-014 was prepared using the same procedure as described for the preparation of JHE-02-032A. JHE-02-014: pale yellow solid, yield 100%. Mp=123-124° C.; $^1$H NMR (CD$_3$CN, 400 MHz) δ 7.98 (d, J=9.2 Hz, 1H), 7.54-7.51 (m, 2H), 7.35-7.26 (m, 5H), 7.20 (dd, J=8.0 Hz, 8.0 Hz, 1H), 6.91 (dd, J=2.0, Hz, 2.0 Hz, 1H), 6.84-6.81 (m, 2H), 5.90 (t, J=8.0 Hz, 1H, NH), 4.65-4.60 (m, 1H), 4.15 (q, J=7.2 Hz, 2H), 4.03-3.88 (m, 2H), 3.26-3.21 (m, 7H), 3.11-3.03 (m, 5H), 1.22 (t, J=7.2 Hz, 3H); HPLC 97% [$t_R$=9.40, 70% acetonitrile in water (0.1% TFA)]; HPLC 97% [$t_R$=8.73, 70% methanol in water (0.1% TFA)].

(JHE-02-015B) Ethyl 3-(5-(4-(3-chlorophenyl)piperazin-1-ylsulthnyl)indoline-1-carboxamido)benzoate was prepared from the indoline JHE-01-120 and the corresponding acid chloride using the same procedure as described for the preparation of JHE-02-32A. Then JHE-02-020B was hydrolyzed from JHE-02-015B using the same procedure as described for the preparation of JHE-02-137. JHE-02-020B: white solid, yield 100%. Mp=250° C. decomposed; NMR (CD$_3$CN, 400 MHz) δ 8.24 (s, 1H), 8.15 (d, J=9.2 Hz, 1H), 7.81 (d, J=8.0 Hz, 1H), 7.73 (d, J=8.0 Hz, 1H), 7.61-7.59 (m, 2H), 7.50-7.44 (m, 2H), 7.21 (dd, J=8.0 Hz, 8.0 Hz, 1H), 6.92 (s, 1H), 6.86-6.82 (m, 2H), 4.21 (t, J=8.8 Hz, 2H), 3.33 (t, J=8.8 Hz, 2H), 3.27 (t, J=5.2 Hz, 4H), 3.07 (t, J=5.2 Hz, 4H); HRMS (ESI-ve) m/z calcd. for $C_{26}H_{26}ClN_4O_5S$, 541.1307 (M+H)$^+$. found 541.1303 (M+H)$^+$.

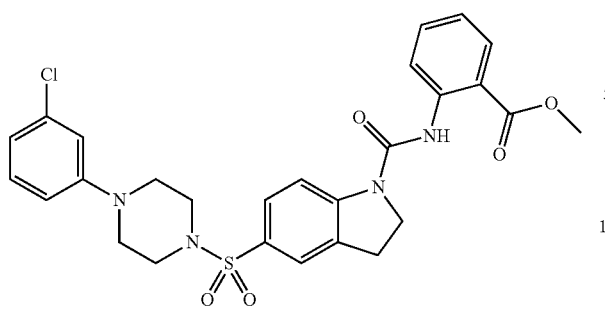

(JHE-02-015A) Methyl 2-(5-(4-(3-chlorophenyl)piperazin-1-ylsulfonyl)indoline-1-carboxamido)benzoate JHE-02-015A was prepared using the same procedure as described for the preparation of JHE-02-032A. JHE-02-015A: off-white solid. Mp=229.5-230° C.; $^1$H NMR (CD$_3$CN, 400 MHz) δ 10.85 (s, 1H, NH), 8.65 (d, J=8.8 Hz, 1H), 8.20 (d, J=9.2 Hz, 1H), 8.08 (dd, J=8.0 Hz, 1.6 Hz, 1H), 7.65-7.61 (m, 3H), 7.20 (d, J=8.0 Hz, 1H), 7.14 (d, J=8.0 Hz, 1H), 6.91 (s, 1H), 6.86-6.82 (m, 2H), 4.29 (t, J=8.8 Hz, 2H), 3.94 (s, 3H), 3.67 (t, J=8.8 Hz, 2H), 3.27 (t, =5.6 Hz, 4H), 3.08 (t, J=5.6 Hz, 4H); HPLC 98% [t$_R$=17.68, 70% acetonitrile in water (0.1% TFA)]; HRMS (ESI-ve) m/z calcd. for C$_{22}$H$_{25}$ClN$_3$O$_6$S 494.1147 (M+H)$^+$. found 494.1147 (M+H)$^+$.

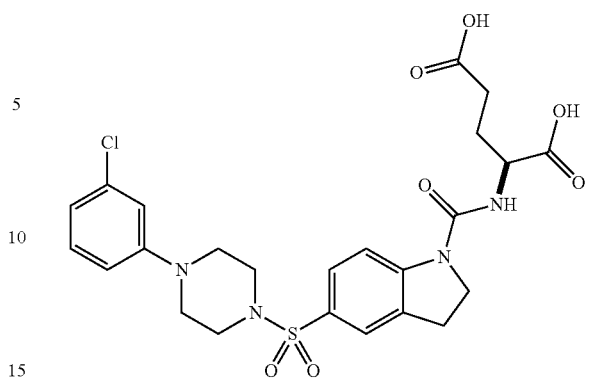

(JHE-02-052) (S)-2-(5-(4-(3-Chlorophenyl)piperazin-1-ylsulfonyl)indoline-1-carboxamido)pentanedioic acid (JHE-02-052) was hydrolyzed in the same fashion as JHE-01-137 from the corresponding ester (not reported here) which was prepared according the procedure described as for the preparation of JHE-02-32A. JHE-02-052: pale yellow solid, yield 81%. Mp=181-181.5° C.; $^1$H NMR (DMSO-d$_6$, 400 MHz) δ 7.95 (d, J=8.4 Hz, 1H), 7.49 (s, 2H), 7.48 (d, J=8.4 Hz, 1H), 7.17 (dd, J=8.0 Hz, 8.0 Hz, 1H), 7.00 (d, J=8.0 Hz, 1H), 6.90 (s, 1H), 6.84 (d, J=8.0 Hz, 1H), 6.78 (d, J=8.0 Hz, 1H), 4.13-4.19 (m, 1H), 4.08-3.96 (m, 2H), 3.24-3.18 (m, 6H), 2.94-2.90 (m, 4H), 2.33 (t, J=7.6 Hz, 2H), 2.08-1.99 (m, 1H), 1.96-1.84 (m, 1H); $^{13}$C NMR (DMSO-d$_6$, 100.6 MHz) δ 174.7, 174.5, 155.2, 152.3, 149.1, 134.5, 133.0, 131.2, 128.7, 126.8, 124.7, 119.5, 115.9, 115.0, 114.4, 53.2, 48.2, 48.0, 46.4, 31.1, 27.5, 26.5; HPLC 98% [t$_R$=2.31, 70% acetonitrile in water (0.1% TFA)]; HPLC 96% [t$_R$=5.41, 70% methanol in water (0.1% TFA)]; HRMS (ESI-ve) m/z calcd. for C$_{24}$H$_{28}$ClN$_4$O$_7$S, 551.1362 (M+H)$^+$. found 551.1362 (M+H)$^+$.

Scheme 5

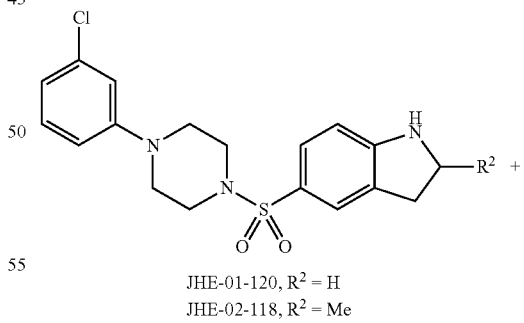

JHE-01-120, R$^2$ = H
JHE-02-118, R$^2$ = Me

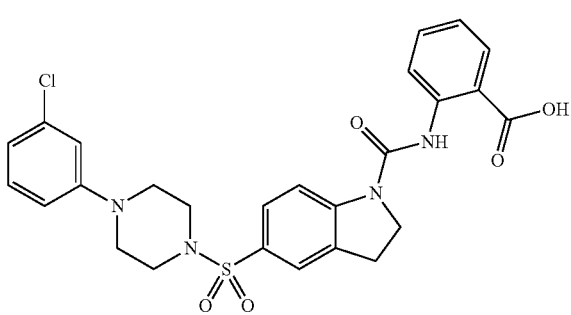 [SMILES: O=C(O)c1ccccc1NC(=O)N1CCc2cc(S(=O)(=O)N3CCN(c4cccc(Cl)c4)CC3)ccc21]

(JHE-02-020A) 2-(5-(4-(3-Chlorophenyl)piperazin-1-ylsulfonyl)indoline-1-carboxamido)benzoic acid JHE-02-020A was prepared from JHE-02-015A using the same procedure as described for the preparation of JHE-02-137. JHE-02-020A: pink solid, yield 88%. Mp=240.5-241° C.; $^1$H NMR (DMSO-d$_6$, 400 MHz) δ 8.53 (d, J=8.4 Hz, 1H), 8.11 (d, J=9.2 Hz, 1H), 7.99 (d, J=8.0 Hz, 1H), 7.61-7.56 (m, 3H), 7.17 (dd, J=8.4 Hz, 8.4 Hz, 1H), 7.09 (dd, J=7.6 Hz, 7.6 Hz, 1H), 6.91 (s, 1H), 6.85 (d, J=8.0 Hz, 1H), 6.77 (d, J=8.0 Hz, 1H), 4.23 (t, J=8.8 Hz, 2H), 3.29-3.24 (m, 6H), 2.96-2.94 (m, 4H).

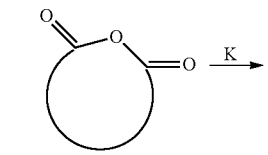

-continued

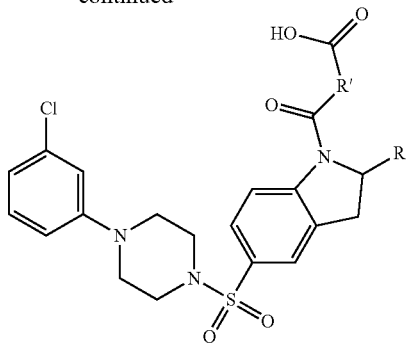

Reagents and conditions: (k) Anhydrides, CHCl₃, microwave, 100° C., 30 min.

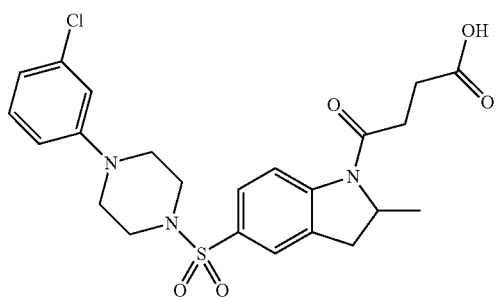 [SMILES: CC1Cc2cc(S(=O)(=O)N3CCN(c4cccc(Cl)c4)CC3)ccc2N1C(=O)CCC(=O)O]

(JHE-02419) 4-(5-(4-(3-Chlorophenyl)piperazin-1-ylsulfonyl)-2-methylindolin-1-yl)-4-oxobutanoic acid In a microwave reaction tube equipped with a magnetic stirring bar, JHE-02-118 (77.0 mg, 0.197 mmol) was dissolved in chloroform (0.5 mL) at room temperature. To the solution was added succinic anhydride (20 mg, 0.200 mmol). The reaction tube was capped and irradiated in the microwave reactor (Biotage Initiator I) at 100° C. for 30 minutes. The product was filtered and washed with dichloromethane and then with ethyl acetate/hexane (3:7) to afford the pure JHE-02-119 as pale pink solid, (81 mg, 84%). Mp=209.5-210° C.; ¹H NMR (DMSO-d₆, 400 MHz) δ 8.14 (s, 1H), 7.63 (s, 1H), 7.58 (d, J=8.4 Hz, 1H), 7.18 (dd, J=8.0 Hz, 8.0 Hz, 1H), 6.90 (d, J=2.0 Hz, 1H), 6.85 (dd, J=8.0 Hz, 2.0 Hz, 1H), 6.78 (dd, J=8.0 Hz, 2.0 Hz, 1H), 4.78-4.71 (m, 1H), 3.44-3.35 (m, 1H), 3.25-3.22 (m, 4H), 2.98-2.95 (m, 4H), 2.89-2.65 (m, 3H), 2.57-2.52 (m, 2H); HPLC 99% [$t_R$=3.32, 70% acetonitrile in water (0.1% TFA)]; HPLC 99% [$t_R$=7.36, 70% methanol in water (0.1% TFA)].

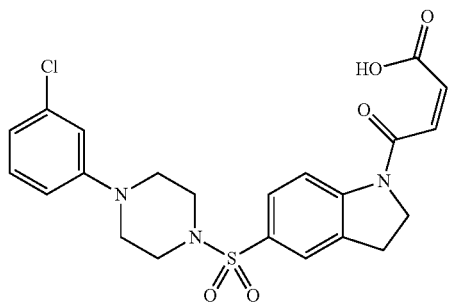 [SMILES: O=C(O)/C=C\C(=O)N1CCc2cc(S(=O)(=O)N3CCN(c4cccc(Cl)c4)CC3)ccc21]

(JHE-01-129A) (Z)-4-(5-(4-(3-Chlorophenyl)piperazin-1-ylsulfonyl)indolin-1-yl)-4-oxobut-2-enoic acid JHE-01-129A was prepared from JHE-01-120 and maleic anhydride using the same procedure as described for the preparation of JHE-02-119. JHE-01-129A: pale yellow solid, yield 68%. Mp=191-192° C.; ¹H NMR (DMSO-d₆, 400 MHz) δ 8.19 (d, J=8.0 Hz, 1H), 7.61 (s, 1H), 7.60 (d, J=8.0 Hz, 1H), 7.15 (dd, J=8.0 Hz, 8.0 Hz, 1H), 6.91 (s, 1H), 6.84 (d, J=8.0 Hz, 1H), 6.80-6.77 (m, 2H), 6.13 (d, J=12.0 Hz, 1H), 4.03 (t, J=8.0 Hz, 2H), 3.28-3.19 (m, 6H), 2.98-2.93 (m, 4H); HPLC 98% [$t_R$=3.04, 70% acetonitrile in water (0.1% TFA)]; HPLC 94% [$t_R$=5.63, 70% methanol in water (0.1% TFA)]; HRMS (ESI-ve) m/z calcd. for $C_{22}H_{23}ClN_3O_5S$, 476.1041 (M+H)⁺. found 476.1044 (M+H)⁺.

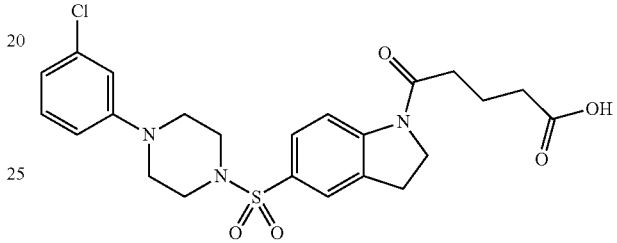

(JHE-01-129B) 5-(5-(4-(3-Chlorophenyl)piperazin-1-ylsulfonyl)indolin-1-yl)-5-oxopentanoic acid JHE-01-129B was prepared from JHE-01-120 and glutaric anhydride using the same procedure as described for the preparation of JHE-02-119. JHE-02-129B: white solid, yield 80%. Mp=220-220.5° C.; ¹H NMR (DMSO-d₆, 400 MHz) δ 8.24 (d, J=7.6 Hz, 1H), 7.57 (s, 1H), 7.55 (d, J=8.0 Hz, 1H), 7.17 (dd, J=8.0 Hz, 8.0 Hz, 1H), 7.20 (dd, J=8.0 Hz, 8.0 Hz, 1H), 6.90 (s, 1H), 6.84 (d, J=8.0 Hz, 1H), 6.77 (d, J=7.6 Hz, 1H), 4.12 (t, J=8.4 Hz, 2H), 3.27-3.18 (m, 6H), 2.93 (m, 4H), 2.48 (m, 2H), 2.28 (t, J=7.6 Hz, 2H), 1.78 (tt, J=7.6 Hz, 2H); HPLC 97% [$t_R$=3.11, 70% acetonitrile in water (0.1% TFA)]; HPLC 96% [$t_R$=7.53, 70% acetonitrile in water (0.1% TFA)]; HRMS (ESI-ve) m/z calcd. for $C_{23}H_{27}ClN_3O_5S$, 492.1355 (M+H)⁺. found 492.1359 (M+H)⁺.

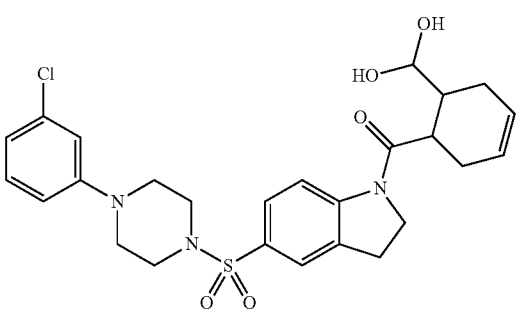 [SMILES: O=C(C1CC=CCC1C(O)O)N1CCc2cc(S(=O)(=O)N3CCN(c4cccc(Cl)c4)CC3)ccc21]

(JHE-02-007) 6-(5-(4-(3-Chlorophenyl)piperazin-1-ylsulfonyl)indoline-1-carbonyl)cyclohex-3-enecarboxylic acid JHE-02-007B was prepared from JHE-01-120 and 1,2,3,6-tetrahydrophthalic anhydride using the same procedure as described in the preparation of JHE-02-119. JHE-02-00: off-white solid, yield 49%. Mp=146.5-147.5° C.; $^1$H NMR (CD$_3$CN, 400 MHz) δ 8.28 (s, 1H), 7.62 (s, 1H), 7.60 (d, J=8.8 Hz, 1H), 7.20 (dd, J=8.4 Hz, 8.4 Hz, 1H), 6.91 (s, 1H), 6.85-6.82 (m, 2H), 5.78 (d, J=10.0 Hz, 1H), 5.66 (d, J=10.0 Hz, 1H), 4.33-4.21 (m, 2H), 3.39-3.33 (m, 1H), 3.30-3.25 (m, 6H), 3.07 (t, J=5.2 Hz, 4H), 2.97-2.93 (m, 1H), 2.77-2.72 (m, 1H), 2.50-2.11 (m, 3H); HRMS (ESI-ve) m/z calcd. for C$_{26}$H$_{29}$ClN$_3$O$_5$S, 530.1511 (M+H)$^+$. found 530.1505 (M+H)$^+$.

Figure 2:
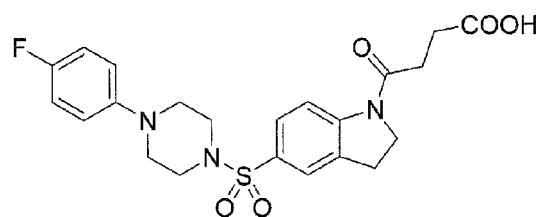
FIG. 2 is a Shp2 inhibitor of the present invention identified through high throughput screening.

Based on the high throughput screening, XW2-011B from HePTP screens, seen in FIG. 2, was synthesized, exhibiting an IC$_{50}$ of 47.8 μM. Focused libraries based on these hits have been prepared and assessed for Shp2 inhibitory activity. As an initial step, building block molecules were synthesized. An indoline skeleton molecule was then constructed, which was used to couple with the individual building blocks to afford the target molecules. Additional target molecules were also produced by coupling different acid chlorides and isocyanates with the indoline core. Finally, a chemical probe was also synthesized as a subunit for potential small molecules to develop another biologically active, small molecule skeleton like the indoline.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 4,559,157
U.S. Pat. No. 4,608,392
U.S. Pat. No. 4,820,508
U.S. Pat. No. 4,992,478
U.S. Pat. No. 5,167,649
U.S. Pat. No. 6,960,648
U.S. Published Patent Application No. 20020035243
U.S. Published Patent Application No. 20020120100
U.S. Published Patent Application No. 20030032594
European Patent No. EP 0 470 702 A1
Mohi M. G. and Neel B. G. (2007) The role of Shp2 (PTPN11) in cancer. *Curr Opin Genet & Dev.*, 17:23-30.
Alonso A., Sasin J., Bottini N., Friedberg Il., Friedberg Id., Osterman A., Godzik A., Hunter T., Dixon J., Mustelin T. (2004) Protein tyrosine phophatases in the human genome. *Cell*, 117:699-711.
Salmond J. and Alexander R. (2006) SHP2 forecast for the immune system:fog gradually clearing. *Trends Immunol*, 27:154-60.
Hellmuth, K., Grosskopf, S., Lum, C. T., Wurtele, M., Roder, N., von Kries, J. P., Rosario, M., Rademann, J. and Birchmeier, W. (2008) Specific inhibitors of the protein tyrosine phosphatase Shp2 identified by high-throughput docking, *Proc Natl Acad Sci USA* 105, 7275-7280
Noren-Muller A., et al. (2006) Discovery of protein phosphatase inhibitor classes by biology-oriented synthesis. *Proc Natl Acad Sci USA.*, 103:10606-11.
Borror A. L., et al. (1988) Regioselectivity of electrophilic aromatic substitution: Syntheses of 6- and 7-Sulfamoylindolines and -indoles. *J Org. Chem.*, 46:2047-2052.
Fraley M. E., et al. (2004) Optimization of the indoyl quinolinone class of KDR (VEGFR-2) kinase inhibitors: effects of 5-amido- and 5-sulphonamido-indolyl groups on pharmocokinetics and hERG binding. *Bioorg & Med Chem. Letters.*, 14:351-355.
Goodwin T. E., et al. (2000) Synthesis of $^{13}$C, $^2$H$_3$-Salmeterol: An analytical internal standard for pharmacokinetic studies. *J Labelled Cpd. Radiopharm.*, 43, 65-75.
Herschhorn A., et al. (2007) De Novo parallel design, synthesis and evaluation of inhibitors against the reverse transcriptase of human immunodeficiency virus type-1 and drug-resistant variants. *J Med Chem*, 50:2370-2384.
Toyoizumi T, Mick R. Abbas A E, Kang E H, Kaiser L R, Molnar-Kimber K L (1999) "Combined therapy with chemotherapeutic agents and herpes simplex virus type IICP34.5 mutant (HSV-1716) in human non-small cell lung cancer" *Human Gene Therapy*, 10(18):17.

We claim:
1. A Shp2 inhibitor compound having the chemical structure shown in formula I:

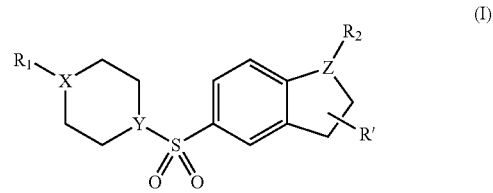

or a pharmaceutically acceptable salt or hydrate thereof, wherein:
X, Y, and Z are N;
R$_1$ is: phenyl substituted with one or more of Cl, Br, I, COOH, or C(R$_3$)$_3$, where R$_3$ can independently be halogen or OR$_4$, where R$_4$ can be H or alkyl; or methylphenyl optionally substituted with one or more of Cl, Br, or I;
R$_2$ is:
1) ethanoyl substituted with fluoro, chloro, bromo, iodo, OH, OR$_4$, C(O)OH, or C(O)ONa, unsubstituted phenyl, or phenyl substituted with one or more of fluoro, chloro, bromo, iodo, methyl, ethyl, propyl, butyl, C$_5$-C$_{20}$ alkyl, OH, OR$_4$, or C(O)OR$_5$, where R$_4$ is methyl, ethyl, propyl, butyl or C$_5$-C$_{20}$ alkyl, and where R$_5$ is H, Na, methyl, ethyl, propyl, butyl or C$_5$-C$_{20}$ alkyl;
propanoyl optionally unsaturated and substituted with fluoro, chloro, bromo, iodo, OH, OR$_4$, C(O)OH, C(O)ONa, unsubstituted phenyl, or phenyl substituted with one or more of fluoro, chloro, bromo, iodo, methyl, ethyl, propyl, butyl, C$_5$-C$_{20}$ alkyl, OH, OR$_4$, or C(O)OR$_5$, where R$_4$ is methyl, ethyl, propyl, butyl or C$_5$-C$_{20}$ alkyl, and where R$_5$ is H, Na, methyl, ethyl, propyl, butyl or C$_5$-C$_{20}$ alkyl;
butanoyl, optionally unsaturated and unsubstituted or substituted with fluoro, chloro, bromo, iodo, OH, OR$_4$, C(O)OH, C(O)ONa, unsubstituted phenyl, or phenyl substituted with one or more of fluoro, chloro, bromo, iodo, methyl, ethyl, propyl, butyl, C$_5$-C$_{20}$ alkyl, OH, OR$_4$, or C(O)OR$_5$, where R$_4$ is methyl, ethyl, propyl, butyl or C$_5$-C$_{20}$ alkyl, and where R$_5$ is H, Na, methyl, ethyl, propyl, butyl or C$_5$-C$_{20}$ alkyl; or $C_5$-$C_{21}$ alkanoyl, optionally unsaturated and unsubstituted or substituted with fluoro, chloro, bromo, iodo, OH, $OR_4$, C(O)OH, C(O)ONa, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$, where $R_4$ is methyl, ethyl, propyl, butyl, or $C_5$-$C_{20}$ alkyl, and where $R_5$ is H, Na, methyl, ethyl, propyl, butyl or $C_5$-$C_{20}$ alkyl;

2) phenylcarbonyl substituted with fluoro, chloro, bromo, iodo, OH, $OR_4$, or $C(O)OR_5$, where $R_4$ is methyl, ethyl, propyl, butyl, or $C_5$-$C_{20}$ alkyl, and where $R_5$ can be H, Na, methyl, ethyl, propyl, butyl or $C_5$-$C_{20}$ alkyl;

3) cyclobutylcarbonyl substituted with fluoro, chloro, bromo, iodo, OH, $OR_4$, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$ where $R_4$ is methyl, ethyl, propyl, butyl or $C_5$-$C_{20}$ alkyl and where $R_5$ is H, Na, methyl, ethyl, propyl, butyl or $C_5$-$C_{20}$ alkyl;

cyclopentylcarbonyl optionally unsaturated and unsubstituted or substituted with fluoro, chloro, bromo, iodo, OH, $OR_4$, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$, where $R_4$ is methyl, ethyl, propyl, butyl, or $C_5$-$C_{20}$ alkyl, and where $R_5$ is H, Na, methyl, ethyl, propyl, butyl or $C_5$-$C_{20}$ alkyl; or cyclohexylcarbonyl optionally unsaturated and unsubstituted or substituted with fluoro, chloro, bromo, iodo, OH, $OR_4$, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$, where $R_4$ is methyl, ethyl, propyl, butyl, or $C_5$-$C_{20}$ alkyl, and where $R_5$ is H, Na, methyl, ethyl, propyl, butyl, or $C_5$-$C_{20}$ alkyl; or

4) —$C(O)NH_2$;

—$C(O)NR_6R_7$ where $R_6$ and $R_7$ are independently methyl, ethyl, propyl, butyl, $C_5$-$C_{20}$ alkyl, or phenyl, wherein any of which can be optionally substituted with one or more of halogen, alkyl, $OR_4$, OH, $C(R_3)_3$, or phenyl is further substituted with $C(O)OR_5$, where $R_3$ is independently fluoro, chloro, bromo, or iodo, where $R_4$ is methyl, ethyl, propyl, butyl, or $C_5$-$C_{20}$ alkyl, and where $R_5$ is H, Na, methyl, ethyl, propyl, butyl or $C_5$-$C_{20}$ alkyl; or —$C(O)NHR_6$ where $R_6$ is methyl, ethyl, propyl, butyl, $C_5$-$C_{20}$ alkyl, or phenyl, any of which can be optionally substituted with one or more of halogen, alkyl, $OR_4$, OH, $C(R_3)_3$, or phenyl is further substituted with $C(O)OR_5$, where $R_3$ is independently fluoro, chloro, bromo, or iodo, where $R_4$ is methyl, ethyl, propyl, butyl, or $C_5$-$C_{20}$ alkyl, and where $R_5$ is H, Na, methyl, ethyl, propyl, butyl or $C_5$-$C_{20}$ alkyl; and R' is H, methyl, or $C_2$-$C_{20}$ alkyl.

2. The compound of claim 1, wherein $R_1$ is phenyl optionally substituted with one or more of —Cl, —COOH, —$CF_3$, or —$OCH_3$.

3. The compound of claim 1, wherein —$OR_4$ is —$OCH_3$ or —$OCH_2CH_3$.

4. The compound of claim 1, wherein $R_1$ has a structure selected from:

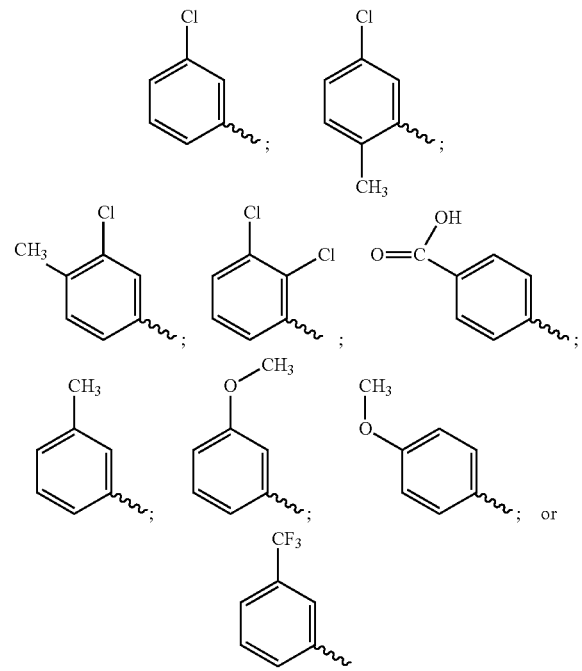

wherein

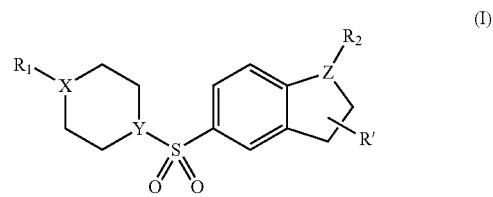

indicates the point of attachment.

5. The compound of claim 1, wherein $R_2$ is propanoyl substituted with one or more of —OH, —COOH, phenyl, or —$OR_4$, wherein $R_4$ is alkyl, or wherein $R_2$ is $C_4$-$C_{20}$ alkanoyl optionally substituted with one or more of —OH, —COOH, phenyl, or $OR_4$ wherein $R_4$ is alkyl.

6. A composition comprising a compound having the chemical structure shown in formula I:

or a pharmaceutically acceptable salt or hydrate thereof, wherein:

X, Y, and Z are N;

$R_1$ is: phenyl substituted with one or more of Cl, Br, I, COOH, or $C(R_3)_3$, where $R_3$ can independently be halogen or $OR_4$, where $R_4$ can be H or alkyl; or methylphenyl optionally substituted with one or more of Cl, Br, or I;

$R_2$ is:

1) ethanoyl substituted with fluoro, chloro, bromo, iodo, OH, $OR_4$, C(O)OH, or C(O)ONa, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$, where $R_4$ is methyl, ethyl, propyl, butyl or $C_5$-$C_{20}$ alkyl, and where $R_5$ is H, Na, methyl, ethyl, propyl, butyl or $C_5$-$C_{20}$ alkyl;

propanoyl optionally unsaturated and substituted with fluoro, chloro, bromo, iodo, OH, $OR_4$, C(O)OH, C(O)ONa, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$, where $R_4$ is methyl, ethyl, propyl, butyl or $C_5$-$C_{20}$ alkyl, and where $R_5$ is H, Na, methyl, ethyl, propyl, butyl or $C_5$-$C_{20}$ alkyl;

butanoyl, optionally unsaturated and unsubstituted or substituted with fluoro, chloro, bromo, iodo, OH, $OR_4$, C(O)OH, C(O)ONa, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$, where $R_4$ is methyl, ethyl, propyl, butyl or $C_5$-$C_{20}$ alkyl, and where $R_5$ is H, Na, methyl, ethyl, propyl, butyl or $C_5$-$C_{20}$ alkyl; or $C_5$-$C_{21}$ alkanoyl, optionally unsaturated and unsubstituted or substituted with fluoro, chloro, bromo, iodo, OH, $OR_4$, C(O)OH, C(O)ONa, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$, where $R_4$ is methyl, ethyl, propyl, butyl, or $C_5$-$C_{20}$ alkyl, and where $R_5$ is H, Na, methyl, ethyl, propyl, butyl or $C_5$-$C_{20}$ alkyl;

2) phenylcarbonyl substituted with fluoro, chloro, bromo, iodo, OH, $OR_4$, or $C(O)OR_5$, where $R_4$ is methyl, ethyl, propyl, butyl, or $C_5$-$C_{20}$ alkyl, and where $R_5$ can be H, Na, methyl, ethyl, propyl, butyl or $C_5$-$C_{20}$ alkyl;

3) cyclobutylcarbonyl substituted with fluoro, chloro, bromo, iodo, OH, $OR_4$, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$ where $R_4$ is methyl, ethyl, propyl, butyl or $C_5$-$C_{20}$ alkyl and where $R_5$ is H, Na, methyl, ethyl, propyl, butyl or $C_5$-$C_{20}$ alkyl;

cyclopentylcarbonyl optionally unsaturated and unsubstituted or substituted with fluoro, chloro, bromo, iodo, OH, $OR_4$, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$, where $R_4$ is methyl, ethyl, propyl, butyl, or $C_5$-$C_{20}$ alkyl, and where $R_5$ is H, Na, methyl, ethyl, propyl, butyl or $C_5$-$C_{20}$ alkyl; or cyclohexylcarbonyl optionally unsaturated and unsubstituted or substituted with fluoro, chloro, bromo, iodo, OH, $OR_4$, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$, where $R_4$ is methyl, ethyl, propyl, butyl, or $C_5$-$C_{20}$ alkyl, and where $R_5$ is H, Na, methyl, ethyl, propyl, butyl, or $C_5$-$C_{20}$ alkyl; or

4) —$C(O)NH_2$;

—$C(O)NR_6R_7$ where $R_6$ and $R_7$ are independently methyl, ethyl, propyl, butyl, $C_5$-$C_{20}$ alkyl, or phenyl, wherein any of which can be optionally substituted with one or more of halogen, alkyl, $OR_4$, OH, $C(R_3)_3$, or phenyl is further substituted with $C(O)OR_5$, where $R_3$ is independently fluoro, chloro, bromo, or iodo, where $R_4$ is methyl, ethyl, propyl, butyl, or $C_5$-$C_{20}$ alkyl, and where $R_5$ is IL Na, methyl, ethyl, propyl, butyl or $C_5$-$C_{20}$ alkyl; or —$C(O)NHR_6$ where $R_6$ is methyl, ethyl, propyl, butyl, $C_5$-$C_{20}$ alkyl, or phenyl, any of which can be optionally substituted with one or more of halogen, alkyl, $OR_4$, OH, $C(R_3)_3$, or phenyl is further substituted with $C(O)OR_5$, where $R_3$ is independently fluoro, chloro, bromo, or iodo, where $R_4$ is methyl, ethyl, propyl, butyl, or $C_5$-$C_{20}$ alkyl, and where $R_5$ is H, Na, methyl, ethyl, propyl, butyl or $C_5$-$C_{20}$ alkyl; and R' is H, methyl, or $C_2$-$C_{24}$ alkyl.

7. A kit comprising in one or more containers a compound having the chemical structure shown in formula I:

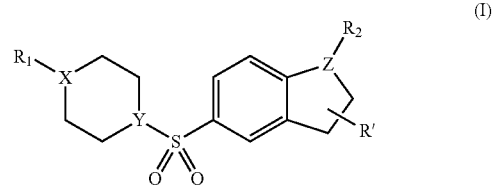

or a pharmaceutically acceptable salt or hydrate thereof, wherein:

X, Y, and Z are N;

$R_1$ is: phenyl substituted with one or more of Cl, Br, I, COOH, or $C(R_3)_3$, where $R_3$ can independently be halogen or $OR_4$, where $R_4$ can be H or alkyl; or methylphenyl optionally substituted with one or more of Cl, Br, or I;

$R_2$ is:

1) ethanoyl substituted with fluoro, chloro, bromo, iodo, OH, $OR_4$, C(O)OH, or C(O)ONa, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$ where $R_4$ is methyl, ethyl, propyl, butyl or $C_5$-$C_{20}$ alkyl and where $R_5$ is H, Na, methyl, ethyl, propyl, butyl or $C_5$-$C_{20}$ alkyl;

propanoyl optionally unsaturated and substituted with fluoro, chloro, bromo, iodo, OH, $OR_4$, C(O)OH, C(O)ONa, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$, where $R_4$ is methyl, ethyl, propyl, butyl or $C_5$-$C_{20}$ alkyl, and where $R_5$ is H, Na, methyl, ethyl, propyl, butyl or $C_5$-$C_{20}$ alkyl;

butanoyl, optionally unsaturated and unsubstituted or substituted with fluoro, chloro, bromo, iodo, OH, $OR_4$, C(O)OH, C(O)ONa, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$, where $R_4$ is methyl, ethyl, propyl, butyl or $C_5$-$C_{20}$ alkyl, and where $R_5$ is H, Na, methyl, ethyl, propyl, butyl or $C_5$-$C_{20}$ alkyl; or $C_5$-$C_{21}$ alkanoyl, optionally unsaturated and unsubstituted or substituted with fluoro, chloro, bromo, iodo, OH, $OR_4$, C(O)OH, C(O)ONa, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$, where $R_4$ is methyl, ethyl, propyl, butyl, or $C_5$-$C_{20}$ alkyl, and where $R_5$ is H, Na, methyl, ethyl, propyl, butyl or $C_5$-$C_{20}$ alkyl;

2) phenylcarbonyl substituted with fluoro, chloro, bromo, iodo, OH, $OR_4$, or $C(O)OR_5$, where $R_4$ is methyl, ethyl, propyl, butyl, or $C_5$-$C_{20}$ alkyl, and where $R_5$ can be H, Na, methyl, ethyl, propyl, butyl or $C_5$-$C_{20}$ alkyl;

3) cyclobutylcarbonyl substituted with fluoro, chloro, bromo, iodo, OH, $OR_4$, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$ where $R_4$ is methyl, ethyl, propyl, butyl or $C_5$-$C_{20}$ alkyl and where $R_5$ is H, Na, methyl, ethyl, propyl, butyl or $C_5$-$C_{20}$ alkyl;

cyclopentylcarbonyl optionally unsaturated and unsubstituted or substituted with fluoro, chloro, bromo, iodo, OH, $OR_4$, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$, where $R_4$ is methyl, ethyl, propyl, butyl, or $C_5$-$C_{20}$ alkyl, and where $R_5$ is H, Na, methyl, ethyl, propyl, butyl or $C_5$-$C_{20}$ alkyl; or cyclohexylcarbonyl optionally unsaturated and unsubstituted or substituted with fluoro, chloro, bromo, iodo, OH, $OR_4$, unsubstituted phenyl, or phenyl substituted with one or more of fluoro, chloro, bromo, iodo, methyl, ethyl, propyl, butyl, $C_5$-$C_{20}$ alkyl, OH, $OR_4$, or $C(O)OR_5$, where $R_4$ is methyl, ethyl, propyl, butyl, or $C_5$-$C_{20}$ alkyl, and where $R_5$ is H, Na, methyl, ethyl, propyl, butyl, or $C_5$-$C_{20}$ alkyl; or

4) —C(O)NH$_2$;

—C(O)NR$_6$R$_7$ where $R_6$ and $R_7$ are independently methyl, ethyl, propyl, butyl, $C_5$-$C_{20}$ alkyl, or phenyl, wherein any of which can be optionally substituted with one or more of halogen, alkyl, $OR_4$, OH, $C(R_3)_3$, or phenyl is further substituted with $C(O)OR_5$, where $R_3$ is independently fluoro, chloro, bromo, or iodo, where $R_4$ is methyl, ethyl, propyl, butyl, or $C_5$-$C_{20}$ alkyl, and where $R_5$ is H, Na, methyl, ethyl, propyl, butyl or $C_5$-$C_{20}$ alkyl; or —C(O)NHR$_6$ where $R_6$ is methyl, ethyl, propyl, butyl, $C_5$-$C_{20}$ alkyl, or phenyl, any of which can be optionally substituted with one or more of halogen, alkyl, $OR_4$, OH, $C(R_3)_3$, or phenyl is further substituted with $C(O)OR_5$, where $R_3$ is independently fluoro, chloro, bromo, or iodo, where $R_4$ is methyl, ethyl, propyl, butyl, or $C_5$-$C_{20}$ alkyl, and where $R_5$ is H, Na, methyl, ethyl, propyl, butyl or $C_5$-$C_{20}$ alkyl; and R' is H, methyl, or $C_2$-$C_{20}$ alkyl.

8. The compound of claim 1, wherein the compound has the structure:

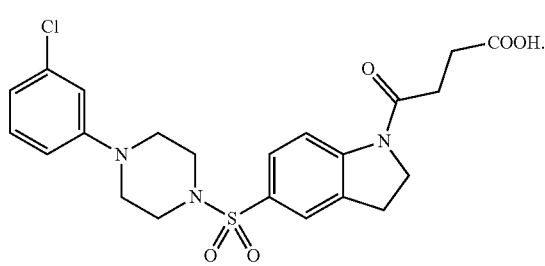 [SMILES: O=C(O)CCC(=O)N1CCc2cc(S(=O)(=O)N3CCN(c4cccc(Cl)c4)CC3)ccc21]

9. The composition of claim 6, wherein the compound has the structure:

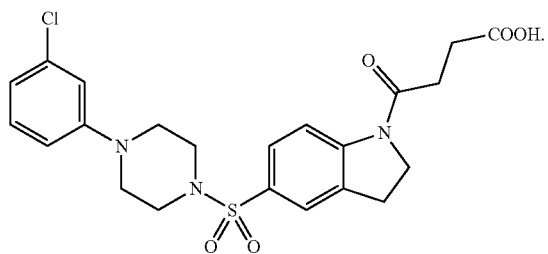 [SMILES: O=C(O)CCC(=O)N1CCc2cc(S(=O)(=O)N3CCN(c4cccc(Cl)c4)CC3)ccc21]

10. The kit of claim 7, wherein the compound has the structure:

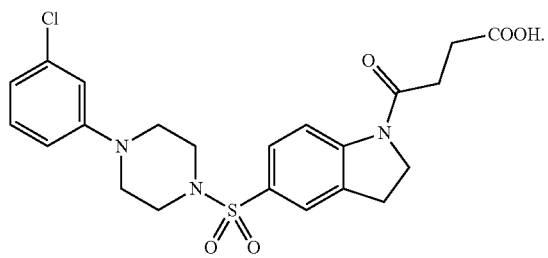 [SMILES: O=C(O)CCC(=O)N1CCc2cc(S(=O)(=O)N3CCN(c4cccc(Cl)c4)CC3)ccc21]

11. A Shp2 inhibitor compound having the chemical structure shown in formula I:

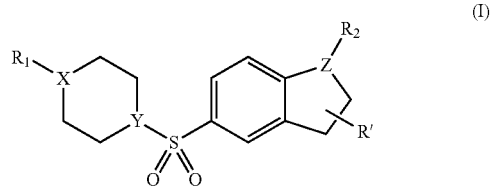

or a pharmaceutically acceptable salt or hydrate thereof, wherein:
X, Y, and Z are N;
$R_1$ is: phenyl substituted with one or more of Cl, Br, I, COOH, or $C(R_3)_3$, where $R_3$ can independently be halogen or $OR_4$, where $R_4$ can be H or alkyl; or methylphenyl optionally substituted with one or more of Cl, Br, or I;
$R_2$ has a structure selected from:

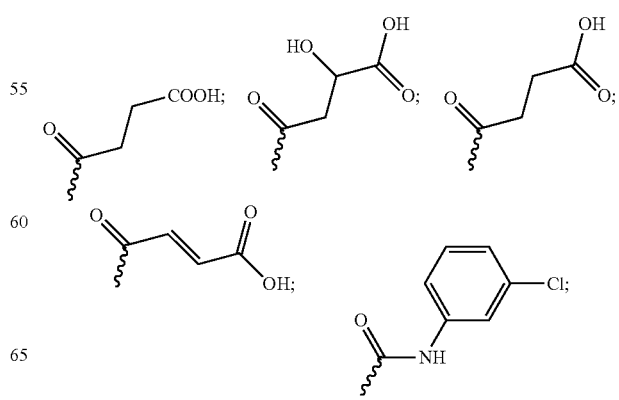

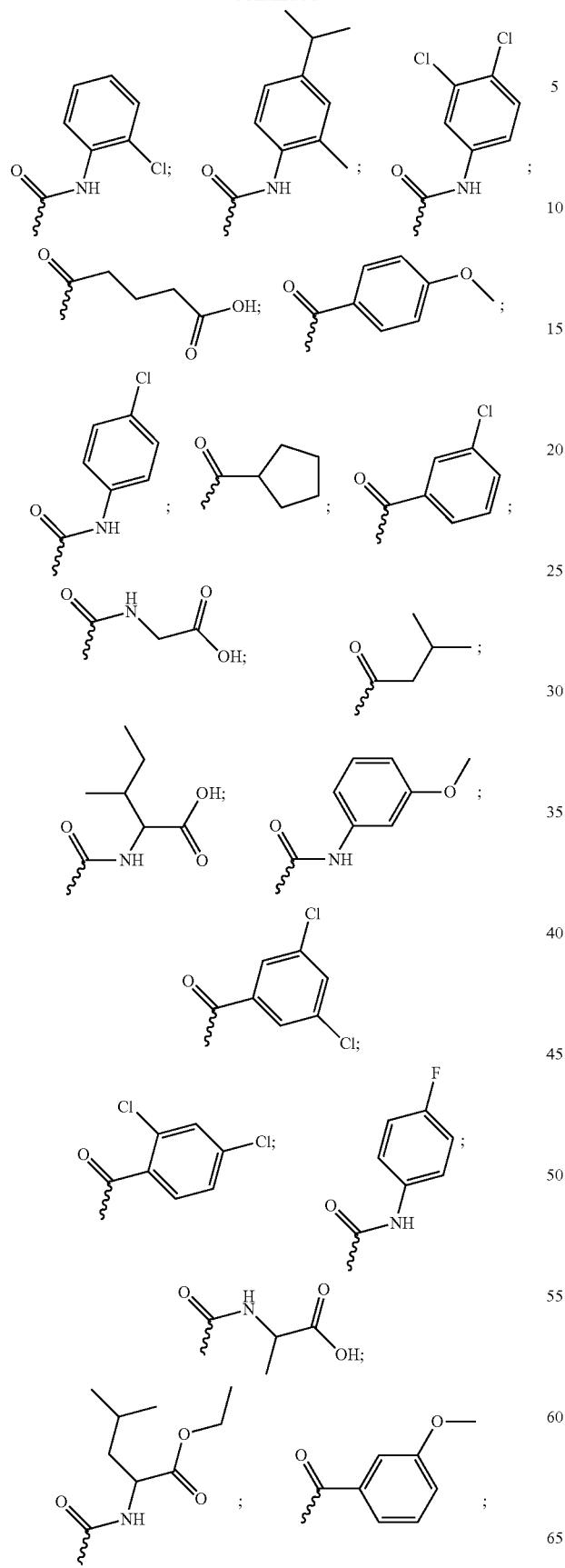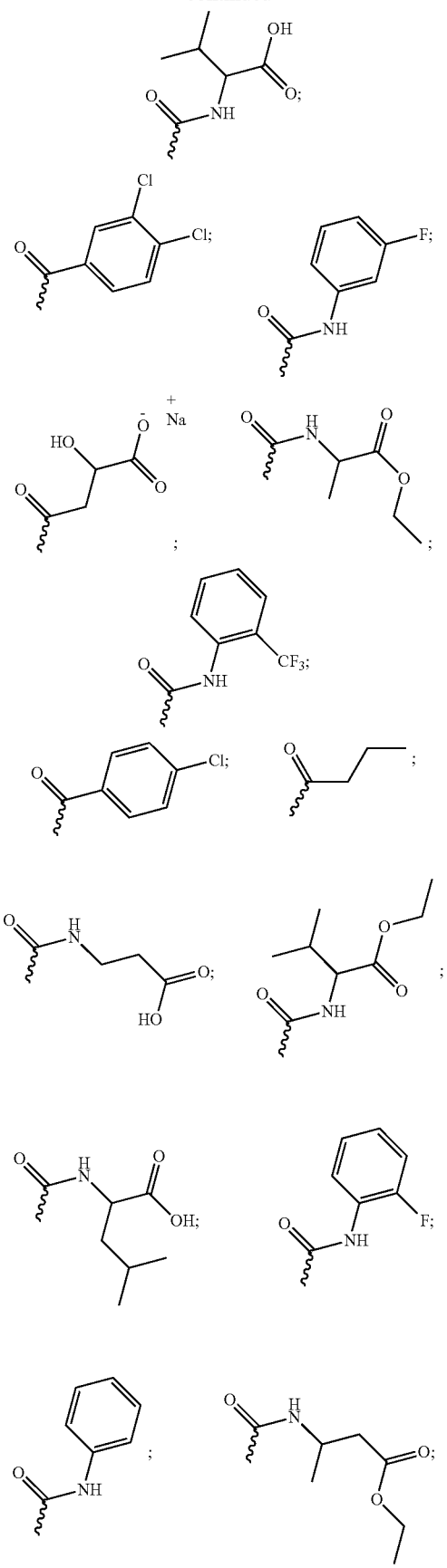

-continued
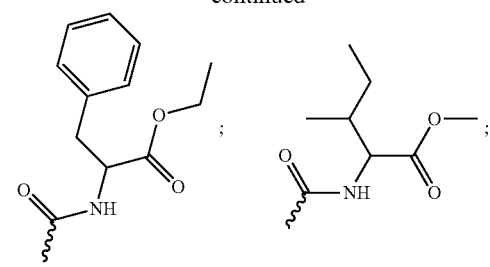
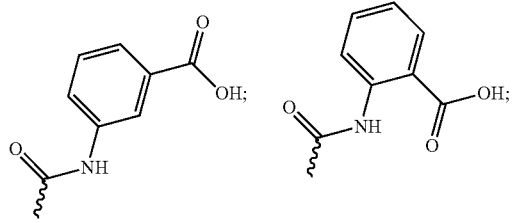
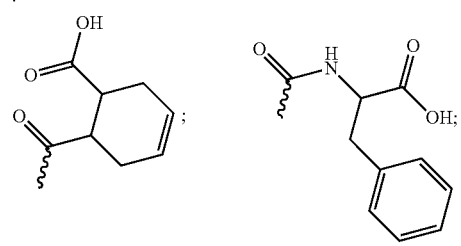
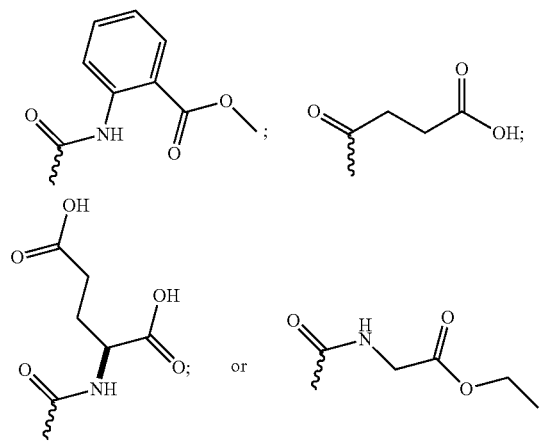
wherein
indicates the point of attachment; and
R' is H, methyl, or $C_2$-$C_{20}$ alkyl.
12. A compound having the structure:
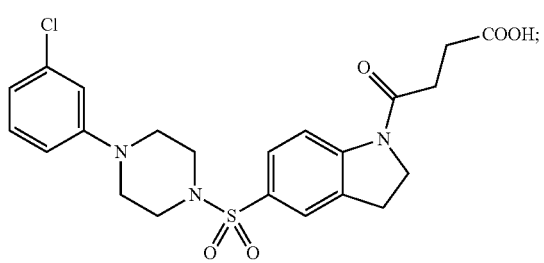
-continued
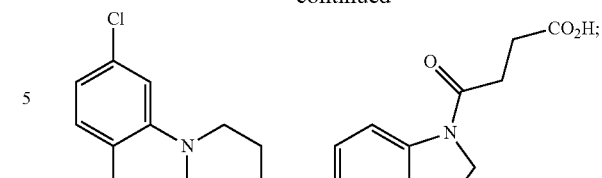
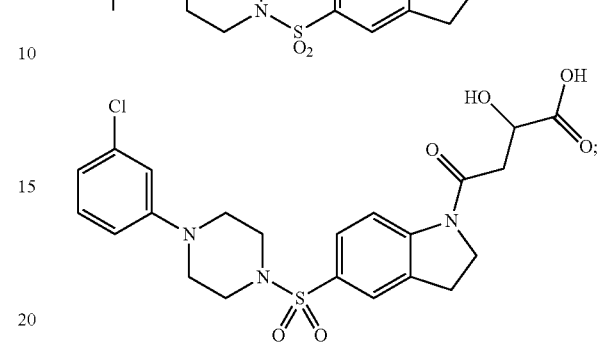
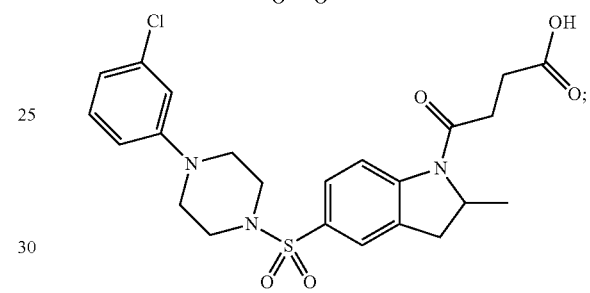
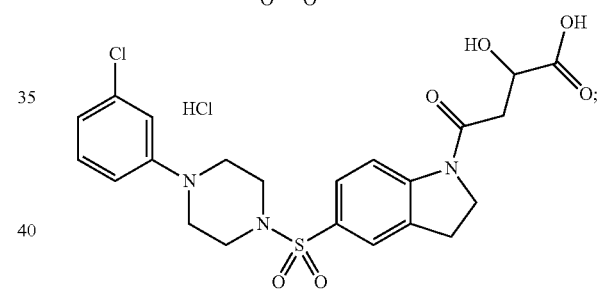
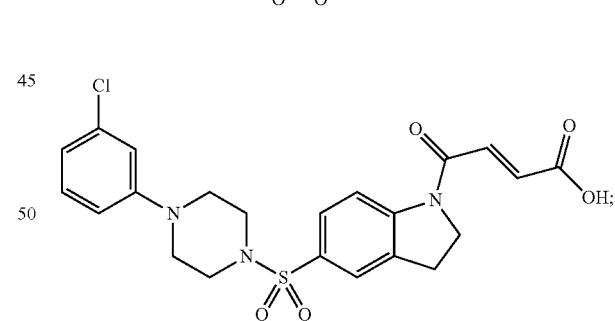
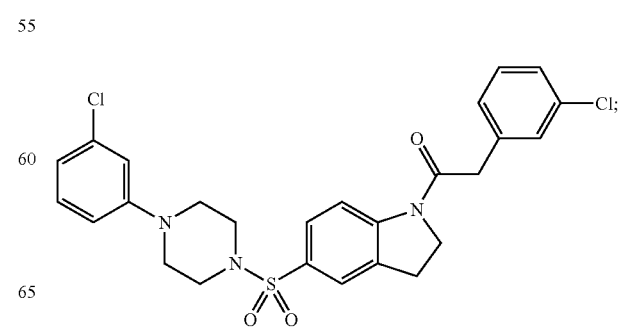

113
-continued
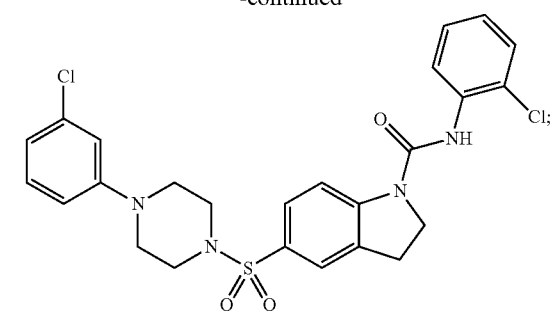
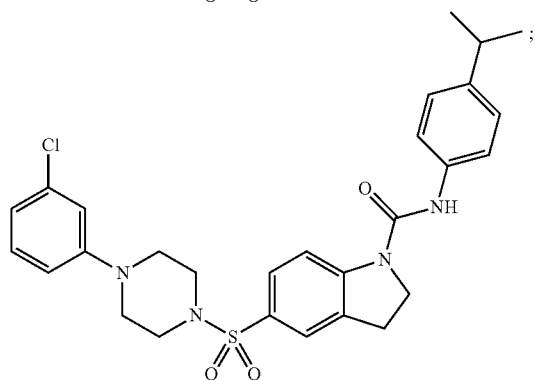
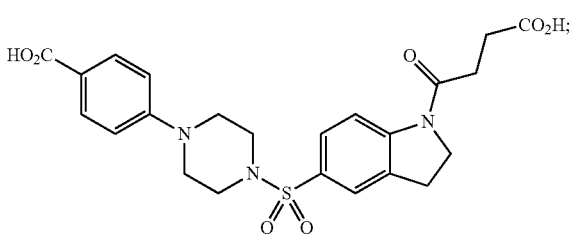
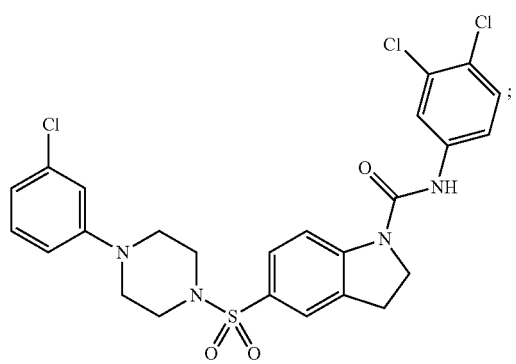
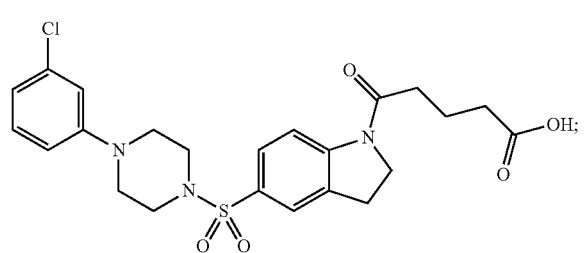
114
-continued
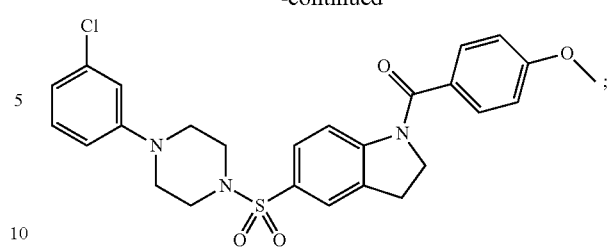
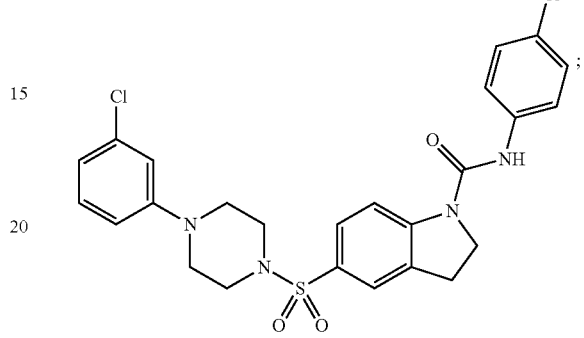
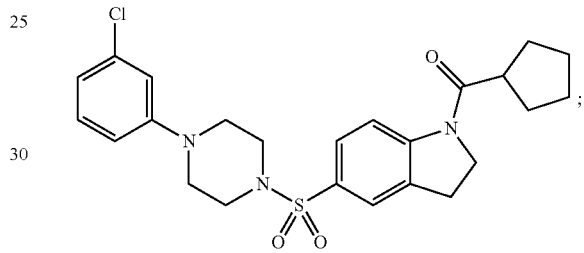
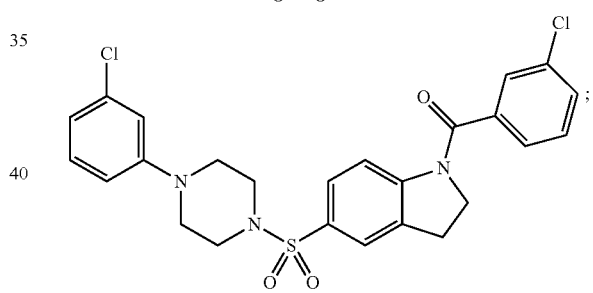
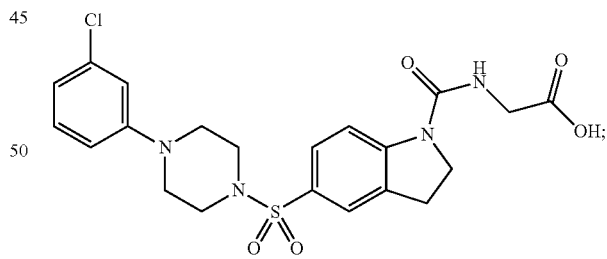
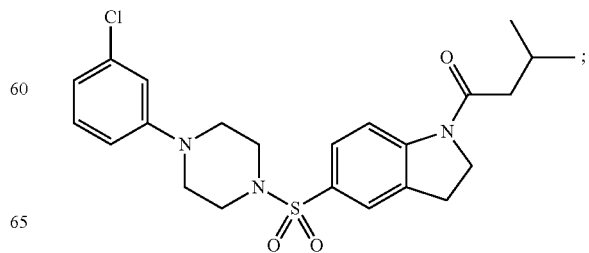

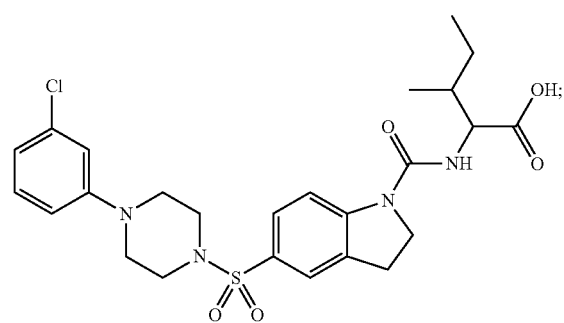
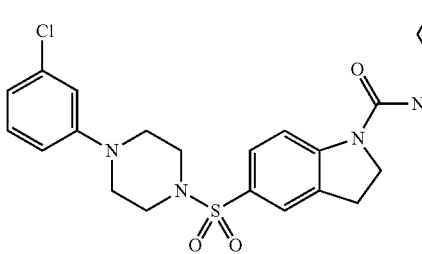
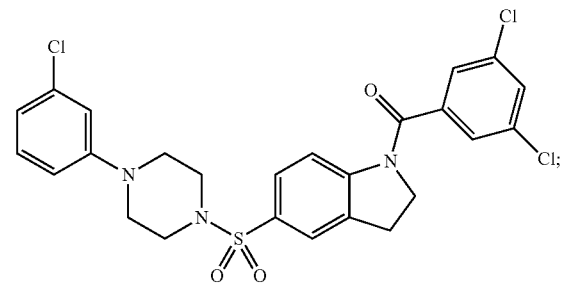
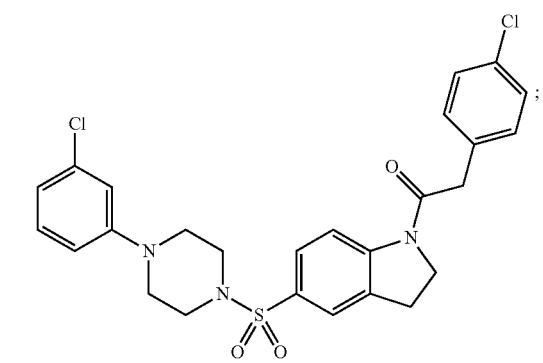
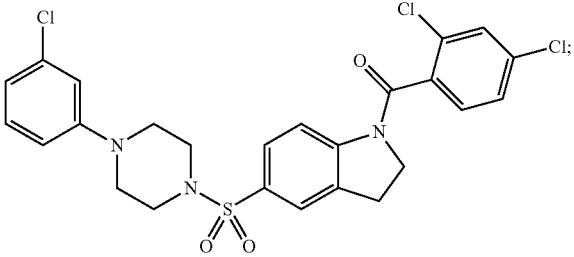
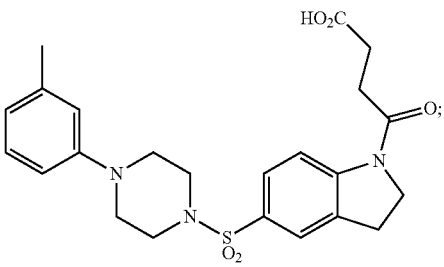
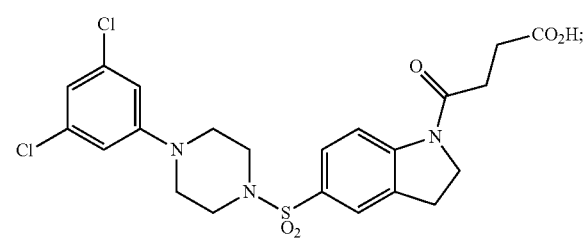
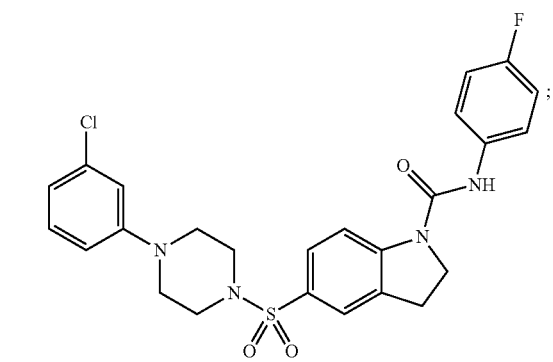
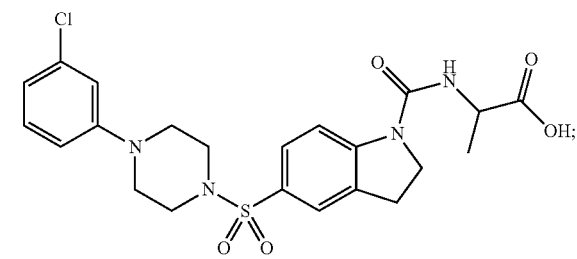
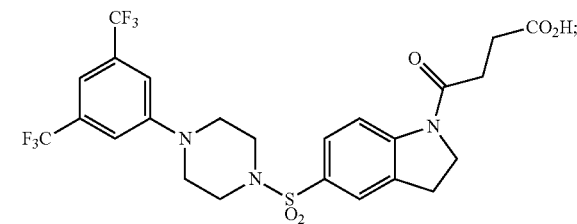
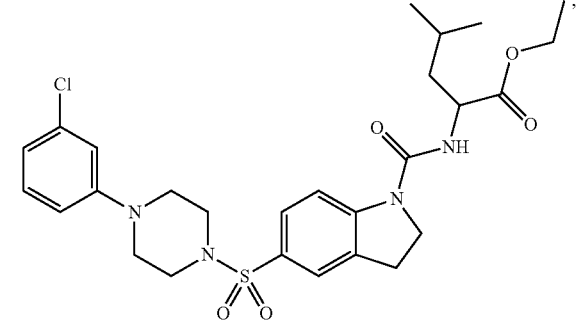

117
-continued
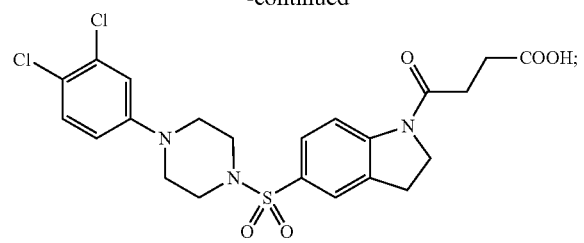
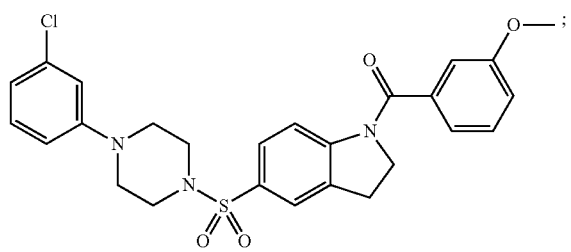
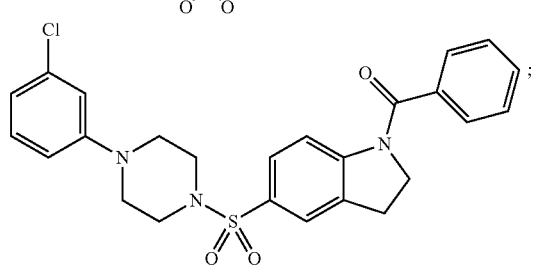
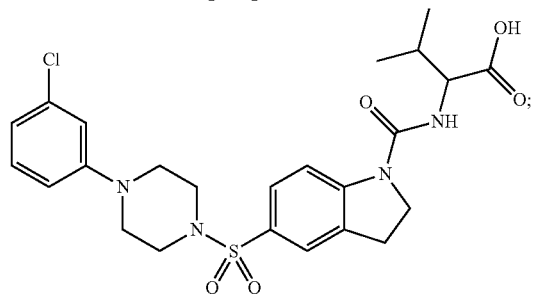
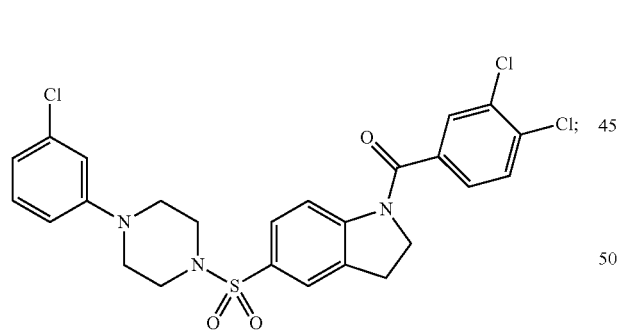
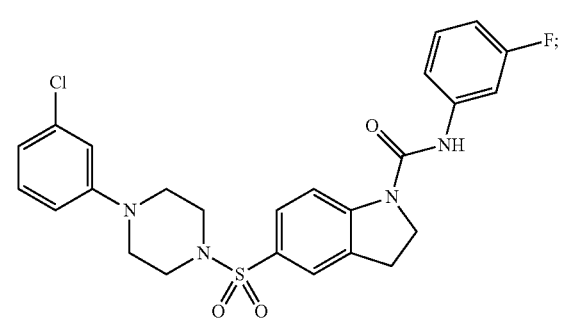
118
-continued
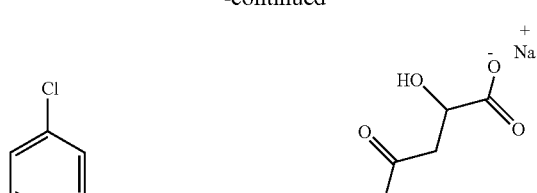
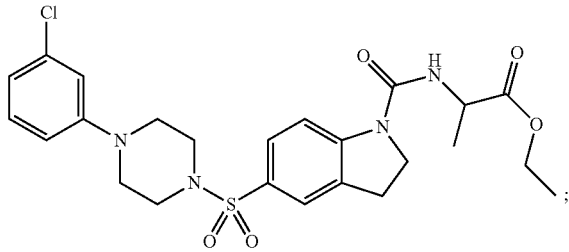
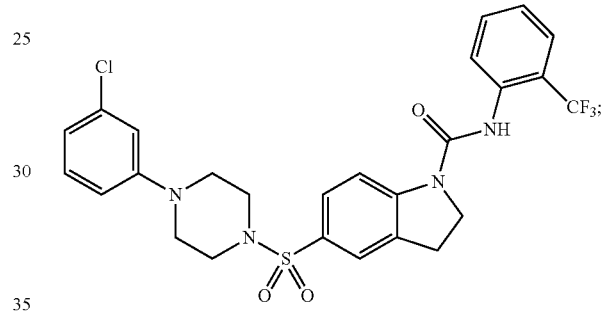
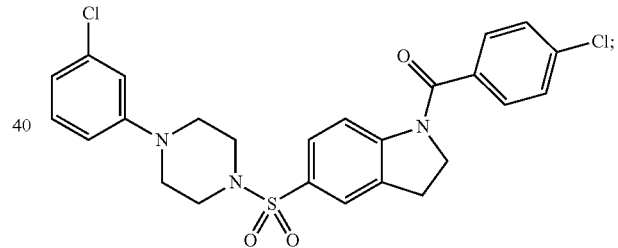
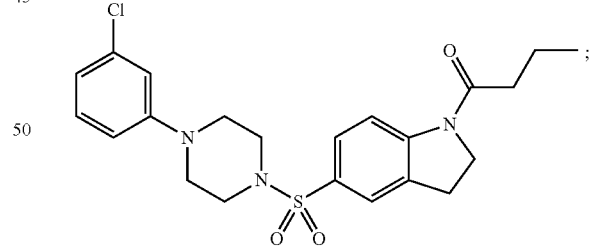
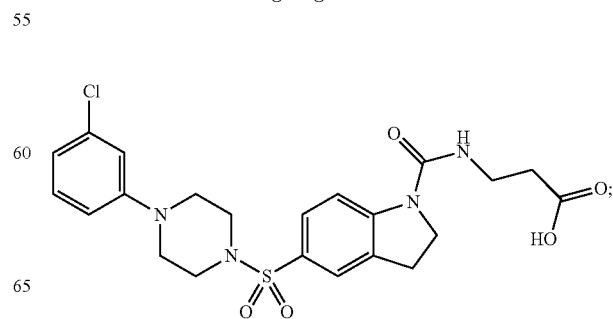

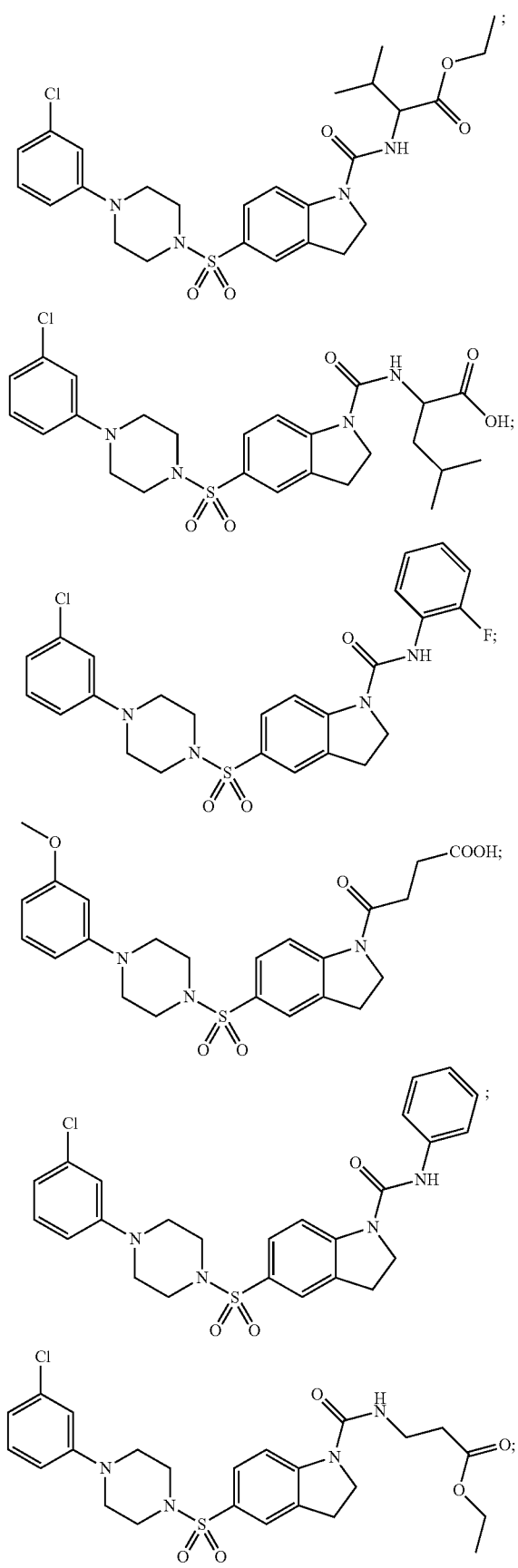
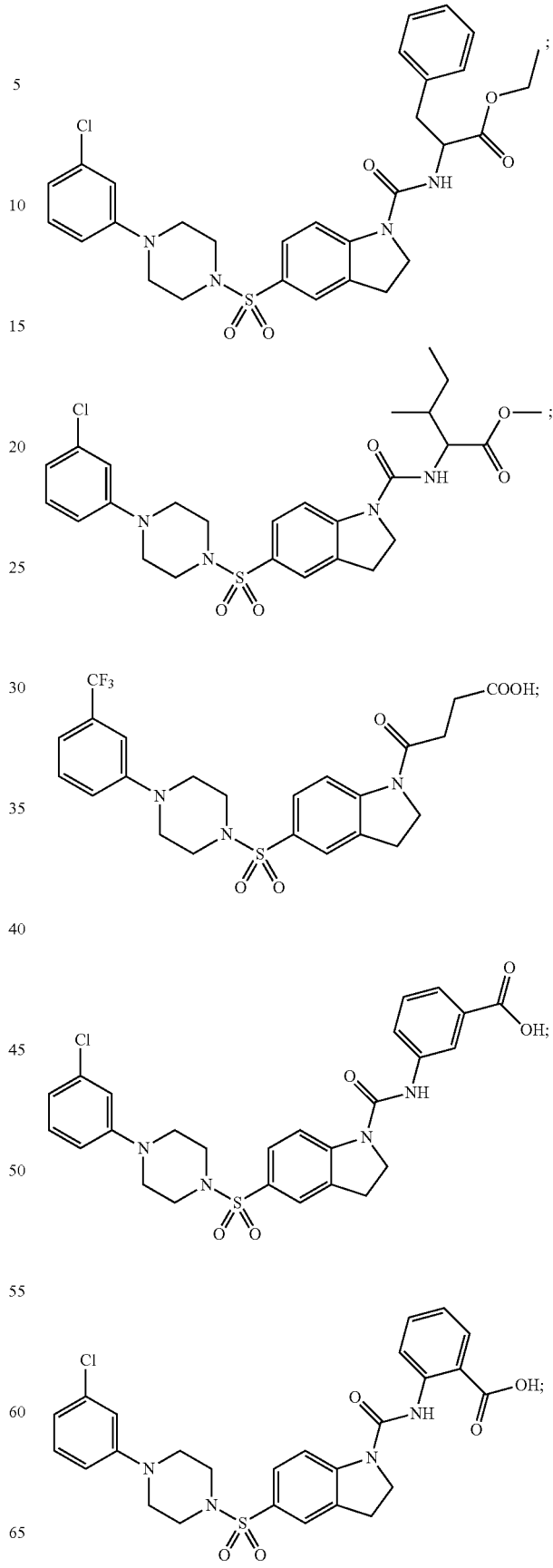

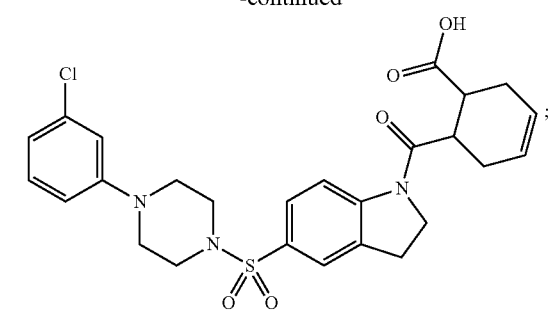
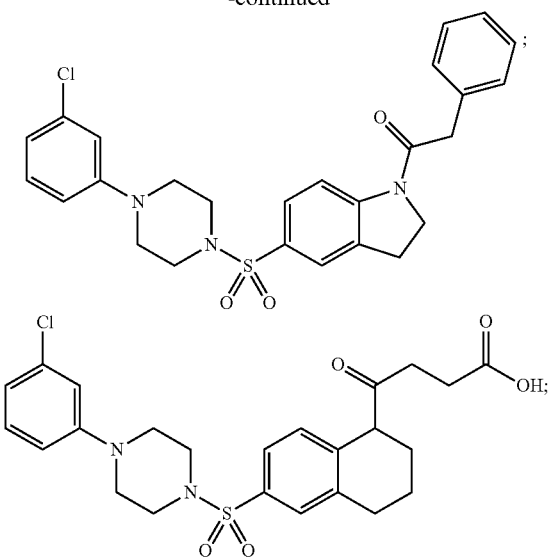
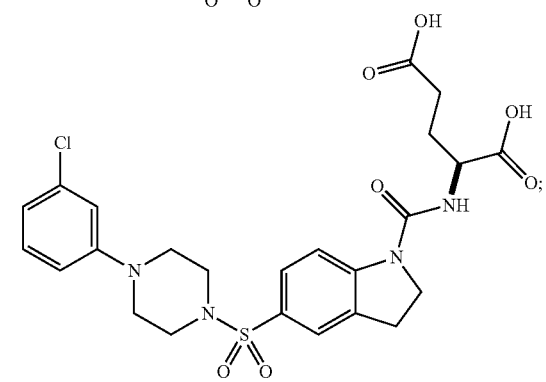
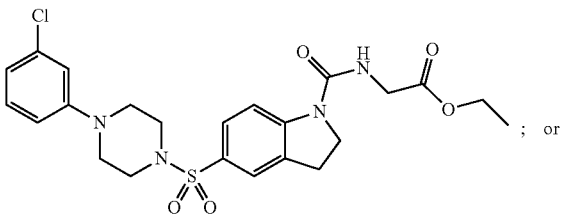
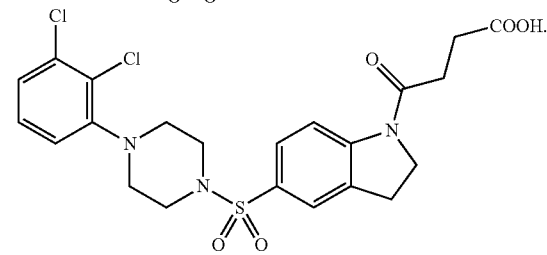
* * * * *

UNITED STATES PATENT AND TRADEMARK OFFICE
CERTIFICATE OF CORRECTION

PATENT NO. : 9,174,969 B2
APPLICATION NO. : 13/055113
DATED : November 3, 2015
INVENTOR(S) : Jie Wu et al.

It is certified that error appears in the above-identified patent and that said Letters Patent is hereby corrected as shown below:

Column 4,

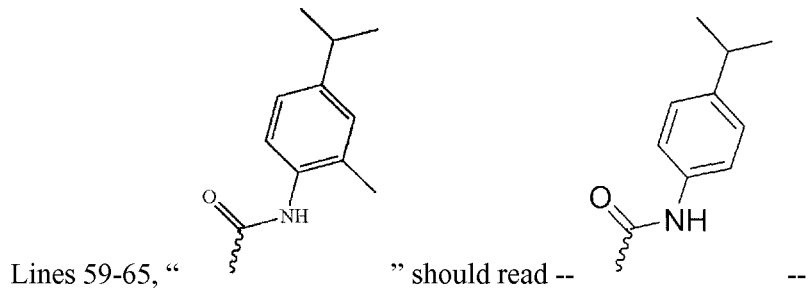

Lines 59-65, " " should read -- --

Column 5,

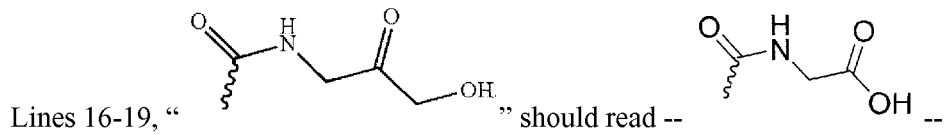

Lines 16-19, " " should read -- --

Column 6,

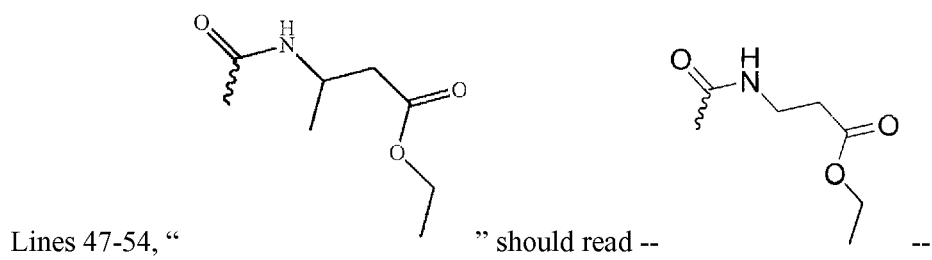

Lines 47-54, " " should read -- --

Column 9,
Line 28, "the teen parenteral" should read --the term parenteral--
Line 55, "variety of for ins." should read --variety of forms.--

Signed and Sealed this
Sixteenth Day of August, 2016

Michelle K. Lee
*Director of the United States Patent and Trademark Office*

Column 15,
Line 66, "also be for toed," should read --also be formed,--

Column 57,
Line 56, "an Alitech Kromasil" should read --an Alltech Kromasil--

Column 60,
Line 55, "37% HCl (1 L)]" should read --37% HCl (1 mL)]--

Column 64,
Line 21, "8.22 (dm J=" should read --8.22 (d, J=--
Line 42, "4-oxo-4-" should read --4-Oxo-4- --

Column 66,
Line 41, "XW2-0380" should read --XW2-038D--

Column 73,
Line 17, "JF024, n = 1, $R^3$ = 3,5-DiClPh" should read --JF025, n = 1, $R^3$ = 3,5-DiClPh--

Column 77,
Line 36, "(m, 414);" should read --(m, 4H);--
Line 66, "FIRMS" should read --HRMS--

Column 78,
Line 32, "446.1300 (M+H)" should read --446.1300 $(M+H)^+$--

Column 79,
Line 65, "FIRMS" should read --HRMS--

Column 82,
Line 17, "phenyleth an one" should read --phenylethanone--

Column 83,
Line 41, "JHE-02-017A, $R^4$ = (CH2)3CO$_2$H" should read --JHE-02-017A, $R^4$ = $(CH_2)_3CO_2H$--
Line 43, "JHE-02-017B, $R^4$ = (CH3)CHCO$_2$H" should read --JHE-02-017B, $R^4$ = $(CH_3)CHCO_2H$--
Line 44, "JHE-02010C," should read --JHE-02-010C,--

Column 87,
Line 51, "(J039)" should read --(JF039)--

Column 88,
Line 65, "FIRMS" should read --HRMS--

Column 93,
Line 26, "NMR" should read --$^1$H NMR--
Column 96,
Line 53, "1-ylsulthnyl)" should read --1-ylsulfonyl)--
Line 60, "NMR" should read --$^1$H NMR--
Column 97,
Line 29, "3.27 (t,=5.6 Hz, 4H)" should read --3.27 (t, J=5.6 Hz, 4H)--
Column 99,
Line 31, "(JHE-02419)" should read --(JHE-02-119)--
Column 100,
Lines 48-51, " 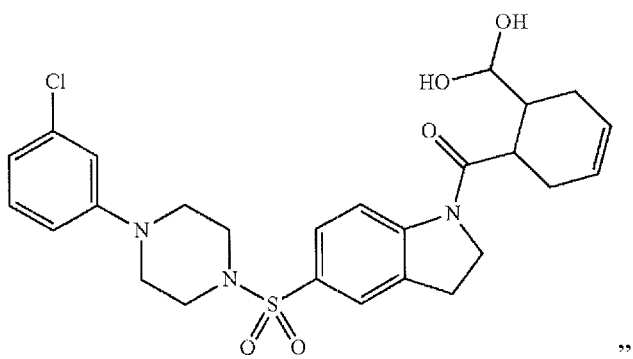 "
should read -- 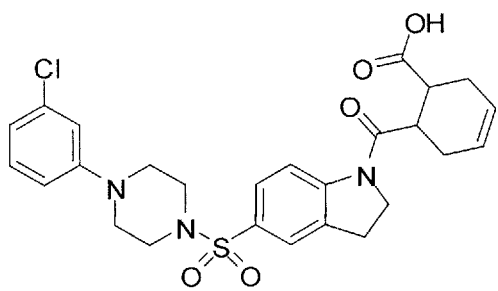 --
Column 105,
Lines 65-66, "where $R_5$ is IL Na," should read --where $R_5$ is H, Na,--
Column 106,
Line 9, "or $C_2$-$C_{24}$ alkyl." should read --or $C_2$-$C_{20}$ alkyl.--

CERTIFICATE OF CORRECTION (continued)
U.S. Pat. No. 9,174,969 B2

Column 109,

Lines 4-9, 2<sup>nd</sup> structure, " 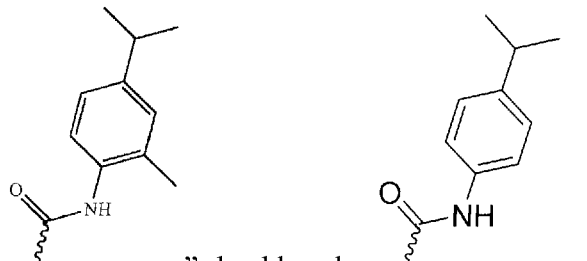 " should read --   --

Column 110,

Lines 59-63, 2<sup>nd</sup> structure, " 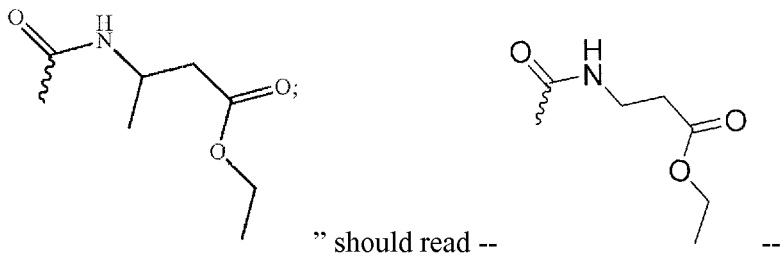 " should read --   --

Column 112,

Lines 53-65, " 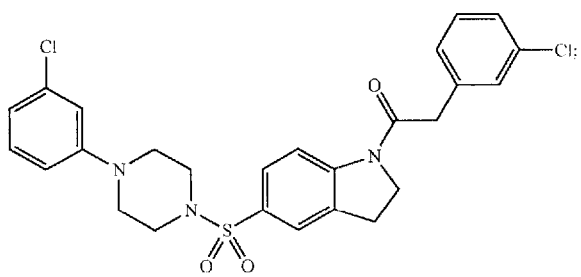 "

should read -- 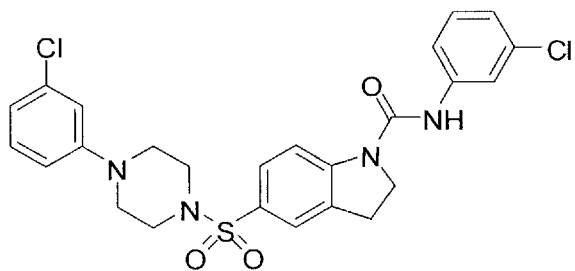 --

Column 113,

Lines 30-39, " 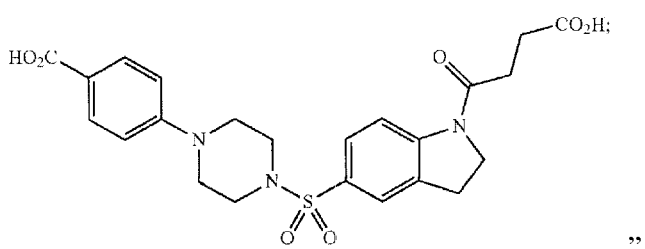 "

CERTIFICATE OF CORRECTION (continued)
U.S. Pat. No. 9,174,969 B2

Page 5 of 5 should read -- 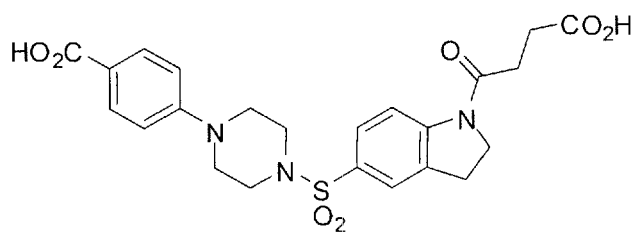 --

Column 122,

Lines 16-20, " 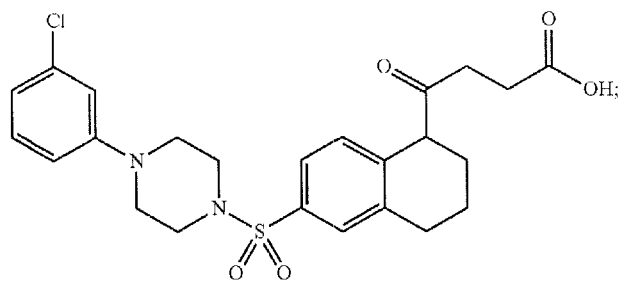 "

should read -- 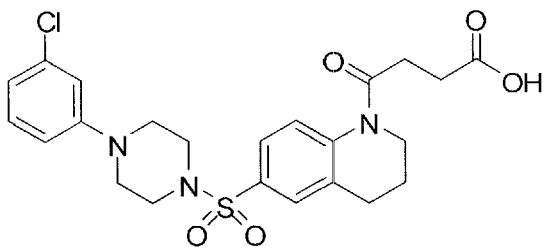 --